United States Patent
Karkera et al.

(10) Patent No.: US 10,478,494 B2
(45) Date of Patent: Nov. 19, 2019

(54) FGFR/PD-1 COMBINATION THERAPY FOR THE TREATMENT OF CANCER

(71) Applicant: ASTEX THERAPEUTICS LTD, Cambridge (GB)

(72) Inventors: Jayaprakash Karkera, Germantown, MD (US); Suso Jesus Platero, Washington Crossing, PA (US); Raluca Verona, Swarthmore, PA (US); Matthew V. Lorenzi, Philadelphia, PA (US)

(73) Assignee: ASTEX THERAPEUTICS LTD, Cambridge (GB)

( * ) Notice: Subject to any disclaimer, the term of this patent is extended or adjusted under 35 U.S.C. 154(b) by 142 days.

(21) Appl. No.: 15/079,136

(22) Filed: Mar. 24, 2016

(65) Prior Publication Data

US 2016/0287699 A1    Oct. 6, 2016

Related U.S. Application Data

(60) Provisional application No. 62/142,569, filed on Apr. 3, 2015.

(51) Int. Cl.
| | | |
|---|---|---|
| *A61K 45/06* | (2006.01) | |
| *C07K 16/28* | (2006.01) | |
| *A61K 31/498* | (2006.01) | |
| *A61K 39/395* | (2006.01) | |
| *C12Q 1/6886* | (2018.01) | |
| *G01N 33/574* | (2006.01) | |

(52) U.S. Cl.
CPC ........ *A61K 39/3955* (2013.01); *A61K 31/498* (2013.01); *A61K 45/06* (2013.01); *C07K 16/2818* (2013.01); *C12Q 1/6886* (2013.01); *G01N 33/57492* (2013.01); *C12Q 2600/158* (2013.01); *G01N 2333/70596* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 2,940,972 | A | 6/1960 | Roch |
| 4,666,828 | A | 5/1987 | Gusella |
| 4,683,202 | A | 7/1987 | Mullis |
| 4,801,531 | A | 1/1989 | Frossard |
| 5,192,659 | A | 3/1993 | Simons |
| 5,272,057 | A | 12/1993 | Smulson et al. |
| 5,700,823 | A | 12/1997 | Hirth et al. |
| 5,882,864 | A | 3/1999 | An et al. |
| 6,218,529 | B1 | 4/2001 | An et al. |
| 6,271,231 | B1 | 8/2001 | Bergstrand et al. |
| 6,331,555 | B1 | 12/2001 | Hirth et al. |
| 7,135,311 | B1 | 11/2006 | David et al. |
| 7,432,279 | B2 | 10/2008 | Green et al. |
| 8,409,577 | B2 | 4/2013 | Thompson et al. |
| 8,895,601 | B2 | 11/2014 | Saxty et al. |
| 9,067,998 | B1 | 6/2015 | Clube |
| 9,145,367 | B2 | 9/2015 | Tazi et al. |
| 9,221,804 | B2 | 12/2015 | Leonard et al. |
| 9,290,478 | B2 | 3/2016 | Saxty et al. |
| 9,303,029 | B2 | 4/2016 | Woodhead et al. |
| 9,303,030 | B2 * | 4/2016 | Angibaud ............ C07D 403/04 |
| 9,309,241 | B2 | 4/2016 | Angibaud et al. |
| 9,309,242 | B2 | 4/2016 | Berdini et al. |
| 9,399,028 | B2 | 7/2016 | Tavazoie et al. |
| 9,439,896 | B2 | 9/2016 | Berdini et al. |
| 9,447,098 | B2 | 9/2016 | Saxty et al. |
| 9,464,071 | B2 * | 10/2016 | Saxty ................... C07D 403/04 |
| 9,493,426 | B2 * | 11/2016 | Angibaud ............ C07D 403/12 |
| 9,527,844 | B2 | 12/2016 | Angibaud et al. |
| 9,737,544 | B2 * | 8/2017 | Angibaud .......... A61K 31/5377 |
| 9,757,364 | B2 * | 9/2017 | Angibaud .......... A61K 31/4375 |
| 9,850,228 | B2 | 12/2017 | Saxty et al. |
| 9,856,236 | B2 | 1/2018 | Saxty et al. |
| 9,902,714 | B2 | 2/2018 | Vermeulen |
| 10,039,759 | B2 | 8/2018 | Berdini et al. |
| 10,045,982 | B2 | 8/2018 | Berdini et al. |
| 10,052,320 | B2 | 8/2018 | Woodhead et al. |
| 10,085,982 | B2 | 10/2018 | Jovcheva et al. |
| 2003/0207886 | A1 | 11/2003 | Plücker et al. |

(Continued)

FOREIGN PATENT DOCUMENTS

| | | |
|---|---|---|
| CA | 2524525 | 12/2004 |
| CA | 2524948 | 12/2004 |

(Continued)

OTHER PUBLICATIONS

International Search Report for PCT/US2016/025482 dated Aug. 5, 2016.
Moreira Da Silva, R., "Novolumab: Anti-PD-1 monoclonal antibody cancer immunotherapy", *Drugs of the Future*, vol. 39, No. 1, pp. 15-24 (2014).
Ho, H.K., et al., "Current strategies for inhibiting FGFR activities in clinical applications: opportunities, challenges and toxicological considerations", *Drug Discovery Today*, vol. 19, Issue 1, Abstract only (2014).
Yan, L., et al., "An efficient synthesis of quinoxaline derivatives from 4-chloro-4-deoxy-α-D-galactose and their cytotoxic activities", *Bioorganic & Medicinal Chemistry Letters*, vol. 17, No. 3, 2006, pp. 609-612.

(Continued)

*Primary Examiner* — Peter J Reddig
(74) *Attorney, Agent, or Firm* — Heslin Rothenberg Farley & Mesiti P.C.

(57) ABSTRACT

Provided herein are combination therapies for the treatment of cancer. In particular, the disclosed methods are directed to treatment of cancer in a patient comprising administering an antibody that blocks the interaction between PD-1 and PD-L1 and an FGFR inhibitor, wherein the antibody that blocks the interaction between PD-1 and PD-L1 and the FGFR inhibitor are administered if one or more FGFR variants are present in a biological sample from the patient.

17 Claims, 5 Drawing Sheets

Specification includes a Sequence Listing.

(56) References Cited

U.S. PATENT DOCUMENTS

| | | |
|---|---|---|
| 2005/0261307 A1 | 11/2005 | Cai et al. |
| 2005/0272728 A1 | 12/2005 | Altenbach et al. |
| 2005/0272736 A1 | 12/2005 | Altenbach et al. |
| 2007/0123494 A1 | 5/2007 | Seipelt et al. |
| 2007/0149484 A1 | 6/2007 | Claus et al. |
| 2008/0116789 A1 | 5/2008 | Yamaguchi et al. |
| 2009/0054304 A1 | 2/2009 | Herbert et al. |
| 2009/0118261 A1 | 5/2009 | Aquila et al. |
| 2009/0221591 A1 | 9/2009 | Hartmann et al. |
| 2009/0263397 A1 | 10/2009 | Buck et al. |
| 2010/0228026 A1 | 9/2010 | Yoshida et al. |
| 2010/0234347 A1 | 9/2010 | Dollinger et al. |
| 2011/0123545 A1 | 5/2011 | Marsh et al. |
| 2012/0302572 A1 | 11/2012 | Kan et al. |
| 2013/0072457 A1* | 3/2013 | Saxty .................. C07D 403/04 514/80 |
| 2013/0096021 A1 | 4/2013 | Chinnaiyan et al. |
| 2013/0267525 A1 | 10/2013 | Saxty et al. |
| 2013/0296326 A1 | 11/2013 | Pollock |
| 2014/0037642 A1 | 2/2014 | McCaffery et al. |
| 2014/0288053 A1 | 9/2014 | Berdini et al. |
| 2014/0296236 A1 | 10/2014 | Berdini et al. |
| 2015/0017637 A1 | 1/2015 | Chinnaiyan et al. |
| 2015/0031669 A1 | 1/2015 | Woodhead et al. |
| 2015/0031703 A1* | 1/2015 | Suzuki ................ C12Q 1/6886 514/252.12 |
| 2015/0057293 A1 | 2/2015 | Angibaud et al. |
| 2015/0086584 A1 | 3/2015 | Gilboa et al. |
| 2015/0105368 A1 | 4/2015 | Saxty et al. |
| 2015/0183875 A1 | 7/2015 | Cobbold et al. |
| 2015/0191791 A1 | 7/2015 | Shibata |
| 2015/0203589 A1* | 7/2015 | Iavarone ................ C07K 16/40 424/138.1 |
| 2015/0210769 A1* | 7/2015 | Freeman ............ C07K 16/2896 424/136.1 |
| 2015/0239883 A1 | 8/2015 | Angibaud et al. |
| 2015/0291589 A1 | 10/2015 | Saxty et al. |
| 2015/0307945 A1 | 10/2015 | Nakanishi et al. |
| 2016/0031856 A1* | 2/2016 | Saxty .................. C07D 403/04 514/249 |
| 2016/0031990 A1 | 2/2016 | Steele et al. |
| 2016/0067336 A1 | 3/2016 | Fandi et al. |
| 2016/0075666 A1 | 3/2016 | Angibaud et al. |
| 2016/0090633 A1* | 3/2016 | Platero ................ C12Q 1/6886 506/2 |
| 2016/0108034 A1 | 4/2016 | Angibaud et al. |
| 2016/0122410 A1 | 5/2016 | Behrens et al. |
| 2016/0213677 A1 | 7/2016 | Angibaud et al. |
| 2016/0220564 A1 | 8/2016 | Woodhead et al. |
| 2016/0235744 A1 | 8/2016 | Berdini et al. |
| 2016/0243228 A1 | 8/2016 | Holash et al. |
| 2016/0287699 A1 | 10/2016 | Karkera et al. |
| 2016/0311800 A1 | 10/2016 | Saxty et al. |
| 2016/0347836 A1 | 12/2016 | Grosso |
| 2017/0000781 A1 | 1/2017 | Berdini et al. |
| 2017/0000796 A1 | 1/2017 | Saxty et al. |
| 2017/0021019 A1 | 1/2017 | Zibelman et al. |
| 2017/0100406 A1 | 4/2017 | Jovcheva et al. |
| 2017/0101396 A1 | 4/2017 | Vermeulen et al. |
| 2017/0105978 A1 | 4/2017 | Angibaud et al. |
| 2017/0119763 A1 | 5/2017 | Jovcheva et al. |
| 2017/0145102 A1 | 5/2017 | Pierce et al. |
| 2017/0145103 A1 | 5/2017 | Pierce et al. |
| 2018/0021332 A1 | 1/2018 | Broggini |
| 2018/0127397 A1 | 5/2018 | Saxty et al. |
| 2018/0186775 A1 | 7/2018 | Vermeulen et al. |
| 2018/0296558 A1 | 10/2018 | Jovcheva et al. |

FOREIGN PATENT DOCUMENTS

| | | |
|---|---|---|
| CN | 1128496 A | 8/1996 |
| CN | 102036963 A | 4/2011 |
| EP | 0544445 A2 | 6/1993 |
| EP | 1001946 | 5/2000 |
| EP | 1659175 A1 | 5/2006 |
| EP | 1208231 B1 | 1/2007 |
| EP | 1964837 A1 | 9/2008 |
| EP | 1990342 | 11/2008 |
| EP | 2332939 | 6/2011 |
| EP | 2650293 A1 | 10/2013 |
| EP | 3027210 A1 | 6/2016 |
| EP | 3177321 A1 | 6/2017 |
| EP | 3179992 A1 | 6/2017 |
| JP | 2003213463 A | 7/2003 |
| JP | 2006516561 A | 7/2006 |
| JP | 2008530030 A | 8/2008 |
| JP | 2008540535 A | 11/2008 |
| JP | 2010514693 A | 5/2010 |
| RU | 2377241 C2 | 12/2009 |
| WO | 94/26723 A2 | 11/1994 |
| WO | 95/19169 A2 | 7/1995 |
| WO | 98/54156 A1 | 12/1998 |
| WO | 99/17759 A2 | 4/1999 |
| WO | 00/42026 A1 | 7/2000 |
| WO | 01/19825 A1 | 2/2001 |
| WO | 01/68047 A2 | 9/2001 |
| WO | 02/076985 A1 | 10/2002 |
| WO | 03/051833 A2 | 6/2003 |
| WO | 03/055491 A1 | 7/2003 |
| WO | 03/086394 A1 | 10/2003 |
| WO | 2004/006355 A2 | 1/2004 |
| WO | 2004/030635 A2 | 4/2004 |
| WO | 2004/043950 A1 | 5/2004 |
| WO | 2004/056822 A1 | 7/2004 |
| WO | 2004065378 A1 | 8/2004 |
| WO | 2004/098494 A2 | 11/2004 |
| WO | 2004/110350 A2 | 12/2004 |
| WO | 2005/007099 A2 | 1/2005 |
| WO | 2005/009437 A1 | 2/2005 |
| WO | 2005/012288 A1 | 2/2005 |
| WO | 2005/039587 A1 | 5/2005 |
| WO | 2005/047244 A2 | 5/2005 |
| WO | 2005/054201 A1 | 6/2005 |
| WO | 2005054231 A1 | 6/2005 |
| WO | 2005/061463 A1 | 7/2005 |
| WO | 2006/040052 A1 | 4/2006 |
| WO | 2006/066361 A1 | 6/2006 |
| WO | 2006084338 A1 | 8/2006 |
| WO | 2006/092430 A1 | 9/2006 |
| WO | 2006121168 A1 | 11/2006 |
| WO | 2006/124354 A2 | 11/2006 |
| WO | 2007/003419 A1 | 1/2007 |
| WO | 2007/005874 A2 | 1/2007 |
| WO | 2007/023186 A1 | 3/2007 |
| WO | 2007/054556 A1 | 5/2007 |
| WO | 2007/075567 A1 | 7/2007 |
| WO | 2007/125405 A2 | 11/2007 |
| WO | 2007/132227 A1 | 11/2007 |
| WO | 2008/003702 A2 | 1/2008 |
| WO | 2008060907 A2 | 5/2008 |
| WO | 2008/076278 A1 | 6/2008 |
| WO | 2008/078091 A1 | 7/2008 |
| WO | 2008/082198 A1 | 7/2008 |
| WO | 2008079988 A2 | 7/2008 |
| WO | 2008080015 A2 | 7/2008 |
| WO | 2008109465 A2 | 9/2008 |
| WO | 2008112408 A1 | 9/2008 |
| WO | 2008/138878 A2 | 11/2008 |
| WO | 2008/141065 A1 | 11/2008 |
| WO | 2008/148867 A2 | 12/2008 |
| WO | 2008/150827 A1 | 12/2008 |
| WO | 2008/155378 A1 | 12/2008 |
| WO | 2009/019518 A1 | 2/2009 |
| WO | 2009/021083 A1 | 2/2009 |
| WO | 2009020990 A1 | 2/2009 |
| WO | 2009/064835 A1 | 5/2009 |
| WO | 2009/137378 A1 | 11/2009 |
| WO | 2009/141386 A1 | 11/2009 |
| WO | 2010059771 A1 | 5/2010 |
| WO | 2010/084152 A1 | 7/2010 |
| WO | 2010088177 A1 | 8/2010 |
| WO | 2010/129570 A1 | 11/2010 |
| WO | 2011/026579 A1 | 3/2011 |

(56) References Cited

FOREIGN PATENT DOCUMENTS

| | | |
|---|---|---|
| WO | 2011/028947 A2 | 3/2011 |
| WO | 2011/064250 A1 | 6/2011 |
| WO | 2011/126903 A2 | 10/2011 |
| WO | 2011/135376 A1 | 11/2011 |
| WO | 2011/146591 A1 | 11/2011 |
| WO | 2011/149937 A1 | 12/2011 |
| WO | 2012/073017 A1 | 6/2012 |
| WO | 2012/104776 A1 | 8/2012 |
| WO | 2012106556 A2 | 8/2012 |
| WO | 2012/118492 A1 | 9/2012 |
| WO | 2012/148540 A1 | 11/2012 |
| WO | 2013019906 A1 | 2/2013 |
| WO | 2013/032951 A1 | 3/2013 |
| WO | 2013/040515 A1 | 3/2013 |
| WO | 2013/043935 A1 | 3/2013 |
| WO | 2013/052699 A2 | 4/2013 |
| WO | 2013/061074 A1 | 5/2013 |
| WO | 2013/061077 A1 | 5/2013 |
| WO | 2013/061080 A1 | 5/2013 |
| WO | 2013/061081 A1 | 5/2013 |
| WO | 2013/061305 A1 | 5/2013 |
| WO | 2013/063217 A1 | 5/2013 |
| WO | 2013076186 A1 | 5/2013 |
| WO | 2013087725 A1 | 6/2013 |
| WO | 2013089882 A2 | 6/2013 |
| WO | 2013133351 A1 | 9/2013 |
| WO | 2013173485 A1 | 11/2013 |
| WO | 2013/179033 A1 | 12/2013 |
| WO | 2013/179034 A1 | 12/2013 |
| WO | 2014007369 A1 | 1/2014 |
| WO | 2014018673 A2 | 1/2014 |
| WO | 2014018841 A1 | 1/2014 |
| WO | 2014051022 A1 | 4/2014 |
| WO | 2014071419 A2 | 5/2014 |
| WO | 2014113729 A2 | 7/2014 |
| WO | 2014/165422 A1 | 10/2014 |
| WO | 2014/174307 A1 | 10/2014 |
| WO | 2014165710 A2 | 10/2014 |
| WO | 2014193229 A2 | 12/2014 |
| WO | 2015/016718 A1 | 2/2015 |
| WO | 2015017607 A2 | 2/2015 |
| WO | 2015/077717 A1 | 5/2015 |
| WO | 2015/100257 A1 | 7/2015 |
| WO | 2015/112900 A1 | 7/2015 |
| WO | 2015144803 A1 | 10/2015 |
| WO | 2015144804 A1 | 10/2015 |
| WO | 2015144808 A1 | 10/2015 |
| WO | 2016/004218 A1 | 1/2016 |
| WO | 2016/004875 A1 | 1/2016 |
| WO | 2016/019472 A1 | 2/2016 |
| WO | 2016/024228 A1 | 2/2016 |
| WO | 2016/024231 A1 | 2/2016 |
| WO | 2016/040880 A1 | 3/2016 |
| WO | 2016/040882 A1 | 3/2016 |
| WO | 2016/044207 A1 | 3/2016 |
| WO | 2016048833 A2 | 3/2016 |
| WO | 2016/054555 A2 | 4/2016 |
| WO | 2016/061142 A1 | 4/2016 |
| WO | 2016/065409 A1 | 5/2016 |
| WO | 2016/094309 A1 | 6/2016 |
| WO | 2016/100882 A1 | 6/2016 |
| WO | 2016/118654 A1 | 7/2016 |
| WO | 2016/128912 A1 | 8/2016 |
| WO | 2016128411 A1 | 8/2016 |
| WO | 2016134234 A1 | 8/2016 |
| WO | 2016/137850 A1 | 9/2016 |
| WO | 2016/140717 A1 | 9/2016 |
| WO | 2016/141209 A1 | 9/2016 |
| WO | 2016/141218 A1 | 9/2016 |
| WO | 2016/153839 A1 | 9/2016 |
| WO | 2016/154068 A1 | 9/2016 |
| WO | 2016/154473 A1 | 9/2016 |
| WO | 2016/161239 A1 | 10/2016 |
| WO | 2016/168716 A1 | 10/2016 |
| WO | 2016/191751 A1 | 12/2016 |
| WO | 2016/196389 A1 | 12/2016 |
| WO | 2016/201425 A1 | 12/2016 |
| WO | 2016/210108 A1 | 12/2016 |
| WO | 2017/004192 A1 | 1/2017 |
| WO | 2017/013436 A1 | 1/2017 |
| WO | 2017/046746 A1 | 3/2017 |
| WO | 2017/091577 A1 | 6/2017 |
| WO | 2017/091580 A1 | 6/2017 |
| WO | 2017/093942 A1 | 6/2017 |

OTHER PUBLICATIONS

Thompson, A.M., et al. "Synthesis and Structure—Activity Relationships of 7-Substituted 3-(2,6-Dichlorophenyl)-1,6-napthyridin-2(1H)-ones as Selective Inhibitors of pp60$^{c\text{-}src}$", *Journal of Medicinal Chemistry*, vol. 43, No. 16, 2000, pp. 3134-3147.

Berge, S.M., et al. "Pharmaceutical Salts", *Journal of Pharmaceutical Sciences*, vol. 66, No. 1, 1977, pp. 1-19.

Deady, L.W. "Ring Nitrogen Oxidation of Amino Substituted Nitrogen Heterocycles with m-Chloroperbenzoic Acid", *Synthetic Communications*, vol. 7(8), 1977, pp. 509-514.

Knights, V., et al. "De-regulated FGF receptors as therapeutic targets in cancer", *Pharmacology & Therapeutics*, 2010; vol. 125(1), pp. 105-117.

Korc, M., et al. "The Role of Fibroblast Growth Factors in Tumor Growth", *Current Cancer Drug Targets*, vol. 9(5), 2009, pp. 639-651.

Angerer, L.M., et al. "Demonstration of Tissue-Specific Gene Expression by in Situ Hybridization", *Methods in Enzymology*, vol. 152, 1987, pp. 649-661.

Deprimo, S.E., et al. "Expression profiling of blood samples from an SU5416 Phase III metastatic colorectal cancer clinical trial: a novel strategy for biomarker identification", *BMC Cancer*, vol. 3, 2003; pp. 1-12.

Orre, M., et al., "VEGF, VEGFR-1, VEGFR-2, Microvessel Density and Endothelial Cell Proliferation in Tumours of the Ovary", *Int. J. Cancer (Pred. Oncol.)*, vol. 84(2), 1999, pp. 101-108.

Zhou, W., et al., "A Structure-Guided Approach to Creating Covalent FGFR Inhibitors", *Chemistry & Biology*, vol. 17, pp. 285-295 (2010).

Avendaño, C., et al., "Drugs That Inhibit Signalling Pathways for Tumor Cell Growth and Proliferation", *Medicinal Chemistry of Anticancer Drugs*, pp. 251-305 (2008).

Garuti, L., et al., Irreversible Protein Kinase Inhibitors, *Current Medicinal Chemistry*, vol. 18, No. 20, Jul. 1, 2011, pp. 2981-2994.

Vippagunta, S.R. et al., "Crystalline Solids", *Advanced Drug Delivery Reviews*, vol. 48, pp. 3-26 (2001).

Jordan, V.C., "Tamoxifen: A Most Unlikely Pioneering Medicine", *Nature Reviews: Drug Discovery*, vol. 2, pp. 205-213 (2003).

Hackam, D.G., et al., "Translation of Research Evidence From Animals to Humans", *JAMA*, vol. 14, pp. 1731-1732 (2006).

"Himicheskaja jenciklopedija" tom 4, str. 990-993, izdatel'stvo "Sovetskaja jencklopedija", Moskva, 1988 (In English: Chemical Encyclopedia, vol. 4, pp. 990-993, Publishing House "Soviet encyclopedia", Moscow, 1988).

V. Hikkinvottom, "Reakcii Organicheskih Soedinenij" Gosudarstvennoe ob#eninennoe nauchno-technicheskoe izdatel'stvo, Redakcija himicheskoj literatury, Moskva, stranicy 360-362, 1939 (In English: V. Hikkinbottom, "Reactions of Organic Compounds", State Associated Scientific-Technical Publishing House, Editor Office of Chemical Literature, pp. 360-362, Moscow, 1939).

"Himicheskaja jenciklopedija" tom. 1, stranicy 242-243, izdatel'stvo "Sovetskaja jencklopedija", Moskva, 1988 (In English: Chemical Encyclopedia (thesaurus), vol. 1, pp. 242-243, publishing house "Soviet encyclopedia", Moscow, 1988).

Dorwald, F.Z., "Side Reactions in Organic Synthesis: A Guide to Successful Synthesis Design", Weinheim:WILEY-VCH Verlag GmbH & Co. KGaA, 2005, ISBN: 3-527-31021.5.

Lima, L.M., et al., "Bioisosterism: A Useful Strategy for Molecular Modification and Drug Design", *Current Medical Chemistry*, vol. 12(1), pp. 23-49 (2005).

Patani, G.A., et al., "Bioisosterism: A Rational Approach in Drug Design", *Chem. Rev.* vol. 96, pp. 3147-3176 (1996).

(56) References Cited

OTHER PUBLICATIONS

Dieci, M.V., et al., "Fibroblast Growth Factor Receptor Inhibitors as a Cancer Treatment: From a Biologic Rationale to Medical Perspectives", *Cancer Discovery*, vol. 3, No. 3, pp. 264-279 (Feb. 2013).
Gallick, G.E., et al., "Small-molecule protein tyrosine kinase inhibitors for the treatment of metastatic prostate cancer", *Future Medicinal Chemistry*, vol. 4, No. 1, pp. 107-119 (Jan. 2012).
Study to Assess the Relative Bioavailability of Orally Administered JNJ-42756493 Tablet Versus JNJ-42756493 Capsule in Healthy Participants, ClinicalTrials.gov, pp. 1-4 (2014).
Matsuda, Y., et al., "Fibroblast Growth Factor Receptor-2 IIIc as a Novel Molecular Target in Colorectal Cancer", *Current Colorectal Cancer Reports*, vol. 10, No. 1, pp. 20-26 (2014).
Carneiro, B.A., et al., "Emerging therapeutic targets in bladder cancer", *Cancer Treatment Reviews*, vol. 41, No. 2, pp. 170-178 (2015).
Fujita, M., et al., "Generation of Formaldehyde by Pharmaceutical Excipients and Its Absorption by Meglumine", *Chem. Pharm. Bull*, vol. 57, No. 10, pp. 1096-1099 (2009).
Adcock, J., et al., "Diversity oriented synthesis: substitution at C5 in unreactive pyrimidines by Claisen rearrangement and reactivity in nucleophilic substitution at C2 and C4 in pteridines and pyrido[2,3-d]pyrimidines", *Tetrahedron*, vol. 67, pp. 3226-3237 (2011).
Database Caplus, Grina, et al., "Preparation of oxohydroquinazolinylaminophenylpropanesulfonamide derivatives and analogs for use as Raf inhibitors", Document No. 157:465574, Accession No. 2012:1301209 (2012).
Liang, G., et al., "Small molecule inhibition of fibroblast growth factor receptors in cancer", *Cytokine & Growth Factor Reviews*, vol. 24, pp. 467-475 (2013).
Golub, T.R., et al., "Molecular Classification of Cancer: Class Discovery and Class Prediction by Gene Expression Monitoring", *Science*, vol. 286, pp. 531-537 (1999).
Greulich, H., et al., "Targeting mutant fibroblast growth factor receptors in cancer", *Trends in Molecular Medicine*, vol. 17, No. 5, pp. 283-292 (2011).
Freshney, R.I., "Culture of Animal Cells, A Manual of Basic Technique", Published by Alan R. Liss, Inc, New York, pp. 1-6 (1983).
Cohen, P., "The development and therapeutic potential of protein kinase inhibitors", *Current Opinion in Chemical Biology*, vol. 3, pp. 459-465 (1999).
Cecil Textbook of Medicine, edited by Bennet, J.C., and Plum, F., 20th edition, vol. 1, pp. 1004-1010 (1996).
Hynes, N.E., et al., "Potential for Targeting the Fibroblast Growth Factor Receptors in Breast Cancer", *Cancer Research*, vol. 70, pp. 5199-5202 (2010).
Neidle, S., "Cancer Drug Design and Discovery", Elsevier/Academic Press, pp. 427-431 (2008).
Dermer, G.B., "Another Anniversary for the War on Cancer", *Biotechnology*, vol. 12, p. 320 (1994).
Katoh, Y., et al., "FGFR2-related pathogenesis and FGFR2-targeted therapeutics (Review)", *International Journal of Molecular Medicine*, vol. 23, pp. 307-311 (2009).
Jain, V.K., et al., "Challenges and opportunities in the targeting of fibroblast growth factor receptors in breast cancer", *Breast Cancer Research*, vol. 14, No. 208, pp. 1-9 (2012).
Sonpavde, G., et al., "Fibroblast growth factor receptors as therapeutic targets in clear-cell renal cell carcinoma", *Expert Opinion on Investigational Drugs*, vol. 23, Issue 3, pp. 305-315 (2014).
Rodriguez-Vida, A., et al., "Complexity of FGFR signaling in metastatic urothelial cancer," *Journal of Hematology & Oncology*, vol. 8, No., pp. 119 et seq. (2015).
Angibaud et al., "Discovery of JNJ-42756493, A Potent Fibroblast Growth Factor Receptor (FGFR) Inhibitor Using a Fragment Based Approach," AACR Minisymposium, Small Molecule Design and Optimization San Diego, CA, Apr. 8, 2014, 16 pp.

Bronte et al., "Nintedanib in NSCLC: Evidence to Date and Place in Therapy," Therapeutic Advances in Medical Oncology, 2016, vol. 8[3], pp. 188-197.
Kathoh et al., "FGFR inhibitors: Effects on Cancer Cells, Tumor Microenvironment and Whole-Body Homeostasis (Review)," International Journal of Molecular Medicine 2016, 38(1), pp. 3-15.
D.A.Kharkevich, Farmakologiya (Pharmacology), 1996, M., Meditsina, p. 41, chapter 6.A (in Russian Only).
V.G.Belikov, Farmatsevticheskaya khimiya (Pharmaceutical Chemistry), M., Vysshaya shkola, 1993, p. 1, chapter 2.2, pp. 43-47) (in Russian only).
Amin et al., "Nivolumab (anti-PD-1; BMS-936558, ONO-4538) in combination with sunitinib or pazopanib in patients (pts) with metastic renal cell carcinoma (mRCC)," Journal of Clinical Oncology 2014, vol. 32:15.
Phillips et al., "Therapeutic Uses of Anti-PD-1 and anti-PD-L1 Antibodies," International Immunology, Oct. 2014, vol. 27, No. 1, pp. 39-46.
Dienstmann et al., "Genomic Aberrations in the FGFR Pathway: Opportunities for Targeted Therapies in Solid Tumors," Annals of Oncology, vol. 25, Nov. 20, 2013, No. 3, pp. 552-563.
Parker et al., "Emergence of FGFR Family Gene Fusions as Therapeutic Targets in a Wide Spectrum of Solid Tumours," Journal of Pathology, Oct. 29, 2013, vol. 232, No. 1, pp. 4-15.
Arai et al., "Fibroblast Growth Factor Receptor 2 Tyrosine Kinase Fusions Define a Unique Molecular Subtype of Cholangiocarcinoma," Hepatology, Apr. 2014, vol. 59, No. 4, pp. 1427-1434.
Bahleda et al., "Phase 1 Study of JNJ-42756493, a Pan-Fibroblast Growth Factor Receptor (FGFR) Inhibitor, in patients with advanced Solid Tumors," Journal of Clinical Oncology, May 2014, vol. 32, No. 15, pp. 2501-2501.
Di Siefano et al., "Detection, Characterization, and Inhibition of FGFR-TACC Fusions in IDH Wild-Type Glioma," Clinical Cancer Research, Jan. 21, 2015, vol. 21, No. 14, pp. 3307-3317.
Parker, B.C., et al., "The tumorigenic FGFR3-TACC3 gene fusion escapes miR-99a regulation in glioblastoma," *The Journal of Clinical Investigation*, 123 (2), pp. 855-865, Feb. 1, 2013.
Bello, et al., "E=3810 is a Potent Dual Inhibitor of VEGFR and FGFR that Exerts Antitumor Activity in Multiple Preclinical Models," vol. 71(4), pp. 1396-1405 (2011).
Database, Geneseq [Online], "FGFR3-TACC3 gene fusion PCR primer, FGFR3-TACC3(F18T11)_qPCR_F SEQ: 15," XP002753027, Database accession No. BAT14432 (2013).
Database, Geneseq [Online], "Human FGFR 2 mRNA target sequence for mdRNA, SEQ ID:3954," XP055257043, Database accession no. ATM46802 (2008).
Gavine, et al., "AZD4547: An Orally Bioavailable, Potent, and Selective Inhibitor of the Fibroblast Growth Factor Receptor Tyrosine Kinase Family," *Cancer Research*, vol. 72(8), pp. 2045-2056 (2012).
International Search Report from PCT/US2015/050996 dated Mar. 23, 2016.
Mengual, et al., BMC Research Notes 1:21, pp. 1-8 (Jun. 2008).
Millholland, et al., Research and Reports in Urology, 4: 33-40 (2012).
Sabnis, et al., "FGFR Fusions in the Driver's Seat," *Cancer Discovery*, vol. 3 (6), pp. 607-609 (2013).
Shinmura, et al., "A novel somatic FGFR3 mutation in primary lung cancer," *Oncology Reports*, vol. 31 (3), pp. (2014).
Singh, et al., "Transforming Fusions of FGFR and TACC Genes in Human Glioblastoma, " *Science*, vol. 337 (6099), pp. 1231-1235 (2012).
Trudel, et al., "Evaluation of XL999, a Potent Inhibitor of FGFR3, for the Potential Treatment of t(4;14) Positive Multiple Myeloma, " *Blood*, vol. 110 (11), pp. 741A-742A (2007).
Williams, et al., "Oncogenic FGFR3 gene fusions in bladder cancer," *Human Molecular Genetics*, vol. 22 (4), (2013). pp. 795-803.
Wu, et al., "Identification of Targetable FGFR Gene Fusions in Diverse Cancers," Cancer Discovery, vol. 3 (6), pp. 636-647 (2013).

\* cited by examiner

SEQUENCE LISTING

<160> NUMBER OF SEQ ID NOS: 27

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gacctggacc gtgtccttac c                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cttccccagt tccaggttct t                                              21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aggacctgga ccgtgtcctt                                                20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tataggtccg gtggacaggg                                                20

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggccatcctg ccccc                                                     15

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gagcagtcca ggtcagccag                                                20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 7
ctggaccgtg tccttaccgt                                            20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 8
gcagcccagg attgaactgt                                            20

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 9
tggatcgaat tctcactctc aca                                        23

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 10
gccaagcaat ctgcgtattt g                                          21

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 11
tggtagaaga cttggatcga attct                                      25

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 12
tctcccggat tatttcttca aca                                        23

```
<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gctcttcaat acagccctga tca                                              23

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
acttggatcg aattctcact ctca                                             24

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tggatcgaat tctcactctc aca                                              23

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcaaagcctg aattttcttg aataa                                            25

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agggtgcatc aactcatgaa ttag                                             24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
acttggatcg aattctcact ctca                                             24
```

<210> SEQ ID NO 19
<211> LENGTH: 2850
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

| | | | | | |
|---|---|---|---|---|---|
| atgggcgccc | ctgcctgcgc | cctcgcgctc | tgcgtggccg | tggccatcgt | ggccggcgcc | 60 |
| tcctcggagt | ccttggggac | ggagcagcgc | gtcgtggggc | gagcggcaga | agtcccgggc | 120 |
| ccagagcccg | ccagcagga | gcagttggtc | ttcggcagcg | gggatgctgt | ggagctgagc | 180 |
| tgtcccccgc | ccggggtgg | tcccatgggg | cccactgtct | gggtcaagga | tggcacaggg | 240 |
| ctggtgccct | cggagcgtgt | cctggtgggg | ccccagcggc | tgcaggtgct | gaatgcctcc | 300 |
| cacgaggact | ccggggccta | cagctgccgg | cagcggctca | cgcagcgcgt | actgtgccac | 360 |
| ttcagtgtgc | gggtgacaga | cgctccatcc | tcgggagatg | acgaagacgg | ggaggacgag | 420 |
| gctgaggaca | caggtgtgga | cacaggggcc | ccttactgga | cacggcccga | gcggatggac | 480 |
| aagaagctgc | tggccgtgcc | ggccgccaac | accgtccgct | ccgctgccc | agccgctggc | 540 |
| aaccccactc | cctccatctc | ctggctgaag | aacggcaggg | agttccgcgg | cgagcaccgc | 600 |
| attggaggca | tcaagctgcg | gcatcagcag | tggagcctgg | tcatggaaag | cgtggtgccc | 660 |
| tcggaccgcg | gcaactacac | ctgcgtcgtg | agaaacaagt | tggcagcat | ccggcagacg | 720 |
| tacacgctgg | acgtgctgga | gcgctccccg | caccggccca | tcctgcaggc | ggggctgccg | 780 |
| gccaaccaga | cggcggtgct | gggcagcgac | gtggagttcc | actgcaaggt | gtacagtgac | 840 |
| gcacagcccc | acatccagtg | gctcaagcac | gtggaggtga | atggcagcaa | ggtgggcccg | 900 |
| gacggcacac | cctacgttac | cgtgctcaag | acggcgggcg | ctaacaccac | cgacaaggag | 960 |
| ctagaggttc | tctccttgca | caacgtcacc | tttgaggacg | ccggggagta | cacctgcctg | 1020 |
| gcgggcaatt | ctattgggtt | ttctcatcac | tctgcgtggc | tggtggtgct | gccagccgag | 1080 |
| gaggagctgg | tggaggctga | cgaggcgggc | agtgtgtatg | caggcatcct | cagctacggg | 1140 |
| gtgggcttct | tcctgttcat | cctggtggtg | cggctgtga | cgctctgccg | cctgcgcagc | 1200 |
| ccccccaaga | aaggcctggg | ctcccccacc | gtgcacaaga | tctcccgctt | cccgctcaag | 1260 |
| cgacaggtgt | ccctggagtc | caacgcgtcc | atgagctcca | acacaccact | ggtgcgcatc | 1320 |
| gcaaggctgt | cctcagggga | gggccccacg | ctggccaatg | tctccgagct | cgagctgcct | 1380 |
| gccgacccca | aatgggagct | gtctcgggcc | cggctgaccc | tggcaagcc | ccttggggag | 1440 |
| ggctgcttcg | gccaggtggt | catggcggag | gccatcggca | ttgacaagga | ccgggccgcc | 1500 |
| aagcctgtca | ccgtagccgt | gaagatgctg | aaagacgatg | ccactgacaa | ggacctgtcg | 1560 |
| gacctggtgt | ctgagatgga | gatgatgaag | atgatcggga | aacacaaaaa | catcatcaac | 1620 |
| ctgctgggcg | cctgcacgca | gggcgggccc | ctgtacgtgc | tggtggagta | cgcggccaag | 1680 |
| ggtaacctgc | gggagtttct | gcgggcgcgg | cggcccccgg | gcctggacta | ctccttcgac | 1740 |
| acctgcaagc | cgcccgagga | gcagctcacc | ttcaaggacc | tggtgtcctg | tgcctaccag | 1800 |
| gtggcccggg | gcatggagta | cttggcctcc | cagaagtgca | tccacaggga | cctggctgcc | 1860 |
| cgcaatgtgc | tggtgaccga | ggacaacgtg | atgaagatcg | cagacttcgg | gctggcccgg | 1920 |
| gacgtgcaca | acctcgacta | ctacaagaag | acgaccaacg | gccggctgcc | cgtgaagtgg | 1980 |
| atggcgcctg | aggccttgtt | tgaccgagtc | tacactcacc | agagtgacgt | ctggtccttt | 2040 |
| ggggtcctgc | tctgggagat | cttcacgctg | gggggctccc | cgtaccccgg | catccctgtg | 2100 |

```
gaggagctct tcaagctgct gaaggagggc caccgcatgg acaagcccgc caactgcaca    2160
cacgacctgt acatgatcat gcgggagtgc tggcatgccg cgccctccca gaggcccacc    2220
ttcaagcagc tggtggagga cctggaccgt gtccttaccg tgacgtccac cgacgtaaag    2280
gcgacacagg aggagaaccg ggagctgagg agcaggtgtg aggagctcca cgggaagaac    2340
ctggaactgg ggaagatcat ggacaggttc gaagaggttg tgtaccaggc catggaggaa    2400
gttcagaagc agaaggaact ttccaaagct gaaatccaga agttctaaa agaaaaagac    2460 caacttacca cagatctgaa ctccatggag aagtccttct ccgacctctt caagcgtttt    2520
gagaaacaga aagaggtgat cgagggctac cgcaagaacg aagagtcact gaagaagtgc    2580
gtggaggatt acctggcaag gatcacccag gagggccaga ggtaccaagc cctgaaggcc    2640
cacgcggagg agaagctgca gctggcaaac gaggagatcg cccaggtccg gagcaaggcc    2700
caggcggaag cgttggccct ccaggccagc ctgaggaagg agcagatgcg catccagtcg    2760
ctggagaaga cagtggagca gaagactaaa gagaacgagg agctgaccag gatctgcgac    2820
gacctcatct ccaagatgga gaagatctga                                     2850
```

<210> SEQ ID NO 20
<211> LENGTH: 2955
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
atgggcgccc ctgcctgcgc cctcgcgctc tgcgtggccg tggccatcgt ggccggcgcc      60
tcctcggagt ccttggggac ggagcagcgc gtcgtggggc gagcggcaga agtcccgggc     120
ccagagcccg ccagcagga gcagttggtc ttcggcagcg gggatgctgt ggagctgagc     180
tgtcccccgc ccgggggtgg tcccatgggg cccactgtct gggtcaagga tggcacaggg     240
ctggtgccct cggagcgtgt cctggtgggg cccagcggc tgcaggtgct gaatgcctcc     300
cacgaggact ccggggccta cagctgccgg cagcggctca cgcagcgcgt actgtgccac     360
ttcagtgtgc gggtgacaga cgctccatcc tcgggagatg acgaagacgg ggaggacgag     420
gctgaggaca caggtgtgga cacaggggcc ccttactgga cacggcccga gcggatggac     480
aagaagctgc tggccgtgcc ggccgccaac accgtccgct tccgctgccc agccgctggc     540
aaccccactc cctccatctc ctggctgaag aacggcaggg agttccgcgg cgagcaccgc     600
attggaggca tcaagctgcg gcatcagcag tggagcctgg tcatggaaag cgtggtgccc     660
tcggaccgcg gcaactacac ctgcgtcgtg gagaacaagt ttggcagcat ccggcagacg     720
tacacgctgg acgtgctgga gcgctccccg caccggccca tcctgcaggc ggggctgccg     780
gccaaccaga cggcggtgct gggcagcgac gtggagttcc actgcaaggt gtacagtgac     840
gcacagcccc acatccagtg gctcaagcac gtggaggtga atggcagcaa ggtgggcccg     900
gacggcacac cctacgttac cgtgctcaag acggcgggcg ctaacaccac cgacaaggag     960
ctagaggttc tctccttgca caacgtcacc tttgaggacg ccggggagta cacctgcctg    1020
gcgggcaatt ctattgggtt ttctcatcac tctgcgtggc tggtggtgct gccagccgag    1080
gaggagctgg tggaggctga cgaggcgggc agtgtgtatg caggcatcct cagctacggg    1140
gtgggcttct tcctgttcat cctggtggtg gcggctgtga cgctctgccg cctgcgcagc    1200
ccccccaaga aaggcctggg ctcccccacc gtgcacaaga tctcccgctt cccgctcaag    1260
```

```
cgacaggtgt ccctggagtc caacgcgtcc atgagctcca acacaccact ggtgcgcatc      1320
gcaaggctgt cctcagggga gggccccacg ctggccaatg tctccgagct cgagctgcct      1380
gccgacccca atgggagct gtctcgggcc cggctgaccc tgggcaagcc ccttggggag       1440
ggctgcttcg gccaggtggt catggcgag gccatcggca ttgacaagga ccgggccgcc       1500
aagcctgtca ccgtagccgt gaagatgctg aaagacgatg ccactgacaa ggacctgtcg      1560
gacctggtgt ctgagatgga gatgatgaag atgatcggga acacaaaaa catcatcaac      1620 ctgctgggcg cctgcacgca gggcgggccc ctgtacgtgc tggtggagta cgcggccaag      1680
ggtaacctgc gggagtttct gcgggcgcgg cggcccccgg gcctggacta ctccttcgac      1740
acctgcaagc cgcccgagga gcagctcacc ttcaaggacc tggtgtcctg tgcctaccag      1800
gtggcccggg gcatggagta cttggcctcc agaagtgca tccacaggga cctggctgcc       1860
cgcaatgtgc tggtgaccga ggacaacgtg atgaagatcg cagacttcgg gctggcccgg      1920
gacgtgcaca acctcgacta ctacaagaag acgaccaacg gccggctgcc cgtgaagtgg      1980
atggcgcctg aggccttgtt tgaccgagtc tacactcacc agagtgacgt ctggtccttt      2040
ggggtcctgc tctgggagat cttcacgctg ggggctccc cgtaccccgg catccctgtg       2100
gaggagctct tcaagctgct gaaggagggc caccgcatgg acaagcccgc caactgcaca      2160
cacgacctgt acatgatcat gcgggagtgc tggcatgccg cgccctccca gaggcccacc      2220
ttcaagcagc tggtggagga cctggaccgt gtccttaccg tgacgtccac cgacgtgcca      2280
ggcccacccc caggtgttcc cgcgcctggg ggcccacccc tgtccaccgg acctatagtg      2340
gacctgctcc agtacagcca gaaggacctg gatgcagtgg taaaggcgac acaggaggag      2400
aaccgggagc tgaggagcag gtgtgaggag ctccacggga agaacctgga actggggaag      2460
atcatggaca ggttcgaaga ggttgtgtac caggccatgg aggaagttca gaagcagaag      2520
gaactttcca aagctgaaat ccagaaagtt ctaaaagaaa aagaccaact taccacagat      2580
ctgaactcca tggagaagtc cttctccgac ctcttcaagc gttttgagaa acagaaagag      2640
gtgatcgagg gctaccgcaa gaacgaagag tcactgaaga agtgcgtgga ggattacctg      2700
gcaaggatca cccaggaggg ccagaggtac caagccctga ggcccacgc ggaggagaag      2760 ctgcagctgg caaacgagga gatcgcccag gtccggagca aggcccaggc ggaagcgttg      2820
gccctccagg ccagcctgag gaaggagcag atgcgcatcc agtcgctgga agagacagtg      2880
gagcagaaga ctaaagagaa cgaggagctg accaggatct gcgacgacct catctccaag      2940
atggagaaga tctga                                                      2955
```

<210> SEQ ID NO 21
<211> LENGTH: 4462
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21

```
atgggcgccc ctgcctgcgc cctcgcgctc tgcgtggccg tggccatcgt ggccggcgcc        60
tcctcggagt ccttggggac ggagcagcgc gtcgtggggc gagcggcaga agtcccgggc       120
ccagagcccg gccagcagga gcagttggtt ttcggcagcg gggatgctgt ggagctgagc       180 tgtccccgc cggggggtgg tcccatgggg cccactgtct gggtcaagga tggcacaggg       240
ctggtgccct cggagcgtgt cctggtgggg ccccagcggc tgcaggtgct gaatgcctcc       300
```

```
cacgaggact ccggggccta cagctgccgg cagcggctca cgcagcgcgt actgtgccac      360
ttcagtgtgc gggtgacaga cgctccatcc tcgggagatg acgaagacgg ggaggacgag      420
gctgaggaca caggtgtgga cacagggggcc ccttactgga cacggcccga gcggatggac     480
aagaagctgc tggccgtgcc ggccgccaac accgtccgct tccgctgccc agccgctggc      540
aaccccactc cctccatctc ctggctgaag aacggcaggg agttccgcgg cgagcaccgc      600
attggaggca tcaagctgcg gcatcagcag tggagcctgg tcatggaaag cgtggtgccc      660
tcggaccgcg gcaactacac ctgcgtcgtg gagaacaagt ttggcagcat ccggcagacg      720
tacacgctgg acgtgctgga gcgctccccg caccggccca tcctgcaggc ggggctgccg      780
gccaaccaga cggcggtgct gggcagcgac gtggagttcc actgcaaggt gtacagtgac      840
gcacagcccc acatccagtg gctcaagcac gtggaggtga atggcagcaa ggtgggcccg      900
gacggcacac cctacgttac cgtgctcaag acggcgggcg ctaacaccac cgacaaggag      960
ctagaggttc tctccttgca caacgtcacc tttgaggacg ccggggagta cacctgcctg     1020
gcgggcaatt ctattgggtt ttctcatcac tctgcgtggc tggtggtgct gccagccgag     1080
gaggagctgg tggaggctga cgaggcgggc agtgtgtatg caggcatcct cagctacggg     1140
gtgggcttct tcctgttcat cctggtggtg gcggctgtga cgctctgccg cctgcgcagc     1200 cccccaaga aaggcctggg ctcccccacc gtgcacaaga tctcccgctt cccgctcaag     1260
cgacaggtgt ccctggagtc caacgcgtcc atgagctcca acaccaccact ggtgcgcatc     1320 gcaaggctgt cctcagggga gggccccacg ctggccaatg tctccgagct cgagctgcct     1380 gccgaccca aatgggagct gtctcgggcc cggctgaccc tgggcaagcc ccttggggag     1440
ggctgcttcg ccaggtggt catggcgag ccatcggca ttgacaagga ccgggccgcc        1500
aagcctgtca ccgtagccgt gaagatgctg aaagacgatg ccactgacaa ggacctgtcg     1560
gacctggtgt ctgagatgga gatgatgaag atgatcggga acacaaaaaa catcatcaac     1620
ctgctgggcg cctgcacgca gggcgggccc ctgtacgtgc tggtggagta cgcggccaag     1680
ggtaacctgc gggagtttct gcgggcgcgg cggccccgg gcctggacta ctccttcgac     1740
acctgcaagc cgcccgagga gcagctcacc ttcaaggacc tggtgtcctg tgcctaccag     1800
gtggcccggg gcatggagta cttggcctcc cagaagtgca tccacaggga cctggctgcc     1860
cgcaatgtgc tggtgaccga ggacaacgtg atgaagatcg cagacttcgg gctggcccgg     1920
gacgtgcaca acctcgacta ctacaagaag acgaccaacg gccggctgcc cgtgaagtgg     1980
atggcgcctg aggccttgtt tgaccgagtc tacactcacc agagtgacgt ctggtccttt     2040
ggggtcctgc tctgggagat cttcacgctg ggggctcccc cgtacccggg catccctgtg     2100
gaggagctct tcaagctgct gaaggagggc caccgcatgg acaagcccgc caactgcaca     2160
cacgacctgt acatgatcat gcgggagtgc tggcatgccg cgccctccca gaggcccacc     2220
ttcaagcagc tggtggagga cctggaccgt gtccttaccg tgacgtccac cgacgtgagt     2280
gctggctctg gcctggtgcc acccgcctat gcccctcccc ctgccgtccc cggccatcct     2340
gcccccagga gtgctgaggt gtgggcggg ccttcgctggc ccaggtgccc tggctgacct     2400
ggactgctca agctcttccc agagcccagg aagttctgag aaccaaatgg tgtctccagg     2460
aaaagtgtct ggcagccctg agcaagccgt ggaggaaaac cttagttcct attccttaga     2520
cagaagagtg acacccgcct ctgagaccct agaagaccct tgcaggacag agtcccagca     2580
caaagcggag actccgcacg gagccgagga agaatgcaaa gcggagactc cgcacggagc     2640
```

-continued

```
cgaggaggaa tgccggcacg gtggggtctg tgctcccgca gcagtggcca cttcgcctcc    2700
tggtgcaatc cctaaggaag cctgcggagg agcacccctg cagggtctgc ctggcgaagc    2760
cctgggctgc cctgcgggtg tgggcacccc cgtgccagca gatggcactc agacccttac    2820
ctgtgcacac acctctgctc ctgagagcac agccccaacc aaccacctgg tggctggcag    2880
ggccatgacc ctgagtcctc aggaagaagt ggctgcaggc caaatggcca gctcctcgag    2940
gagcggacct gtaaaactag aatttgatgt atctgatggc gccaccagca aaagggcacc    3000
cccaccaagg agactgggag agaggtccgg cctcaagcct cccttgagga aagcagcagt    3060
gaggcagcaa aaggccccgc aggaggtgga ggaggacgac ggtaggagcg agcaggaga    3120 ggacccccccc atgccagctt ctcggggctc ttaccacctc gactgggaca aaatggatga    3180
cccaaacttc atcccgttcg gaggtgcacac caagtctggt tgcagtgagg cccagcccccc    3240 agaaagccct gagaccaggc tgggccagcc agcggctgaa cagttgcatg ctgggcctgc    3300
cacggaggag ccaggtccct gtctgagcca gcagctgcat tcagcctcag cggaggacac    3360
gcctgtggtg cagttggcag ccgagacccc aacagcagag agcaaggaga gagccttgaa    3420
ctctgccagc acctcgcttc ccacaagctg tccaggcagt gagccagtgc ccacccatca    3480
gcaggggcag cctgccttgg agctgaaaga ggagagcttc agagaccccg ctgaggttct    3540
aggcacgggc gcggaggtgg attacctgga gcagtttgga acttcctcgt ttaaggagtc    3600
ggccttgagg aagcagtcct tatacctcaa gttcgacccc ctcctgaggg acagtcctgg    3660
tagaccagtg cccgtggcca ccgagaccag cagcatgcac ggtgcaaatg agactccctc    3720
aggacgtccg cgggaagcca agcttgtgga gttcgatttc ttgggagcac tggacattcc    3780
tgtgccaggc ccacccccag gtgttcccgc gcctgggggc ccaccccctgt ccaccggacc    3840 tatagtggac ctgctccagt acagccagaa ggacctggat gcagtggtaa aggcgacaca    3900
ggaggagaac cgggagctga ggagcaggtg tgaggagctc cacgggaaga acctggaact    3960
ggggaagatc atggacaggt tcgaagaggt tgtgtaccag gccatggagg aagttcagaa    4020
gcagaaggaa cttttccaaag ctgaaatcca gaaagttcta aaagaaaag accaacttac    4080 cacagatctg aactccatgg agaagtcctt ctccgacctc ttcaagcgtt ttgagaaaca    4140
gaaagaggtg atcgagggct accgcaagaa cgaagagtca ctgaagaagt gcgtggagga    4200
ttacctggca aggatcaccc caggagggcca gaggtaccaa gccctgaagg cccacgcgga    4260
ggagaagctg cagctggcaa cgaggagat cgcccaggtc cggagcaagg cccaggcgga    4320
agcgttggcc ctccaggcca gcctgaggaa ggagcagatg cgcatccagt cgctggagaa    4380
gacagtggag cagaagacta aagagaacga ggagctgacc aggatctgcg acgacctcat    4440
ctccaagatg gagaagatct ga                                             4462
```

<210> SEQ ID NO 22
<211> LENGTH: 3765
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

```
atgggcgccc ctgcctgcgc cctcgcgctc tgcgtggccg tggccatcgt ggccggcgcc      60
tcctcggagt ccttggggac ggagcagcgc gtcgtgggc gagcggcaga agtcccgggc     120
ccagagcccg gccagcagga gcagttggtc ttcggcagcg gggatgctgt ggagctgagc     180
```

```
tgtcccccgc cgggggtgg tcccatgggg cccactgtct gggtcaagga tggcacaggg    240
ctggtgccct cggagcgtgt cctggtgggg ccccagcggc tgcaggtgct gaatgcctcc    300
cacgaggact ccggggccta cagctgccgg cagcggctca cgcagcgcgt actgtgccac    360
ttcagtgtgc gggtgacaga cgctccatcc tcgggagatg acgaagacgg ggaggacgag    420
gctgaggaca caggtgtgga cacaggggcc ccttactgga cacggcccga gcggatggac    480
aagaagctgc tggccgtgcc ggccgccaac accgtccgct ccgctgccc agccgctggc    540
aaccccactc cctccatctc ctggctgaag aacggcaggg agttccgcgg cgagcaccgc    600
attggaggca tcaagctgcg gcatcagcag tggagcctgg tcatggaaag cgtggtgccc    660
tcggaccgcg gcaactacac ctgcgtcgtg gagaacaagt ttggcagcat ccggcagacg    720
tacacgctgg acgtgctgga gcgctccccg caccggccca tcctgcaggc ggggctgccg    780
gccaaccaga cggcggtgct gggcagcgac gtggagttcc actgcaaggt gtacagtgac    840
gcacagcccc acatccagtg gctcaagcac gtggaggtga atggcagcaa ggtgggcccg    900
gacggcacac cctacgttac cgtgctcaag tcctggatca gtgagagtgt ggaggccgac    960
gtgcgcctcc gcctggccaa tgtgtcggag cgggacgggg gcgagtacct ctgtcgagcc   1020
accaatttca taggcgtggc cgagaaggcc ttttggctga cgttcacgg gccccgagca   1080
gccgaggagg agctggtgga ggctgacgag gcgggcagtg tgtatgcagg catcctcagc   1140
tacggggtgg gcttcttcct gttcatcctg gtggtggcgg ctgtgacgct gccgcctg     1200
cgcagccccc ccaagaaagg cctgggctcc ccaccgtgc acaagatctc ccgcttcccg    1260
ctcaagcgac aggtgtccct ggagtccaac gcgtccatga gctccaacac accactggtg   1320
cgcatcgcaa ggctgtcctc aggggagggc cccacgctgg ccaatgtctc cgagctcgag   1380
ctgcctgccg accccaaatg ggagctgtct cgggcccggc tgaccctggg caagcccctt   1440
ggggagggct gcttcggcca gtggtcatg gcggaggcca tcggcattga caaggaccgg    1500
gccgccaagc ctgtcaccgt agccgtgaag atgctgaaag acgatgccac tgacaaggac   1560
ctgtcggacc tggtgtctga gatggagatg atgaagatga tcgggaaaca caaaacatc    1620
atcaacctgc tggcgcctg cacgcagggc gggcccctgt acgtgctggt ggagtacgcg    1680
gccaagggta acctgcggga gtttctgcgg gcgcggcggc ccccgggcct ggactactcc   1740
ttcgacacct gcaagccgcc cgaggagcag ctcaccttca aggacctggt gtcctgtgcc   1800
taccaggtgg cccgggggcat ggagtacttg gcctcccaga agtgcatcca cagggacctg   1860
gctgccgcca atgtgctggt gaccgaggac aacgtgatga gatcgcaga cttcgggctg    1920
gcccgggacg tgcacaacct cgactactac aagaagacga ccaacggccg gctgccgcgtg    1980
aagtggatgg cgcctgaggc cttgtttgac cgagtctaca ctcaccagag tgacgtctgg   2040
tcctttgggg tcctgctctg ggagatcttc acgctggggg gctccccgta ccccggcatc   2100
cctgtggagg agctcttcaa gctgctgaag gagggccacc gcatggacaa gcccgccaac   2160
tgcacacacg acctgtacat gatcatgcgg gagtgctggc atgccgcgcc ctcccagagg   2220
cccaccttca gcagctggt ggaggacctg gaccgtgtcc ttaccgtgac gtccaccgac    2280
aatgttatgg aacagttcaa tcctgggctg cgaaatttaa taaacctggg gaaaaattat    2340
gagaaagctg taaacgctat gatcctggca ggaaaagcct actacgatgg agtggccaag   2400
atcggtgaga ttgccactgg gtcccccgtg tcaactgaac tgggacatgt cctcatagag   2460
atttcaagta cccacaagaa actcaacgag agtcttgatg aaaatttaa aaaattccac   2520
aaagagatta tccatgagct ggagaagaag atagaacttg acgtgaaata tatgaacgca   2580
```

```
actctaaaaa gataccaaac agaacacaag aataaattag agtctttgga gaaatcccaa    2640
gctgagttga agaagatcag aaggaaaagc caaggaagcc gaaacgcact caaatatgaa    2700
cacaaagaaa ttgagtatgt ggagaccgtt acttctcgtc agagtgaaat ccagaaattc    2760
attgcagatg gttgcaaaga ggctctgctt gaagagaaga ggcgcttctg ctttctggtt    2820
gataagcact gtggctttgc aaaccacata cattattatc acttacagtc tgcagaacta    2880
ctgaattcca agctgcctcg gtggcaggag acctgtgttg atgccatcaa agtgccagag    2940
aaaatcatga atatgatcga agaaataaag accccagcct ctaccccgt gtctggaact    3000 cctcaggctt cacccatgat cgagagaagc aatgtggtta ggaaagatta cgacacccct    3060
tctaaatgct caccaaagat gcccccgct ccttcaggca gagcatatac cagtcccttg    3120
atcgatatgt ttaataaccc agccacggct gccccgaatt cacaaagggt aaataattca    3180
acaggtactt ccgaagatcc cagtttacag cgatcagttt cggttgcaac gggactgaac    3240
atgatgaaga agcagaaagt gaagaccatc ttcccgcaca ctgcgggctc caacaagacc    3300
ttactcagct ttgcacaggg agatgtcatc acgctgctca tccccgagga aaggatggc    3360 tggctctatg gagaacacga cgtgtccaag gcgaggggt ggttcccgtc gtcgtacacg    3420
aagttgctgg aagaaaatga gacagaagca gtgaccgtgc ccacgccaag ccccacacca    3480
gtgagaagca tcagcaccgt gaacttgtct gagaatagca gtgttgtcat ccccccaccc    3540
gactacttgg aatgcttgtc catgggggca gctgccgaca ggagagcaga ttcggccagg    3600
acgacatcca cctttaaggc cccagcgtcc aagcccgaga ccgcggctcc taacgatgcc    3660
aacgggactg caaagccgcc ttttctcagc ggagaaaacc cctttgccac tgtgaaactc    3720
cgcccgactg tgacgaatga tcgctcggca cccatcattc gatga                   3765
```

<210> SEQ ID NO 23
<211> LENGTH: 4989
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
atggtcagct ggggtcgttt catctgcctg gtcgtggtca ccatggcaac cttgtccctg     60
gcccggccct ccttcagttt agttgaggat accacattag agccagaaga gccaccaacc    120
aaataccaaa tctctcaacc agaagtgtac gtggctgcgc caggggagtc gctagaggtg    180
cgctgcctgt tgaaagatgc cgccgtgatc agttggacta aggatggggt gcacttgggg    240
cccaacaata ggacagtgct tattggggag tacttgcaga taaagggcgc cacgcctaga    300
gactccggcc tctatgcttg tactgccagt aggactgtag acagtgaaac ttggtacttc    360
atggtgaatg tcacagatgc catctcatcc ggagatgatg aggatgacac cgatggtgcg    420 gaagatttg tcagtgagaa cagtaacaac aagagagcac catactggac caacacagaa    480
aagatggaaa agcggctcca tgctgtgcct gcggccaaca ctgtcaagtt cgctgccca    540 gccggggga acccaatgcc aaccatgcgg tggctgaaaa acgggaagga gtttaagcag    600
gagcatcgca ttggaggcta caaggtacga aaccagcact ggagcctcat tatggaaagt    660
gtggtcccat ctgacaaggg aaattatacc tgtgtagtgg agaatgaata cgggtccatc    720
aatcacacgt accaccctgga tgttgtggag cgatcgcctc accggccat cctccaagcc    780 ggactgccgg caaatgcctc cacagtggtc ggaggagacg tagagtttgt ctgcaaggtt    840
```

```
tacagtgatg cccagcccca catccagtgg atcaagcacg tggaaaagaa cggcagtaaa    900
tacgggcccg acgggctgcc ctacctcaag gttctcaagg ccgccggtgt aacaccacg    960
gacaaagaga ttgaggttct ctatattcgg aatgtaactt ttgaggacgc tggggaatat   1020
acgtgcttgg cggtaattc tattgggata tcctttcact ctgcatggtt gacagttctg   1080
ccagcgcctg gaagagaaaa ggagattaca gcttccccag actacctgga gatagccatt   1140
tactgcatag gggtcttctt aatcgcctgt atggtggtaa cagtcatcct gtgccgaatg   1200
aagaacacga ccaagaagcc agacttcagc agccagccgg ctgtgcacaa gctgaccaaa   1260
cgtatccccc tgcggagaca ggtaacagtt tcggctgagt ccagctcctc catgaactcc   1320
aacaccccgc tggtgaggat aacaacacgc ctctcttcaa cggcagacac ccccatgctg   1380
gcagggtct ccgagtatga acttccagag gacccaaaat gggagtttcc aagagataag    1440
ctgacactgg gcaagcccct gggagaaggt tgctttgggc aagtggtcat ggcggaagca   1500
gtgggaattg acaaagacaa gcccaaggag gcggtcaccg tggccgtgaa gatgttgaaa   1560
gatgatgcca cagagaaaga ccttctctgat ctggtgtcag agatggagat gatgaagatg   1620
attgggaaac acaagaatat cataaatctt cttggagcct gcacacagga tgggcctctc   1680
tatgtcatag ttgagtatgc ctctaaaggc aacctccgag aatacctccg agcccggagg   1740
ccacccggga tggagtactc ctatgacatt aaccgtgttc ctgaggagca gatgaccttc   1800
aaggacttgg tgtcatgcac ctaccagctg gccagaggca tggagtactt ggcttcccaa   1860
aaatgtattc atcgagattt agcagccaga aatgttttgg taacagaaaa caatgtgatg   1920
aaaatagcag actttggact cgccagagat atcaacaata tagactatta caaaaagacc   1980
accaatgggc ggcttccagt caagtggatg gctccagaag ccctgtttga tagagtatac   2040
actcatcaga gtgatgtctg gtccttcggg gtgttaatgt gggagatctt cactttaggg   2100
ggctcgccct acccagggat tcccgtggag gaactttta agctgctgaa ggaaggacac   2160
agaatggata agccagccaa ctgcaccaac gaactgtaca tgatgatgag ggactgttgg   2220
catgcagtgc cctcccagag accaacgttc aagcagttgg tagaagactt ggatcgaatt   2280
ctcactctca caaccaatga gatcatggag gaaacaaata cgcagattgc ttggccatca   2340
aaactgaaga tcggagccaa atccaagaaa gatccccata ttaaggtttc tggaaagaaa   2400
gaagatgtta agaagccaa ggaaatgatc atgtctgtct tagacacaaa aagcaatcga   2460
gtcacactga gatggatgt ttcacataca gaacattcac atgtaatcgg caaaggtggc   2520
aacaatatta aaaagtgat ggaagaaacc ggatgccata tccactttcc agattccaac   2580
aggaataacc aagcagaaaa aagcaaccag gtatctatag cgggacaacc agcaggagta   2640
gaatctgccc gagttagaat tcgggagctg cttcctttgg tgctgatgtt tgagctacca   2700
attgctggaa ttcttcaacc ggttcctgat cctaattccc cctctattca gcatatatca   2760
caaacgtaca atatttcagt atcatttaaa cagcgttccc gaatgtatgg tgctactgtc   2820
atagtacgag ggtctcagaa taacactagt gctgtgaagg aaggaactgc catgctgtta   2880
gaacatcttg ctgggagctt agcatcagct attcctgtga gcacacaact agatattgca   2940
gctcaacatc atctctttat gatgggtcga atgggagca acatcaaaca tatcatgcag   3000
agaacaggtg ctcagatcca ctttcctgat cccagtaatc cacaaaagaa atctaccgtc   3060
tacctccagg gcaccattga gtctgtctgt cttgcaaggc aatatctcat gggttgtctt   3120
cctcttgtgt tgatgtttga tatgaaggaa gaaattgaag tagatccaca attcattgcg   3180
```

| | |
|---|---|
| cagttgatgg aacagcttga tgtcttcatc agtattaaac caaagcccaa acagccaagc | 3240 |
| aagtctgtga ttgtgaaaag tgttgagcga aatgccttaa atatgtatga agcaaggaaa | 3300 |
| tgtctcctcg gacttgaaag cagtgggggtt accatagcaa ccagtccatc cccagcatcc | 3360 |
| tgccctgccg gcctggcatg tcccagcctg gatatcttag cttcagcagg ccttggactc | 3420 |
| actggactag gtcttttggg acccaccacc ttatctctga cacttcaac aaccccaaac | 3480 |
| tcactcttga atgctcttaa tagctcagtc agtccttgc aaagtccaag ttctggtaca | 3540 |
| cccagcccca cattatgggc accccactt gctaatactt caagtgccac aggttttct | 3600 |
| gctataccac accttatgat tccatctact gcccaagcca cattaactaa tattttgttg | 3660 |
| tctggagtgc ccacctatgg gcacacagct ccatctcccc ctcctggctt gactcctgtt | 3720 |
| gatgtccata tcaacagtat gcagaccgaa ggcaaaaaaa tctctgctgc tttaaatgga | 3780 |
| catgcacagt ctccagatat aaaatatggt gcaatatcca cttcatcact tggagaaaaa | 3840 |
| gtgctgagtg caaatcacgg ggatccgtcc atccagacaa gtgggtctga gcagacatct | 3900 |
| cccaaatcaa gccccactga aggttgtaat gatgcttttg ttgaagtagg catgcctcga | 3960 |
| agtccttccc attctgggaa tgctggtgac ttgaaacaga tgatgtgtcc ctccaaggtt | 4020 |
| tcctgtgcca aaaggcagac agtggaacta ttgcaaggca cgaaaaactc acacttacac | 4080 |
| agcactgaca ggttgctctc agaccctgaa ctgagtgcta ccgaaagccc tttggctgac | 4140 |
| aagaaggctc cagggagtga gcgcgctgca gagagggcag cagctgccca gcaaaactcc | 4200 |
| gaaagggccc accttgctcc acggtcatca tatgtcaaca tgcaggcatt tgactatgaa | 4260 |
| cagaagaagc tattagccac caaagctatg ttaaagaaac cagtggtgac ggaggtcaga | 4320 |
| acgcccacaa atacctggag tggcctgggt ttttctaaat ccatgccagc tgaaactatc | 4380 |
| aaggagttga aagggccaa tcatgtgtcc tataagccca caatgacaac cacttatgag | 4440 |
| ggctcatcca tgtccctttc acggtccaac agtcgtgagc acttgggagg tggaagcgaa | 4500 |
| tctgataact ggagagaccg aaatggaatt ggacctggaa gtcatagtga atttgcagct | 4560 |
| tctattggca gccctaagcg taaacaaaac aaatcaacgg aacactatct cagcagtagc | 4620 |
| aattacatgg actgcatttc ctcgctgaca ggaagcaatg gctgtaactt aaatagctct | 4680 |
| ttcaaaggtt ctgacctccc tgagctcttc agcaaactgg gcctgggcaa atacacagat | 4740 |
| gttttccagc aacaagagat cgatcttcag acattcctca ctctcacaga tcaggatctg | 4800 |
| aaggagctgg aataactac ttttggtgcc aggaggaaaa tgctgcttgc aatttcagaa | 4860 |
| ctaaataaaa accgaagaaa gcttttttgaa tcgccaaatg cacgcacctc tttcctggaa | 4920 |
| ggtggagcga gtggaaggct accccgtcag tatcactcag acattgctag tgtcagtggc | 4980 |
| cgctggtag | 4989 |

<210> SEQ ID NO 24
<211> LENGTH: 5109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

| | |
|---|---|
| atggtcagct ggggtcgttt catctgcctg gtcgtggtca ccatggcaac cttgtccctg | 60 |
| gcccggccct ccttcagttt agttgaggat accacattag agccagaaga gccaccaacc | 120 |
| aaataccaaa tctctcaacc agaagtgtac gtggctgcgc caggggagtc gctagaggtg | 180 |

```
cgctgcctgt tgaaagatgc cgccgtgatc agttggacta aggatggggt gcacttgggg    240
cccaacaata ggacagtgct tattggggag tacttgcaga taaagggcgc cacgcctaga    300
gactccggcc tctatgcttg tactgccagt aggactgtag acagtgaaac ttggtacttc    360
atggtgaatg tcacagatgc catctcatcc ggagatgatg aggatgacac cgatggtgcg    420
gaagattttg tcagtgagaa cagtaacaac aagagagcac catactggac caacacagaa    480
aagatggaaa agcggctcca tgctgtgcct gcggccaaca ctgtcaagtt tcgctgccca    540
gccgggggga acccaatgcc aaccatgcgg tggctgaaaa acgggaagga gtttaagcag    600
gagcatcgca ttggaggcta caaggtacga aaccagcact ggagcctcat tatggaaagt    660
gtggtcccat ctgacaaggg aaattatacc tgtgtagtgg agaatgaata cgggtccatc    720
aatcacacgt accacctgga tgttgtggag cgatcgcctc accggcccat cctccaagcc    780
ggactgccgg caaatgcctc cacagtggtc ggaggagacg tagagtttgt ctgcaaggtt    840
tacagtgatg cccagcccca catccagtgg atcaagcacg tggaaaagaa cggcagtaaa    900
tacgggcccg acgggctgcc ctacctcaag gttctcaagg ccgccggtgt taacaccacg    960
gacaaagaga ttgaggttct ctatattcgg aatgtaactt ttgaggacgc tggggaatat   1020
acgtgcttgg cgggtaattc tattgggata tcctttcact ctgcatggtt gacagttctg   1080
ccagcgcctg gaagagaaaa ggagattaca gcttccccag actacctgga gatagccatt   1140
tactgcatag gggtcttctt aatcgcctgt atggtggtaa cagtcatcct gtgccgaatg   1200
aagaacacga ccaagaagcc agacttcagc agccagccgg ctgtgcacaa gctgaccaaa   1260
cgtatccccc tgcggagaca ggtaacagtt tcggctgagt ccagctcctc catgaactcc   1320 aacacccgc tggtgaggat aacaacacgc ctctcttcaa cggcagacac ccccatgctg   1380 gcagggtct ccgagtatga acttccagag gacccaaaat gggagtttcc aagagataag   1440
ctgacactgg gcaagcccct gggagaaggt tgctttgggc aagtggtcat ggcggaagca   1500
gtgggaattg acaaagacaa gcccaaggag gcggtcaccg tggccgtgaa gatgttgaaa   1560
gatgatgcca cagagaaaga ccttttctga tctggtgtcag agatggagat gatgaagatg   1620
attgggaaac acaagaatat cataaatctt cttggagcct gcacacagga tgggcctctc   1680
tatgtcatag ttgagtatgc ctctaaaggc aacctccgag aatacctccg agcccggagg   1740
ccacccggga tggagtactc ctatgacatt aaccgtgttc ctgaggagca gatgaccttc   1800
aaggacttgg tgtcatgcac ctaccagctg gccagaggca tggagtactt ggcttcccaa   1860
aaatgtattc atcgagattt agcagccaga aatgttttgg taacagaaaa caatgtgatg   1920
aaaatagcag actttggact cgccagagat atcaacaata tagactatta caaaaagacc   1980
accaatgggc ggcttccagt caagtggatg gctccagaag ccctgtttga tagagtatac   2040
actcatcaga gtgatgtctg gtccttcggg gtgttaatgt gggagatctt cactttaggg   2100
ggctcgccct acccagggat tcccgtggag gaacttttta gctgctgaa ggaaggacac   2160 agaatggata agccagccaa ctgcaccaac gaactgtaca tgatgatgag ggactgttgg   2220
catgcagtgc cctcccagag accaacgttc aagcagttgg tagaagactt ggatcgaatt   2280
ctcactctca caaccaatga ggagagtaga tctggagaaa ccaacagctg tgttgaagaa   2340
ataatccggg agatgacctg gcttccacca ctttctgcta ttcaagcacc tggcaaagtg   2400
gaaccaacca aatttccatt tccaaataag gactctcagc ttgtatcctc tggacacaat   2460
aatccaagaa aaggtgatgc agagccagag agtccagaca gtggcacatc gaatacatca   2520
atgctggaag atgaccttaa gctaagcagt gatgaagagg agaatgaaca gcaggcagct   2580
```

```
cagagaacgg ctctccgcgc tctctctgac agcgccgtgg tccagcagcc caactgcaga   2640
acctcggtgc cttccagcaa gggcagcagc agcagcagca gcagcggcag cagcagctcc   2700
tccagcgact cagagagcag ctccggatct gactcggaga ccgagagcag ctccagcgag   2760
agtgagggca gcaagccccc ccacttctcc agccccgagg ctgaaccggc atcctctaac   2820
aagtggcagc tggataaatg gctaaacaaa gttaatcccc acaagcctcc tattctgatc   2880
caaaatgaaa gccacgggtc agagagcaat cagtactaca acccggtgaa agaggacgtc   2940
caggactgtg ggaaagtccc cgacgtttgc cagcccagcc tgagagagaa ggagatcaag   3000
agcacttgca aggaggagca aaggccaagg acagccaaca aggcccctgg gagtaaaggc   3060
gtgaagcaga agtccccgcc cgcggccgtg gccgtggcgg tgagcgcagc cgccccgcca   3120
cccgcagtgc cctgtgcgcc cgcggagaac gcgcccgcgc ctgcccggag gtccgcgggc   3180
aagaagccca ccaggcgcac cgagaggacc tcagccgggg acggcgccaa ctgccaccgg   3240
cccgaggagc ccgcggccgc ggacgcgctg ggacgagcg tggtggtccc ccggagccc   3300 accaaaacca ggccctgtgg caacaacaga gcgagccacc gcaaggagct gcgctcctcc   3360
gtgacctgcg agaagcgccg cacgcggggg ctaagcagga tcgtcccaa atccaaggag   3420 ttcattgaga cagagtcgtc atcttcatcc tcctcctcgg actccgacct ggagtccgag   3480
caggaggagt accctctgtc caaagcacag accgtggctg cctctgcctc ctccgggaat   3540
gatcagaggc tgaaggaggc cgctgccaac gggggcagtg gtcctagggc ccctgtaggc   3600
tccatcaacg ccaggaccac cagtgacatc gccaaggagc tggaggagca gttctacaca   3660
ctggtcccct ttggccggaa cgaacttctc tcccctctaa aggacagtga tgagatcagg   3720
tctctctggg tcaaaatcga cctgaccctc ctgtccagga tcccagaaca cctgccccag   3780
gagccagggg tattgagcgc ccctgccacc aaggactctg agagcgcacc gcccagccac   3840
acctcggaca cacctgcaga aaaggctttg ccaaaatcca agaggaaacg caagtgtgac   3900
aacgaagacg actacaggga gatcaagaag tcccagggag agaaagacag ctcttcaaga   3960
ctggccacct ccaccagtaa tactttgtct gcaaaccact gcaacatgaa catcaacagt   4020
gtggcaatac caataaataa aaatgaaaaa atgcttcggt cgcccatctc accctctct   4080 gatgcatcta aacacaaata caccagcgag gacttaactt cttccagccg acctaatggc   4140
aacagtttgt ttacttcagc ctcttccagc aaaaagccta aggccgacag ccagctgcag   4200
cctcacggcg gagacctcac gaaagcagct cacaacaatt ctgaaaacat tcccctccac   4260
aagtcacggc gcagacgaa gccgtggtct ccaggctcca acggcacag ggactgcaag   4320 aggcagaaac ttgtcttcga tgatatgcct cgcagtgccg attattttat gcaagaagct   4380
aaacgaatga agcataaagc agatgcaatg gtggaaaagt ttggaaaggc tttgaactat   4440
gctgaagcag cattgtcgtt tatcgagtgt ggaaatgcaa tggaacaagg ccccatggaa   4500
tccaaatctc cttatacgat gtattcagaa acagtagagc tcatcaggta tgctatgaga   4560
ctaaaaaccc actcaggccc caatgccaca ccagaagaca aacaactggc tgcattatgt   4620
taccgatgcc tggccctcct gtactggcgg atgtttcgac tcaaaaggga ccacgctgta   4680
aagtattcaa aagcactaat cgactatttc aagaactcat ctaaagccgc caagccccca   4740
tctccgtggg gggccagtgg aaagagcact ggaaccccat cccccatgtc tcccaaccc   4800 tctcccgcca gctccgtggg gtctcagggc agcctctcca acgccagcgc cctgtccccg   4860
tcgaccatcg tcagcatccc acagcgcatc caccagatgg cggccaacca cgtcagcatc   4920
```

| | |
|---|---|
| accaacagca tcctgcacag ctacgactac tgggagatgg ccgacaacct ggccaaggaa | 4980 |
| aaccgagaat tcttcaacga cctggatctg ctcatggggc cggtcaccct gcacagcagc | 5040 |
| atggagcacc tggtccagta ctcccaacag ggcctgcact ggctgcggaa cagcgcccac | 5100 |
| ctgtcatag | 5109 |

```
<210> SEQ ID NO 25
<211> LENGTH: 3213
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
```

| | |
|---|---|
| atggtcagct ggggtcgttt catctgcctg gtcgtggtca ccatggcaac cttgtccctg | 60 |
| gcccggccct ccttcagttt agttgaggat accacattag agccagaaga gccaccaacc | 120 |
| aaataccaaa tctctcaacc agaagtgtac gtggctgcgc caggggagtc gctagaggtg | 180 |
| cgctgcctgt tgaaagatgc cgccgtgatc agttggacta aggatggggt gcacttgggg | 240 |
| cccaacaata ggacagtgct tattggggag tacttgcaga taaagggcgc cacgcctaga | 300 |
| gactccggcc tctatgcttg tactgccagt aggactgtag acagtgaaac ttggtacttc | 360 |
| atggtgaatg tcacagatgc catctcatcc ggagatgatg aggatgacac cgatggtgcg | 420 |
| gaagattttg tcagtgagaa cagtaacaac aagagagcac catactggac caacacagaa | 480 |
| aagatggaaa agcggctcca tgctgtgcct gcggccaaca ctgtcaagtt tcgctgccca | 540 |
| gccgggggga acccaatgcc aaccatgcgg tggctgaaaa acgggaagga gtttaagcag | 600 |
| gagcatcgca ttgaggcta caaggtacga aaccagcact ggagcctcat tatggaaagt | 660 |
| gtggtcccat ctgacaaggg aaattatacc tgtgtagtgg agaatgaata cgggtccatc | 720 |
| aatcacacgt accacctgga tgttgtggag cgatcgcctc accggcccat cctccaagcc | 780 |
| ggactgccgg caaatgcctc cacagtggtc ggaggagacg tagagtttgt ctgcaaggtt | 840 |
| tacagtgatg cccagcccca catccagtgg atcaagcacg tggaaaagaa cggcagtaaa | 900 |
| tacgggcccg acgggctgcc ctacctcaag gttctcaagg ccgccggtgt taacaccacg | 960 |
| gacaaagaga ttgaggttct ctatattcgg aatgtaactt ttgaggacgc tggggaatat | 1020 |
| acgtgcttgg cgggtaattc tattgggata tcctttcact ctgcatggtt gacagttctg | 1080 |
| ccagcgcctg aagagaaaaa ggagattaca gcttccccag actacctgga gatagccatt | 1140 |
| tactgcatag gggtcttctt aatcgcctgt atggtggtaa cagtcatcct gtgccgaatg | 1200 |
| aagaacacga ccaagaagcc agacttcagc agccagccgg ctgtgcacaa gctgaccaaa | 1260 |
| cgtatcccc tgcggagaca ggtaacagtt tcggctgagt ccagctcctc catgaactcc | 1320 |
| aacaccccgc tggtgaggat aacaacacgc ctctcttcaa cggcagacac ccccatgctg | 1380 |
| gcagggtct ccgagtatga acttccagag gacccaaaat gggagtttcc aagagataag | 1440 |
| ctgacactgg gcaagcccct gggagaaggt tgctttgggc aagtggtcat ggcggaagca | 1500 |
| gtgggaattg acaaagacaa gcccaaggag gcggtcaccg tggccgtgaa gatgttgaaa | 1560 |
| gatgatgcca cagagaaaga cctttctgat ctggtgtcag agatggagat gatgaagatg | 1620 |
| attgggaaac acaagaatat cataaatctt cttggagcct gcacacagga tgggcctctc | 1680 |
| tatgtcatag ttgagtatgc ctctaaaggc aacctccgag aatacctccg agccggagag | 1740 |
| ccacccggga tggagtactc ctatgacatt aaccgtgttc ctgaggagca gatgaccttc | 1800 |

-continued

```
aaggacttgg tgtcatgcac ctaccagctg gccagaggca tggagtactt ggcttcccaa    1860
aaatgtattc atcgagattt agcagccaga aatgttttgg taacagaaaa caatgtgatg    1920
aaaatagcag actttggact cgccagagat atcaacaata tagactatta caaaaagacc    1980
accaatgggc ggcttccagt caagtggatg gctccagaag ccctgtttga tagagtatac    2040
actcatcaga gtgatgtctg gtccttcggg gtgttaatgt gggagatctt cactttaggg    2100
ggctcgccct acccagggat tcccgtggag gaacttttta agctgctgaa ggaaggacac    2160
agaatggata agccagccaa ctgcaccaac gaactgtaca tgatgatgag ggactgttgg    2220
catgcagtgc cctcccagag accaacgttc aagcagttgg tagaagactt ggatcgaatt    2280
ctcactctca caaccaatga gatggcagat gatcagggct gtattgaaga gcagggggtt    2340
gaggattcag caaatgaaga ttcagtggat gctaagccag accggtcctc gtttgtaccg    2400
tccctcttca gtaagaagaa gaaaaatgtc accatgcgat ccatcaagac cacccgggac    2460
cgagtgccta catatcagta caacatgaat tttgaaaagc tgggcaaatg catcataata    2520
aacaacaaga actttgataa agtgacaggt atgggcgttc gaaacggaac agacaaagat    2580
gccgaggcgc tcttcaagtg cttccgaagc ctgggttttg acgtgattgt ctataatgac    2640
tgctcttgtg ccaagatgca agatctgctt aaaaaagctt ctgaagagga ccatacaaat    2700
gccgcctgct tcgcctgcat cctcttaagc catggagaag aaaatgtaat ttatgggaaa    2760
gatggtgtca caccaataaa ggatttgaca gcccacttta gggggatag atgcaaaacc    2820 ctttttagaga aacccaaact cttcttcatt caggcttgcc gagggaccga gcttgatgat    2880
ggcatccagg ccgactcggg gcccatcaat gacacagatg ctaatcctcg atacaagatc    2940
ccagtggaag ctgacttcct cttcgcctat tccacggttc caggctatta ctcgtggagg    3000
agcccaggaa gaggctcctg gtttgtgcaa gccctctgct ccatcctgga ggagcacgga    3060
aaagacctgg aaatcatgca gatcctcacc agggtgaatg acagagttgc caggcacttt    3120
gagtctcagt ctgatgaccc acacttccat gagaagaagc agatcccctg tgtggtctcc    3180
atgctcacca aggaactcta cttcagtcaa tag                                 3213
```

<210> SEQ ID NO 26
<211> LENGTH: 3423
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
atggtcagct ggggtcgttt catctgcctg gtcgtggtca ccatggcaac cttgtccctg     60
gcccggccct ccttcagttt agttgaggat accacattag agccagaaga gccaccaacc    120
aaataccaaa tctctcaacc agaagtgtac gtggctgcgc aggggagtc gctagaggtg     180 cgctgcctgt tgaaagatgc cgccgtgatc agttggacta aggatgggt gcacttgggg     240 cccaacaata ggacagtgct tattggggag tacttgcaga taaagggcgc cacgcctaga     300
gactccggcc tctatgcttg tactgccagt aggactgtag acagtgaaac ttggtacttc    360
atggtgaatg tcacagatgc catctcatcc ggagatgatg aggatgacac cgatggtgcg    420
gaagattttg tcagtgagaa cagtaacaac aagagagcac catactggac caacacagaa    480
aagatggaaa agcggctcca tgctgtgcct gcggccaaca ctgtcaagtt cgctgcccca    540
gccgggggga acccaatgcc aaccatgcgg tggctgaaaa acgggaagga gtttaagcag    600
```

```
gagcatcgca ttggaggcta caaggtacga aaccagcact ggagcctcat tatggaaagt    660
gtggtcccat ctgacaaggg aaattatacc tgtgtagtgg agaatgaata cgggtccatc    720
aatcacacgt accacctgga tgttgtggag cgatcgcctc accggcccat cctccaagcc    780
ggactgccgg caaatgcctc cacagtggtc ggaggagacg tagagtttgt ctgcaaggtt    840
tacagtgatg cccagcccca catccagtgg atcaagcacg tggaaaagaa cggcagtaaa    900
tacgggcccg acgggctgcc ctacctcaag gttctcaagg ccgccggtgt taacaccacg    960
gacaaagaga ttgaggttct ctatattcgg aatgtaactt ttgaggacgc tggggaatat   1020
acgtgcttgg cgggtaattc tattgggata tcctttcact ctgcatggtt gacagttctg   1080
ccagcgcctg aagagaaaa ggagattaca gcttccccag actacctgga gatagccatt   1140
tactgcatag gggtcttctt aatcgcctgt atggtggtaa cagtcatcct gtgccgaatg   1200
aagaacacga ccaagaagcc agacttcagc agccagccgg ctgtgcacaa gctgaccaaa   1260
cgtatccccc tgcggagaca ggtaacagtt tcggctgagt ccagctcctc catgaactcc   1320
aacacccgc tggtgaggat aacaaacgc ctctcttcaa cggcagacac ccccatgctg   1380
gcagggtct ccgagtatga acttccagag gacccaaaat gggagtttcc aagagataag   1440
ctgacactgg gcaagccct gggagaaggt tgctttgggc aagtggtcat ggcggaagca   1500
gtgggaattg acaaagacaa gcccaaggag gcggtcaccg tggccgtgaa gatgttgaaa   1560
gatgatgcca cagagaaaga cctttctgat ctggtgtcag agatggagat gatgaagatg   1620
attgggaaac acaagaatat cataaatctt cttggagcct gcacacagga tgggcctctc   1680
tatgtcatag ttgagtatgc ctctaaaggc aacctccgag aatacctccg agcccggagg   1740
ccacccggga tggagtactc ctatgacatt aaccgtgttc ctgaggagca gatgaccttc   1800
aaggacttgg tgtcatgcac ctaccagctg gccagaggca tggagtactt ggcttcccaa   1860
aaatgtattc atcgagattt agcagccaga aatgttttgg taacagaaaa caatgtgatg   1920
aaaatagcag acttttggact cgccagagat atcaacaata tagactatta caaaagacc   1980
accaatgggc ggcttccagt caagtggatg gctccagaag ccctgtttga tagagtatac   2040
actcatcaga gtgatgtctg gtccttcggg gtgttaatgt gggagatctt cactttaggg   2100
ggctcgccct acccagggat tcccgtggag gaacttttta agctgctgaa ggaaggacac   2160
agaatggata gccagccaa ctgccaccaac gaactgtaca tgatgatgag ggactgttgg   2220
catgcagtgc cctcccagag accaacgttc aagcagttgg tagaagactt ggatcgaatt   2280
ctcactctca caaccaatga gcaagccagg gctgagcagg aagaagaatt cattagtaac   2340
actttattca agaaaattca ggctttgcag aaggagaaag aaaccttgc tgtaaattat   2400
gagaaagaag aagaattcct cactaatgag ctctccagaa aattgatgca gttgcagcat   2460
gagaaagccg aactagaaca gcatcttgaa caagagcagg aatttcaggt caacaaactg   2520
atgaagaaaa ttaaaaaact ggagaatgac accatttcta gcaacttac attgaacag   2580
ttgagacggg agaagattga ccttgaaaat acattggaac aagaacaaga agcactagtt   2640
aatcgcctct ggaaaaggat ggataagctt gaagctgaaa agcgaatcct gcaggaaaaa   2700
ttagaccagc ccgtctctgc tccaccatcg cctagagata tctccatgga gattgattct   2760
ccagaaaata tgatgcgtca catcaggttt ttaaagaatg aagtggaacg gctgaagaag   2820
caactgagag ctgctcagtt acagcattca gagaaaatgg cacagtatct ggaggaggaa   2880
cgtcacatga gagaagagaa cttgaggctc cagaggaagc tgcagaggga gatggagaga   2940
agagaagccc tctgtcgaca gctctccgag agtgagtcca gcttagaaat ggacgacgaa   3000
```

| | |
|---|---|
| aggtattta atgagatgtc tgcacaagga ttaagacctc gcactgtgtc cagcccgatc | 3060 |
| ccttacacac cttctccgag ttcaagcagg cctatatcac ctggtctatc atatgcaagt | 3120 |
| cacacggttg gtttcacgcc accaacttca ctgactagag ctggaatgtc ttattacaat | 3180 |
| tccccgggtc ttcacgtgca gcacatggga acatcccatg gtatcacaag gccttcacca | 3240 |
| cggagaagca acagtcctga caaattcaaa cggcccacgc cgcctccatc tcccaacaca | 3300 |
| cagaccccag tccagccacc tccgcctcca cctccgccac ccatgcagcc cacggtcccc | 3360 |
| tcagcagcca cctcgcagcc tactccttcg caacattcgg cgcacccctc ctcccagcct | 3420 |
| taa | 3423 |

<210> SEQ ID NO 27
<211> LENGTH: 5229
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

| | |
|---|---|
| atggtcagct ggggtcgttt catctgcctg gtcgtggtca ccatggcaac cttgtccctg | 60 |
| gcccggccct ccttcagttt agttgaggat accacattag agccagaaga gccaccaacc | 120 |
| aaataccaaa tctctcaacc agaagtgtac gtggctgcgc caggggagtc gctagaggtg | 180 |
| cgctgcctgt tgaaagatgc cgccgtgatc agttggacta aggatggggt gcacttgggg | 240 |
| cccaacaata ggacagtgct tattggggag tacttgcaga taagggcgc cacgcctaga | 300 |
| gactccggcc tctatgcttg tactgccagt aggactgtag acagtgaaac ttggtacttc | 360 |
| atggtgaatg tcacagatgc catctcatcc ggagatgatg aggatgacac cgatggtgcg | 420 |
| gaagattttg tcagtgagaa cagtaacaac aagagagcac catactggac caacacagaa | 480 |
| aagatggaaa agcggctcca tgctgtgcct gcggccaaca ctgtcaagtt tcgctgccca | 540 |
| gccggggggaa acccaatgcc aaccatgcgg tggctgaaaa acgggaagga gtttaagcag | 600 |
| gagcatcgca ttggaggcta caaggtacga aaccagcact ggagcctcat tatggaaagt | 660 |
| gtggtcccat ctgacaaggg aaattatacc tgtgtagtgg agaatgaata cgggtccatc | 720 |
| aatcacacgt accacctgga tgttgtggag cgatcgcctc accggcccat cctccaagcc | 780 |
| ggactgccgg caaatgcctc cacagtggtc ggaggagacg tagagtttgt ctgcaaggtt | 840 |
| tacagtgatg cccagcccca catccagtgg atcaagcacg tggaaaagaa cggcagtaaa | 900 |
| tacgggcccg acgggctgcc ctacctcaag gttctcaagg ccgccggtgt taacaccacg | 960 |
| gacaaagaga ttgaggttct ctatattcgg aatgtaactt tgaggacgc tggggaatat | 1020 |
| acgtgcttgg cgggtaattc tattgggata tcctttcact ctgcatggtt gacagttctg | 1080 |
| ccagcgcctg gaagagaaaa ggagattaca gcttccccag actacctgga tagccatt | 1140 |
| tactgcatag gggtcttctt aatcgcctgt atggtggtaa cagtcatcct gtgccgaatg | 1200 |
| aagaacacga ccaagaagcc agacttcagc agccagccgg ctgtgcacaa gctgaccaaa | 1260 |
| cgtatccccc tgcggagaca ggtaacagtt tcggctgagt ccagctcctc catgaactcc | 1320 |
| aacacccgc tggtgaggat aacaacacgc ctctcttcaa cggcagacac ccccatgctg | 1380 |
| gcagggtct ccgagtatga acttccagag gacccaaaat gggagtttcc aagagataag | 1440 |
| ctgcacactgg gcaagcccct gggagaaggt tgctttgggc aagtggtcat ggcggaagca | 1500 |
| gtgggaattg acaaagacaa gcccaaggag gcggtcaccg tggccgtgaa gatgttgaaa | 1560 |

```
gatgatgcca cagagaaaga cctttctgat ctggtgtcag agatggagat gatgaagatg    1620
attgggaaac acaagaatat cataaatctt cttggagcct gcacacagga tgggcctctc    1680
tatgtcatag ttgagtatgc ctctaaaggc aacctccgag aatacctccg agcccggagg    1740
ccacccggga tggagtactc ctatgacatt aaccgtgttc ctgaggagca gatgaccttc    1800
aaggacttgg tgtcatgcac ctaccagctg gccagaggca tggagtactt ggcttcccaa    1860
aaatgtattc atcgagattt agcagccaga aatgttttgg taacagaaaa caatgtgatg    1920
aaaatagcag actttggact cgccagagat atcaacaata tagactatta caaaaagacc    1980
accaatgggc ggcttccagt caagtggatg gctccagaag ccctgtttga tagagtatac    2040
actcatcaga gtgatgtctg gtccttcggg gtgttaatgt gggagatctt cactttaggg    2100
ggctcgccct acccagggat tcccgtggag gaactttttg agctgctgaa ggaaggacac    2160
agaatggata agccagccaa ctgcaccaac gaactgtaca tgatgatgag ggactgttgg    2220
catgcagtgc cctcccagag accaacgttc aagcagttgg tagaagactt ggatcgaatt    2280
ctcactctca caaccaatga cacaacttc gaaaccagc taattcatga gttgatgcac    2340
cctgtattga gtggagaact gcagcctcgg tccatttcag tagaagggag ctccctctta    2400
ataggcgcct ctaactcttt agtggcagat cacttacaaa gatgtggcta tgaatattca    2460
ctttctgttt tctttccaga aagtggtttg caaaagaaa aggtatttac tatgcaggat    2520
ctattacaac tcattaaaat caaccctact tccagtctct acaaatcact ggtttcagga    2580
tctgataaag aaaatcaaaa aggttttctt atgcattttt taaagaatt ggcagaatat    2640 catcaagcta agagagttg taatatggaa actcagacaa gttcgacatt aacagagat    2700 tctctggctg agaagcttca gcttattgat gatcagtttg cagatgctta ccctcagcgt    2760
atcaagttcg aatctttaga aataaagcta aatgagtata agagagaaat agaagagcaa    2820
cttcgggcag aaatgtgtca aaagttgaag tttttaaag ataccgagat agcaaaaatt    2880
aaaatggaag caaaaaaaa gtatgaaaag gagttaacca tgttccagaa tgattttgaa    2940
aaagcttgtc aagcaaaatc tgaagctctc gttcttcggg aaaagagtac ccttgaaaga    3000
attcacaagc accaagagat tgaaacaaaa gaaatttatg ctcaaaggca acttttacta    3060
aaagatatgg attgctaag aggaagagaa gcagagctga agcaaagagt tgaagctttt    3120
gaattgaacc agaagctcca ggaagaaaaa cataaaagca taactgaggc acttaggaga    3180
caggagcaga atataaagag ttttgaggag acctatgacc gaaagctcaa gaatgaactt    3240
ctaaagtatc aacttgaact gaaggatgac tacatcatta gaactaatcg actgattgaa    3300
gatgaaagga gaataaaga aaaagctgtt catttgcaag aggagctcat agctattaat    3360
tcaaaaaagg aggaactcaa tcaatctgta aatcgtgtga aagaacttga gcttgaatta    3420
gagtctgtca agcccagtc tttggcaata acaaaacaaa accatatgct gaatgaaaag    3480
gttaaagaga tgagtgatta ttcactacta aagaagagaa actggagct tctggcacaa    3540 aataaattac ttaaacaaca actggaagag agtagaaatg aaaacctgcg tctcctaaac    3600
cgcctagctc agccggctcc tgaacttgca gtctttcaga aagaactacg gaaagccgaa    3660
aaggctatag tggttgagca tgaggagttc gaaagctgca ggcaagctct gcacaaacaa    3720
ctgcaagacg aaattgagca ttctgcacag ctgaaggccc agattctagg ttacaaagct    3780
tctgtaaaga gtttaactac tcaggttgcc gatttaaaat tgcaactgaa gcaaactcag    3840
acagccctag agaatgaagt gtactgcaat ccaaagcagt ctgtgatcga tcgttctgtc    3900
```

```
aatggattaa taaatggcaa tgtggtgcct tgcaatggtg agataagtgg ggatttcttg    3960
aacaatcctt ttaaacagga aaacgttcta gcacgtatgg ttgcatcaag gatcacaaat    4020
tatccaactg catgggtgga gggtagttcc cctgattctg accttgagtt tgtagccaat    4080
actaaggcaa gggtcaaaga gcttcagcaa gaggccgaac gcttggaaaa ggctttcaga    4140
agttaccatc ggagagtcat taaaaactct gccaaaagcc cactagcagc aaagagccca    4200
ccatctctgc acttgctgga agccttcaaa aacattactt ccagttcccc ggaaagacat    4260 attttttggag aggacagagt tgtctctgag cagcctcaag tgggcacact tgaagaaagg    4320
aatgacgtcg tggaagcact gacaggcagt gcagcctcga ggctccgcgg gggcacttcc    4380
tccagacgcc tctcttccac accccttcca aaagcaaaaa gaagcctcga aagtgaaatg    4440
tatctggaag gtctgggcag atcacacatt gcttcccccca gtccttgtcc tgacagaatg    4500
cccctaccat cacccactga gtctaggcac agcctctcca tccctcctgt ctccagccct    4560
ccggagcaga aagtgggtct ttatcgaaga caaactgaac ttcaagacaa aagtgaattt    4620
tcagatgtgg acaagctagc ttttaaggat aatgaggagt ttgaatcatc ttttgaatct    4680
gcagggaaca tgccaaggca gttggaaatg ggcgggcttt ctcctgccgg ggatatgtct    4740
catgtggacg ctgctgcagc tgctgtgccc ctctcatatc agcacccaag tgtagatcag    4800
aaacaaattg aagaacaaaa ggaagaagaa aaaatacggg aacagcaagt gaaagaacga    4860
aggcagagag aagaaagaag gcagagtaac ctacaagaag ttttagaaag ggaacgaaga    4920
gaactagaaa aactgtatca ggaaaggaag atgattgaag aatcactgaa gattaaaata    4980
aaaaaggaat tagaaatgga aaatgaatta gaaatgagta atcaagaaat aaaagacaaa    5040
tctgctcaca gtgaaaatcc tttagagaaa tacatgaaaa tcatccagca ggagcaagac    5100
caggagtcgg cagataagag ctcaaaaaag atggtccaag aaggctccct agtggacacg    5160
ctgcaatcta gtgacaaagt cgaaagttta acaggctttt ctcatgaaga actagacgac    5220
tcttggtaa                                                           5229
```

FGFR/PD-1 COMBINATION THERAPY FOR THE TREATMENT OF CANCER

CROSS REFERENCE TO RELATED APPLICATIONS

This application claims priority to U.S. Provisional Application No. 62/142,569, filed Apr. 3, 2015, the disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Mar. 22, 2016, is named PRD3366USNP_SL.txt and is 53,086 bytes in size.

TECHNICAL FIELD

Provided herein are combination therapies for the treatment of cancer. In particular, the disclosed methods are directed to treatment of cancer in a patient comprising administering an antibody that blocks the interaction between PD-1 and PD-L1 and a fibroblast growth factor receptor (FGFR) inhibitor.

BACKGROUND

For cancer patients failing the main therapeutic option (front-line therapy) for that cancer type, there is often no accepted standard of care for second and subsequent-line therapy, unless a particular genetic abnormality is identified and a specific therapy is available. Fibroblast growth factor receptors (FGFRs) are a family of receptor tyrosine kinases involved in regulating cell survival, proliferation, migration and differentiation. FGFR alterations have been observed in some cancers. To date, there are no approved therapies that are efficacious in patients with FGFR alterations.

SUMMARY

Disclosed herein are methods of using a combination therapy comprising an antibody that blocks the interaction between PD-1 and PD-L1 and an FGFR inhibitor to treat cancer in the patient. In some embodiments, the methods comprise administering to the patient a pharmaceutically effective amount of an antibody that blocks the interaction between PD-1 and PD-L1 and a pharmaceutically effective amount of an FGFR inhibitor, wherein the antibody that blocks the interaction between PD-1 and PD-L1 and the FGFR inhibitor are administered if one or more FGFR variants are present in a biological sample from the patient.

In other embodiments, the methods of treating cancer in a patient comprise: administering to the patient a pharmaceutically effective amount of an antibody that blocks the interaction between PD-1 and PD-L1; monitoring the efficacy of the antibody; and, if the antibody is not efficacious, evaluating a biological sample from the patient for a presence of one or more FGFR variants and administering to the patient a pharmaceutically effective amount of an FGFR inhibitor if the one or more FGFR variants are present in the sample.

BRIEF DESCRIPTION OF THE DRAWINGS

The summary, as well as the following detailed description, is further understood when read in conjunction with the appended drawings. For the purpose of illustrating the disclosed methods, there are shown in the drawings exemplary embodiments of the methods; however, the methods are not limited to the specific embodiments disclosed. In the drawings.

DETAILED DESCRIPTION OF ILLUSTRATIVE EMBODIMENTS

Figure 1:
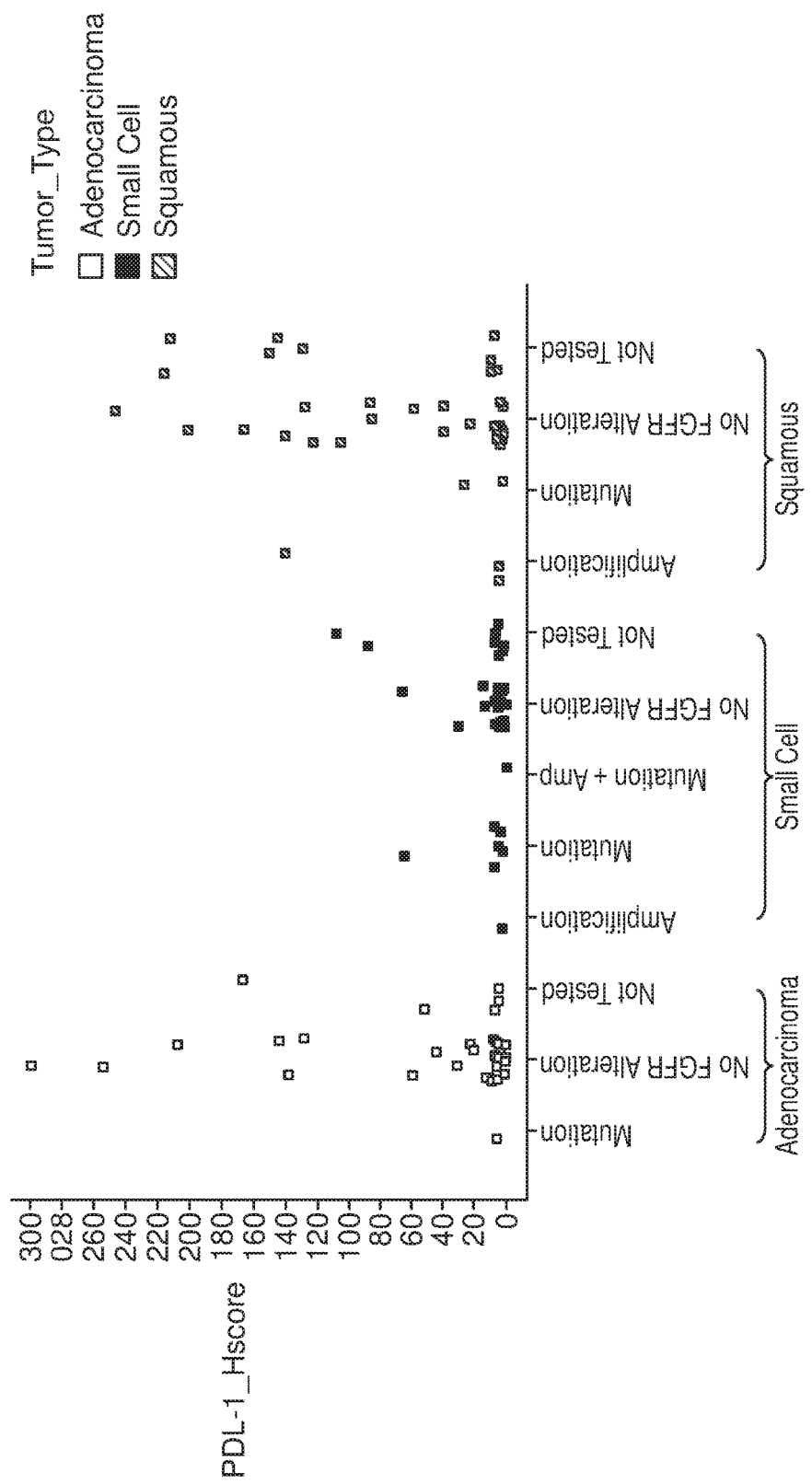
FIG. 1 illustrates PD-L1 expression in a 120 lung cancer samples set by histology and FGFR mutant and amplification status. PD-L1 H-scores (Y-axis) were plotted for NSCLC adenocarcinoma (left), small cell lung cancer (middle), and NSCLC squamous (right). The FGFR mutation and/or amplification status versus the PD-L1 staining for each of the 120 samples is shown. Mutation—an FGFR mutation was identified; No FGFR Alteration—no mutation or fusion was detected; Amplification—an FGFR gene amplification was identified; Mutation+Amp—samples positive for both FGFR mutation and gene amplification; Not Tested—IHC for PD-L1 was performed, but sample was not tested on Foundation Medicine panel.

The disclosed methods may be understood more readily by reference to the following detailed description taken in connection with the accompanying figures, which form a part of this disclosure. It is to be understood that the disclosed methods are not limited to the specific methods described and/or shown herein, and that the terminology used herein is for the purpose of describing particular embodiments by way of example only and is not intended to be limiting of the claimed methods.

Unless specifically stated otherwise, any description as to a possible mechanism or mode of action or reason for improvement is meant to be illustrative only, and the disclosed methods are not to be constrained by the correctness or incorrectness of any such suggested mechanism or mode of action or reason for improvement.

Reference to a particular numerical value includes at least that particular value, unless the context clearly dictates otherwise. When a range of values is expressed, another embodiment includes from the one particular value and/or to the other particular value. Further, reference to values stated in ranges include each and every value within that range. All ranges are inclusive and combinable.

When values are expressed as approximations, by use of the antecedent "about," it will be understood that the particular value forms another embodiment.

The term "about" when used in reference to numerical ranges, cutoffs, or specific values is used to indicate that the recited values may vary by up to as much as 10% from the listed value. Thus, the term "about" is used to encompass variations of ±10% or less, variations of ±5% or less, variations of ±1% or less, variations of ±0.5% or less, or variations of ±0.1% or less from the specified value.

It is to be appreciated that certain features of the disclosed methods which are, for clarity, described herein in the context of separate embodiments, may also be provided in combination in a single embodiment. Conversely, various features of the disclosed methods that are, for brevity, described in the context of a single embodiment, may also be provided separately or in any subcombination.

As used herein, the singular forms "a," "an," and "the" include the plural.

The following abbreviations are used throughout the disclosure: FFPE (formalin-fixed, paraffin-embedded); NSCLC (non-small-cell lung carcinoma); SCLC (small-cell lung cancer); FGFR (fibroblast growth factor receptor); PD-1 (programmed cell death 1); PD-L1 (programmed death-ligand 1); FGFR3:TACC3 (fusion between genes encoding FGFR3 and transforming acidic coiled-coil containing protein); FGFR3:BAIAP2L1 (fusion between genes encoding FGFR3 and brain-specific angiogenesis inhibitor 1-associated protein 2-like protein 1); FGFR2:AFF3 (fusion between genes encoding FGFR2 and AF4/FMR2 family, member 3); FGFR2:BICC1 (fusion between genes encoding FGFR2 and bicaudal C homolog 1); FGFR2:CASP7 (fusion between genes encoding FGFR2 and caspase 7); FGFR2:CCDC6 (fusion between genes encoding FGFR2 and coiled-coil domain containing 6); FGFR2:OFD1 (fusion between genes encoding FGFR2 and oral-facial-digital syndrome 1).

The term "antibody" refers to (a) immunoglobulin polypeptides, i.e., polypeptides of the immunoglobulin family that contain an antigen binding site that specifically binds to a specific antigen (e.g., PD-1 or PD-L1), including all immunoglobulin isotypes (IgG, IgA, IgE, IgM, IgD, and IgY), classes (e.g. IgG1, IgG2, IgG3, IgG4, IgA1, IgA2), subclasses, and various monomeric and polymeric forms of each isotype, unless otherwise specified, and (b) conservatively substituted variants of such immunoglobulin polypeptides that immunospecifically bind to the antigen (e.g., PD-1 or PD-L1). Antibodies are generally described in, for example, Harlow & Lane, Antibodies: A Laboratory Manual (Cold Spring Harbor Laboratory Press, 1988). Unless otherwise apparent from the context, reference to an antibody also includes antibody derivatives as described in more detail below.

"Antibody fragments" comprise a portion of a full length antibody, generally the antigen-binding or variable region thereof, such as Fab, Fab', F(ab')$_2$, and Fv fragments; diabodies; linear antibodies; single-chain antibody molecules; and multispecific antibodies formed from antibody fragments. Various techniques have been developed for the production of antibody fragments, including proteolytic digestion of antibodies and recombinant production in host cells; however, other techniques for the production of antibody fragments will be apparent to the skilled practitioner. In some embodiments, the antibody fragment of choice is a single chain Fv fragment (scFv). "Single-chain Fv" or "scFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv and other antibody fragments, see James D. Marks, Antibody Engineering, Chapter 2, Oxford University Press (1995) (Carl K. Borrebaeck, Ed.).

An "antibody derivative" means an antibody, as defined above, that is modified by covalent attachment of a heterologous molecule such as, e.g., by attachment of a heterologous polypeptide (e.g., a cytotoxin) or therapeutic agent (e.g., a chemotherapeutic agent), or by glycosylation, deglycosylation, acetylation or phosphorylation not normally associated with the antibody, and the like.

The term "monoclonal antibody" refers to an antibody that is derived from a single cell clone, including any eukaryotic or prokaryotic cell clone, or a phage clone, and not the method by which it is produced. Thus, the term "monoclonal antibody" is not limited to antibodies produced through hybridoma technology.

"Biological sample" refers to any sample from a patient in which cancerous cells can be obtained and protein expression can be evaluated and/or RNA can be isolated. Suitable biological samples include, but are not limited to, blood, lymph fluid, bone marrow, sputum, a solid tumor sample, or any combination thereof. In some embodiments, the biological sample can be formalin-fixed paraffin-embedded tissue (FFPET).

As used here, "block(s) the interaction" refers to the ability of an anti-PD-1 antibody or an anti-PD-L1 antibody to inhibit or reduce binding of PD-L1 to PD-1, such that signaling/functioning through PD-1 is abolished or diminished.

As used herein, "FGFR variant" refers to an alteration in the wild type FGFR gene, including, but not limited to, FGFR fusion genes, FGFR mutations, FGFR amplifications, or any combination thereof "FGFR fusion" or "FGFR fusion gene" refers to a gene encoding a portion of FGFR (e.g., FGRF2 or FGFR3) and one of the herein disclosed fusion partners created by a translocation between the two genes.

As used herein, "patient" is intended to mean any animal, in particular, mammals. Thus, the methods are applicable to human and nonhuman animals, although most preferably with humans. "Patient" and "subject" may be used interchangeably herein.

"Pharmaceutically effective amount" refers to an amount of an antibody that blocks the interaction between PD-1 and PD-L1 and an amount of an FGFR inhibitor that treats the patient.

As used herein, "treating" and like terms refer to reducing the severity and/or frequency of cancer symptoms, eliminating cancer symptoms and/or the underlying cause of said symptoms, reducing the frequency or likelihood of cancer symptoms and/or their underlying cause, and improving or remediating damage caused, directly or indirectly, by cancer.

Disclosed herein are methods of treating cancer in a patient comprising: administering to the patient a pharmaceutically effective amount of an antibody that blocks the interaction between PD-1 and PD-L1 and a pharmaceutically effective amount of an FGFR inhibitor, wherein the antibody that blocks the interaction between PD-1 and PD-L1 and the FGFR inhibitor are administered if one or more FGFR variants are present in a biological sample from the patient.

PD-1 is a cell surface receptor expressed on the surface of CD4+ and CD8+ T cells, B cells, and myeloid cells. The ligands of PD-1, PD-L1 and PD-L2, are expressed on immune cells; in addition, PD-L1 is also expressed on cancer cells. When engaged by its ligands, PD-1 downregulates the immune response by reducing T cell proliferation, cytokine production and effector function. Antibodies against PD-1 (anti-PD-1 antibodies) and/or its ligands (anti-PD-L1 antibodies, for example) can block the interaction between PD-1 and PD-L1, thereby inhibiting the downregulation of the immune response. The disclosed methods comprise administering to the patient a pharmaceutically effective amount of an antibody that blocks the interaction between PD-1 and PD-L1. In some embodiments, the methods can comprise administering to the patient a pharmaceutically effective amount of an anti-PD-1 antibody. In some embodiments, the methods can comprise administering to the patient a pharmaceutically effective amount of an anti-PD-L1 antibody. In some embodiments, the methods can comprise administering to the patient a pharmaceutically effective amount of an anti-PD-1 antibody and an anti-PD-L1 antibody.

Exemplary anti-PD-1 antibodies include, but are not limited to, OPDIVO® (nivolumab) (Bristol-Myers Squibb) and KEYTRUDA® (pembrolizumab) (Merck). Exemplary anti-PD-L1 antibodies include, but are not limited to, MPDL3208A (Roche) and MEDI4736 (AstraZeneca).

Exemplary FGFR inhibitors are described in U.S. Publ. No. 2013/0072457 A1 (incorporated herein by reference) and include N-(3,5-dimethoxyphenyl)-N'-(1-methylethyl)-N-[3-(1-methyl-1H-pyrazol-4-yl)quinoxalin-6-yl]ethane-1,2-diamine (referred to herein "JNJ-42756493"), including any tautomeric or stereochemically isomeric forms thereof, N-oxides thereof, pharmaceutically acceptable salts thereof, or solvates thereof (suitable R groups are also disclosed in U.S. Publ. No. 2013/0072457 A1). Thus, in some embodiments, the FGFR inhibitor can be the compound of formula (I):

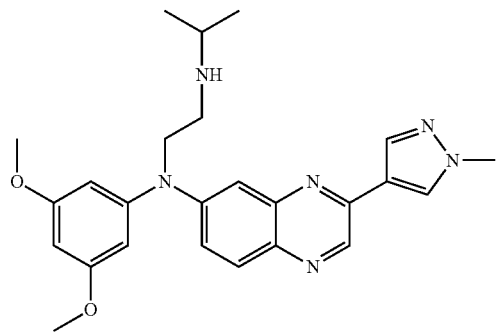

or a pharmaceutically acceptable salt thereof. In some aspects, the pharmaceutically acceptable salt is a HCl salt.

The antibody that blocks the interaction between PD-1 and PD-L1 and the FGFR inhibitor can be administered as a single therapeutic agent or can be co-administered as individual agents. When administered as individual agents, the antibody and FGFR inhibitor can be administered contemporaneously or sequentially in either order. In some embodiments, the antibody that blocks the interaction between PD-1 and PD-L1 and the FGFR inhibitor can be administered contemporaneously. In some embodiments, the antibody that blocks the interaction between PD-1 and PD-L1 can be administered sequentially. In some aspects, for example, the antibody that blocks the interaction between PD-1 and PD-L1 can be administered first, followed by administration of the FGFR inhibitor. In other aspects, the FGFR inhibitor can be administered first, followed by administration of the antibody that blocks the interaction between PD-1 and PD-L1. When administered sequentially, the antibody and FGFR inhibitor can be administered within seconds, minutes, hours, days, or weeks of each other.

The pharmaceutically effective amount of the antibody that blocks the interaction between PD-1 and PD-L1 and FGFR inhibitor will be dependent on several factors including, but not limited to, stage and severity of the cancer, as well as other factors relating to the health of the patient. Those skilled in the art would know how to determine the pharmaceutically effective amount.

The disclosed methods are suitable for treating cancer in a patient if one or more FGFR variants are present in a biological sample from the patient. In some embodiments, the FGFR variant can be one or more FGFR fusion genes. In some embodiments, the FGFR variant can be one or more FGFR mutations. In some embodiments, the FGFR variant can be one or more FGFR amplifications. In some embodiments, a combination of the one or more FGFR variants can be present in the biological sample from the patient. For example, in some embodiments, the FGFR variants can be one or more FGFR fusion genes and one or more FGFR mutations. In some embodiments, the FGFR variants can be one or more FGFR fusion genes and one or more FGFR amplifications. In some embodiments, the FGFR variants can be one or more FGFR mutations and one or more FGFR amplifications. In yet other embodiments, the FGFR variants can be one or more FGFR fusion genes, mutations, and amplifications.

Exemplary FGFR fusion genes are provided in Table 1 and include, but are not limited to: FGFR2:AFF3; FGFR2:BICC1; FGFR2:CASP7; FGFR2:CCDC6; FGFR2:OFD1; FGFR3:BAIAP2L1; FGFR3:TACC3-Intron; FGFR3:

TACC3V1; FGFR3:TACC3V3; or a combination thereof. The sequences of the FGFR fusion genes are disclosed in Table 6.

TABLE 1

Exemplary FGFR fusion genes

| Fusion Gene | FGFR Exon | Partner Exon |
|---|---|---|
| FGFR2 | | |
| FGFR2:AFF3 | 19 | 8 |
| FGFR2:BICC1 | 19 | 3 |
| FGFR2:CASP7 | 19 | 4 |
| FGFR2:CCDC6 | 19 | 2 |
| FGFR2:OFD1 | 19 | 3 |
| FGFR3 | | |
| FGFR3:BAIAP2L1 | 18 | 2 |
| FGFR3:TACC3 Intron | 18 | 4 |
| FGFR3:TACC3 v1 | 18 | 11 |
| FCFR3:TACC3 v3 | 18 | 10 |

The methods can further comprise evaluating the presence of one or more FGFR variants in the biological sample before the administering step. Suitable methods for evaluating a biological sample for the presence of one or more FGFR variants are disclosed elsewhere herein.

The disclosed methods can be dependent upon PD-L1 expression in the cancer or can be carried out irrespectively of PD-L1 expression in the cancer. In some embodiments, for example, the methods can comprise administering to the patient a pharmaceutically effective amount of an antibody that blocks the interaction between PD-1 and PD-L1 and a pharmaceutically effective amount of an FGFR inhibitor, wherein the antibody that blocks the interaction between PD-1 and PD-L1 and the FGFR inhibitor are administered if one or more FGFR variants are present in a biological sample from the patient and PD-L1 expression in the biological sample from the patient is at a specified level or within a specified range. In some aspects, for example, the methods can be carried out if the PD-L1 expression is high in the biological sample. Accordingly, in some embodiments the methods can comprise administering to the patient a pharmaceutically effective amount of an antibody that blocks the interaction between PD-1 and PD-L1 and a pharmaceutically effective amount of an FGFR inhibitor, wherein the antibody that blocks the interaction between PD-1 and PD-L1 and the FGFR inhibitor are administered if PD-L1 expression is high and one or more FGFR variants are present in a biological sample from the patient. Alternatively, the methods can be carried out if the PD-L1 expression is low in the biological sample. Accordingly, the methods can comprise administering to the patient a pharmaceutically effective amount of an antibody that blocks the interaction between PD-1 and PD-L1 and a pharmaceutically effective amount of an FGFR inhibitor, wherein the antibody that blocks the interaction between PD-1 and PD-L1 and the FGFR inhibitor are administered if PD-L1 expression is low and one or more FGFR variants are present in a biological sample from the patient. The methods can be carried out if the PD-L1 expression is moderate. Accordingly, the methods can comprise administering to the patient a pharmaceutically effective amount of an antibody that blocks the interaction between PD-1 and PD-L1 and a pharmaceutically effective amount of an FGFR inhibitor, wherein the antibody that blocks the interaction between PD-1 and PD-L1 and the FGFR inhibitor are administered if PD-L1 expression is moderate and one or more FGFR variants are present in a biological sample from the patient. As discussed elsewhere herein, PD-L1 expression levels can be based upon a numerical H-score (low includes an H-score of about 0 to about 99; moderate includes an H-score of about 100 to about 199; and high includes an H-score of about 200 to about 300) or can be based upon a comparison to a reference value.

In other embodiments, the methods can be carried out irrespectively of PD-L1 expression in the biological sample from the patient and can be based on the presence of one or more FGFR variants without factoring in PD-L1 expression.

The methods can further comprise evaluating PD-L1 expression in the biological sample from the patient. Exemplary methods of evaluating PD-L1 expression are disclosed elsewhere herein. PD-L1 expression can be evaluated before, during, or after the administering step.

In some embodiments, the methods can comprise evaluating the presence of one or more FGFR variants and PD-L1 expression in the biological sample from the patient before the administering step.

Suitable biological samples evaluating PD-L1 expression, evaluating the presence of one or more FGFR variants, or for evaluating both PD-L1 expression and the presence of one or more FGFR variants include, but are not limited to, blood, lymph fluid, bone marrow, a solid tumor sample, or any combination thereof.

The disclosed methods can be used to treat a variety of cancer types including, but not limited to, lung cancer, bladder cancer, gastric cancer, breast cancer, ovarian cancer, head and neck cancer, esophageal cancer, glioblastoma, or any combination thereof. In some embodiments, the methods can be used to treat lung cancer. The lung cancer can be non-small cell lung cancer (NSCLC) adenocarcinoma, NSCLC squamous cell carcinoma, small cell lung cancer, or any combination thereof. Thus, in some aspects, the methods can be used to treat NSCLC adenocarcinoma. In other aspects, the methods can be used to treat NSCLC squamous cell carcinoma. In yet other aspects, the methods can be used to treat small cell lung cancer. In some embodiments, the methods can be used to treat bladder cancer. In some embodiments, the methods can be used to treat gastric cancer. In some embodiments, the methods can be used to treat breast cancer. In some embodiments, the methods can be used to treat ovarian cancer. In some embodiments, the methods can be used to treat head and neck cancer. In some embodiments, the methods can be used to treat esophageal cancer. In some embodiments, the methods can be used to treat glioblastoma. In some embodiments, the methods can be used to treat any combination of the above cancers.

Also disclosed are methods of treating cancer in a patient comprising: administering to the patient a pharmaceutically effective amount of an antibody that blocks the interaction between PD-1 and PD-L1; monitoring the efficacy of the antibody; and if the antibody is not efficacious, evaluating a biological sample from the patient for a presence of one or more FGFR variants and administering to the patient a pharmaceutically effective amount of an FGFR inhibitor if the one or more FGFR variants are present in the sample.

The efficacy of the antibody can be monitored by, for example, evaluating the patient's symptoms for progression of the cancer, evaluating the severity of the cancer symptoms, evaluating the frequency of the cancer symptoms, measuring tumor size, or any combination thereof. Without intent to be limiting, progression or failure to reduce the progression of the cancer, increased severity or no change in severity of the cancer symptoms, increased frequency or no change in the frequency of the cancer symptoms, increased size or no change in size of the tumor, or any combination thereof, can be indications that the antibody is not efficacious.

In some embodiments, the methods can comprise administering to the patient a pharmaceutically effective amount of an anti-PD-1 antibody. In some embodiments, the methods can comprise administering to the patient a pharmaceutically effective amount of an anti-PD-L1 antibody. In some embodiments, the methods can comprise administering to the patient a pharmaceutically effective amount of an anti-PD-1 antibody and an anti-PD-L1 antibody. Exemplary anti-PD-1 antibodies include, but are not limited to, OPDIVO® (nivolumab) (Bristol-Myers Squibb) and KEYTRUDA® (pembrolizumab) (Merck). Exemplary anti-PD-L1 antibodies include, but are not limited to, MPDL3208A (Roche) and MEDI4736 (AstraZeneca).

Exemplary FGFR inhibitors include those disclosed above, including N-(3,5-dimethoxyphenyl)-N'-(1-methylethyl)-N-[3-(1-methyl-1H-pyrazol-4-yl)quinoxalin-6-yl]ethane-1,2-diamine (referred to herein "JNJ-42756493"), including any tautomeric or stereochemically isomeric forms thereof, N-oxides thereof, pharmaceutically acceptable salts thereof, or solvates thereof (suitable R groups are also disclosed in U.S. Publ. No. 2013/0072457 A1). In some embodiments, the FGFR inhibitor can be the compound of formula (I):

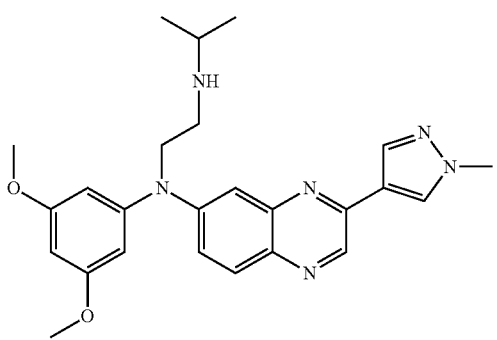

or a pharmaceutically acceptable salt thereof. In some aspects, the pharmaceutically acceptable salt is a HCl salt.

The pharmaceutically effective amount of the antibody and FGFR inhibitor will be dependent on several factors including, but not limited to, stage and severity of the cancer, as well as other factors relating to the health of the patient. Those skilled in the art would know how to determine the pharmaceutically effective amount.

The disclosed methods are suitable for treating cancer in a patient if one or more FGFR variants are present in a biological sample from the patient. In some embodiments, the FGFR variant can be one or more FGFR fusion genes. In some embodiments, the FGFR variant can be one or more FGFR mutations. In some embodiments, the FGFR variant can be one or more FGFR amplifications. In some embodiments, a combination of the one or more FGFR variants can be present in the biological sample from the patient. For example, in some embodiments, the FGFR variants can be one or more FGFR fusion genes and one or more FGFR mutations. In some embodiments, the FGFR variants can be one or more FGFR fusion genes and one or more FGFR amplifications. In some embodiments, the FGFR variants can be one or more FGFR mutations and one or more FGFR amplifications. In yet other embodiments, the FGFR variants can be one or more FGFR fusion genes, mutations, and amplifications. Exemplary FGFR fusion genes are provided in Table 1 and include, but are not limited to: FGFR2:AFF3; FGFR2:BICC1; FGFR2:CASP7; FGFR2:CCDC6; FGFR2:OFD1; FGFR3:BAIAP2L1; FGFR3:TACC3-Intron; FGFR3:TACC3V1; FGFR3:TACC3V3; or a combination thereof.

Suitable methods for evaluating a biological sample for the presence of one or more FGFR variants are disclosed elsewhere herein.

The disclosed methods can be dependent upon PD-L1 expression in the biological sample or can be carried out irrespectively of PD-L1 expression in the cancer. In some aspects, for example, if the antibody is not efficacious, the methods can comprise measuring an expression level of PD-L1 in the biological sample and administering to the patient a pharmaceutically effective amount of an FGFR inhibitor if the PD-L1 expression is at a specified level or within a specified range. Methods of evaluating PD-L1 expression are disclosed elsewhere herein. The methods can be carried out if the PD-1 expression in the biological sample is low. In some embodiments, for example, the evaluating step can further comprise measuring an expression level of PD-L1 in the biological sample and the second administering step can comprise administering the FGFR inhibitor if the expression level of PD-L1 is low. In some aspects, methods of treating cancer in a patient comprise: administering to the patient a pharmaceutically effective amount of an antibody that blocks the interaction between PD-1 and PD-L1; monitoring the efficacy of the antibody; and if the antibody is not efficacious, evaluating a biological sample from the patient for a presence of one or more FGFR variants and measuring an expression level of PD-L1 in the biological sample, and administering to the patient a pharmaceutically effective amount of an FGFR inhibitor if the one or more FGFR variants are present and if the expression level of PD-L1 is low in the sample.

The methods can be carried out if the PD-1 expression in the biological sample is moderate. Thus, the evaluating step can further comprise measuring an expression level of PD-L1 in the biological sample and the second administering step can comprise administering the FGFR inhibitor if the expression level of PD-L1 is moderate. The methods can be carried out if the PD-1 expression in the biological sample is high. For example, the evaluating step can further comprise measuring an expression level of PD-L1 in the biological sample and the second administering step can comprise administering the FGFR inhibitor if the expression level of PD-L1 is high.

As discussed elsewhere herein, PD-L1 expression levels can be based upon a numerical H-score (low includes an H-score of about 0 to about 99; moderate includes an H-score of about 100 to about 199; and high includes an H-score of about 200 to about 300) or can be based upon a comparison to a reference value.

In other embodiments, the methods can be carried out irrespectively of PD-L1 expression in the cancer and can be based on the presence of one or more FGFR variants in the biological sample without factoring in PD-L1 expression.

Suitable biological samples include, but are not limited to, blood, lymph fluid, bone marrow, a solid tumor sample, or any combination thereof.

The disclosed methods can be used to treat a variety of cancer types including, but not limited to, lung cancer, bladder cancer, gastric cancer, breast cancer, ovarian cancer, head and neck cancer, esophageal cancer, glioblastoma, or any combination thereof. In some embodiments, the methods can be used to treat lung cancer. The lung cancer can be non-small cell lung cancer (NSCLC) adenocarcinoma, NSCLC squamous cell carcinoma, small cell lung cancer, or any combination thereof. Thus, in some aspects, the methods can be used to treat NSCLC adenocarcinoma. In other aspects, the methods can be used to treat NSCLC squamous cell carcinoma. In yet other aspects, the methods can be used to treat small cell lung cancer. In some embodiments, the methods can be used to treat bladder cancer. In some embodiments, the methods can be used to treat gastric cancer. In some embodiments, the methods can be used to treat breast cancer. In some embodiments, the methods can be used to treat ovarian cancer. In some embodiments, the methods can be used to treat head and neck cancer. In some embodiments, the methods can be used to treat esophageal cancer. In some embodiments, the methods can be used to treat glioblastoma. In some embodiments, the methods can be used to treat any combination of the above cancers.

Evaluating a Sample for the Presence of One or More FGFR Variants

The following methods for evaluating a biological sample for the presence of one or more FGFR variants apply equally to any of the above disclosed methods of treatment.

Suitable methods for evaluating a biological sample for the presence of one or more FGFR variants are described in the methods section herein and in U.S. Provisional Patent App. No. 62/056,159, which is incorporated herein in its entirety. For example, and without intent to be limiting, evaluating a biological sample for the presence of one or more FGFR variants can comprise any combination of the following steps: isolating RNA from the biological sample; synthesizing cDNA from the RNA; and amplifying the cDNA (preamplified or non-preamplified). In some embodiments, evaluating a biological sample for the presence of one or more FGFR variants can comprise: amplifying cDNA from the patient with a pair of primers that bind to and amplify one or more FGFR variants; and determining whether the one or more FGFR variants are present in the sample. In some aspects, the cDNA can be pre-amplified. In some aspects, the evaluating step can comprise isolating RNA from the sample, synthesizing cDNA from the isolated RNA, and pre-amplifying the cDNA.

Suitable primer pairs for performing an amplification step include, but are not limited to, those disclosed in U.S. Provisional Patent App. No. 62/056,159, as exemplified below:

| | | |
|---|---|---|
| FGFR3TACC3 V1 | Forward: | GACCTGGACCGTGTCCTTACC (SEQ ID NO: 1) |
| | Reverse: | CTTCCCCAGTTCCAGGTTCTT (SEQ ID NO: 2) |
| FGFR3TACC3 V3 | Forward: | AGGACCTGGACCGTGTCCTT (SEQ ID NO: 3) |
| | Reverse: | TATAGGTCCGGTGGACAGGG (SEQ ID NO: 4) |
| FGFR3TACC3 Intron | Forward: | GGCCATCCTGCCCCC (SEQ ID NO: 5) |
| | Reverse: | GAGCAGTCCAGGTCAGCCAG (SEQ ID NO: 6) |
| FGFR3BAIAP2L1 | Forward: | CTGGACCGTGTCCTTACCGT (SEQ ID NO: 7) |
| | Reverse: | GCAGCCAGGATTGAACTGT (SEQ ID NO: 8) |
| FGFR2BICC1 | Forward: | TGGATCGAATTCTCACTCTCACA (SEQ ID NO: 9) |
| | Reverse: | GCCAAGCAATCTGCGTATTTG (SEQ ID NO: 10) |
| FGFR2AFF3 | Forward: | TGGTAGAAGACTTGGATCGAATTCT (SEQ ID NO: 11) |
| | Reverse: | TCTCCCGGATTATTTCTTCAACA (SEQ ID NO: 12) |
| FGFR2CASP7 | Forward: | GCTCTTCAATACAGCCCTGATCA (SEQ ID NO: 13) |
| | Reverse: | ACTTGGATCGAATTCTCACTCTCA (SEQ ID NO: 14) |
| FGFR2CCDC6 | Forward: | TGGATCGAATTCTCACTCTCACA (SEQ ID NO: 15) |
| | Reverse: | GCAAAGCCTGAATTTTCTTGAATAA (SEQ ID NO: 16) |
| FGFR2OFD1 | Forward: | AGGGTGCATCAACTCATGAATTAG (SEQ ID NO: 17) |
| | Reverse: | ACTTGGATCGAATTCTCACTCTCA (SEQ ID NO: 18) |

The presence of one or more FGFR variants can be evaluated at any suitable time point including upon diagnosis, following tumor resection, following first-line therapy, during clinical treatment, or any combination thereof.

Evaluating PD-L1 Expression in the Cancer

The following methods for evaluating PD-L1 expression in a biological sample apply equally to any of the above disclosed methods of treatment.

In some embodiments, the disclosed methods can be dependent upon PD-L1 expression in the biological sample from the patient. Thus, administering to the patient a pharmaceutically effective amount of an antibody that blocks the interaction between PD-1 and PD-L1 and a pharmaceutically effective amount of an FGFR inhibitor may be based upon PD-L1 expression and the presence of one or more FGFR variants in the biological sample from the patient. The methods can comprise evaluating PD-L1 expression in a biological sample from the patient. The biological sample from which PD-L1 expression is evaluated can be the same biological sample from which the presence of one or more FGFR variants are evaluated, or the biological samples from which PD-L1 expression is evaluated can be a different biological sample from which the presence of one or more FGFR variants are evaluated. "Same biological sample" refers to a single sample from which both PD-L1 expression and FGFR variants are evaluated. "Different biological sample" includes the same source of sample (blood, lymph fluid, bone marrow, a solid tumor sample, etc.) taken at different time points or different sources of sample. For example, a blood sample can be obtained from the patient, evaluated for PD-L1 expression or the presence of one or more FGFR variants, and at a later time point, another blood sample can be obtained from the patient and evaluated for the presence of one or more FGFR variants or PD-L1 expression. Conversely, a blood sample can be obtained from the patient and evaluated for PD-L1 expression and/or the presence of one or more FGFR variants and a solid tumor sample can be obtained from the patient and evaluated for the presence of one or more FGFR variants and/or PD-L1 expression.

In some embodiments, the level of PD-L1 expression can be converted into a numerical H-score (as described in the methods section herein). The level of PD-L1 expression can be converted into a numerical H-score of: low PD-L1 expression, which includes an H-score of about 0 to about 99; moderate PD-L1 expression, which includes an H-score of about 100 to about 199; or high PD-L1 expression, which includes an H-score of about 200 to about 300. Treating the patient can be based upon these H-scores. For example, if the treatment methods are carried out on a patient with a low H-score, that patient would have PD-L1 expression corresponding to an H-score of about 0 to about 99. If the treatment methods are carried out on a patient with a moderate H-score, that patient would have PD-L1 expression corresponding to an H-score of about 100 to about 199. If the treatment methods are carried out on a patient with a high H-score, that patient would have PD-L1 expression corresponding to an H-score of about 200 to about 300.

In other embodiments, the level of PD-L1 expression can be compared to a reference PD-L1 expression level. In a preferred embodiment, the reference PD-L1 expression level can be predetermined. For example, a reference data set may be established using samples from unrelated patients with low, moderate and high PD-L1 expression levels. This data set can represent a standard by which relative PD-L1 expression levels are compared among patients and/or quantified using the H-Score method. In some embodiments, the reference PD-L1 expression level can be determined by comparing a patient population that is administered the antibody that blocks the interaction between PD-1 and PD-L1 to a patient population that is administered placebo. The PD-L1 expression level for each patient in the respective populations can be determined in accordance with the methods described herein. Clinical outcomes (e.g., progression-free survival or overall survival) for the patient populations can be monitored. Clinical outcomes for the patient populations relative to PD-L1 expression levels can then be compared. The reference PD-L1 expression level can correspond to the PD-L1 expression level above which the patient population that is administered the antibody that blocks the interaction between PD-1 and PD-L1 demonstrates a statistically significant improvement in at least one clinical outcome relative to the patient population that is administered placebo. A patient PD-L1 expression level that is less than the reference PD-L1 expression level, particularly when combined with the presence of one or more FGFR variants in a patient sample, can be indicative that the patient will benefit from treatment with the antibody that that blocks the interaction between PD-1 and PD-L1 in combination with an FGFR inhibitor. For example, in some embodiments, the methods can comprise administering an antibody that blocks the interaction between PD-1 and PD-L1 and an FGFR inhibitor, wherein the antibody that blocks the interaction between PD-1 and PD-L1 and the FGFR inhibitor are administered if one or more FGFR variants are present in a biological sample from the patient and the PD-L1 expression in the biological sample is less than a reference PD-L1 expression level, wherein the reference PD-L1 expression level corresponds to a PD-L1 expression level above which treatment with the antibody that blocks the interaction between PD-1 and PD-L1 alone is likely to be efficacious.

Methods for determining PD-L1 expression include, but are not limited to, immunohistochemistry (IHC), Western Blotting, microscopy, immunoprecipitation, BCA assays, spectrophotometry, or any combination thereof. Exemplary methods for evaluating PD-L1 expression are described in the methods section herein.

PD-L1 expression can be evaluated at any suitable time point including upon diagnosis, following tumor resection, following first-line therapy, during clinical treatment, or any combination thereof.

The following examples are provided to further describe some of the embodiments disclosed herein. The examples are intended to illustrate, not to limit, the disclosed embodiments.

EXAMPLES

Methods

PD-L1 Immunohistochemistry

PD-L1 immunohistochemistry (IHC) was performed at a CRO (QualTek, Newtown, Pa.). Samples were stained using a CD274 PD-L1 (RUO) assay. Slides stained with a CD274 PD-L1 (RUO) assay were examined in random order and/or in blinded fashion by a board-certified clinical pathologist, the Medical Director of QualTek Clinical Laboratories (CAP/CLIA facility). The entire tissue section was evaluated for CD274 PD-L1. Only viable tissue was evaluated; areas of necrosis or obviously poorly fixed areas of tissue were not evaluated.

The tumor H-Score was calculated from the intensity of CD274 PD-L1 membrane reactivity on a four-point semi-quantitative scale (0: null, negative or non-specific staining of cell membranes; 1+: low or weak intensity staining of cell membranes; 2+: medium or moderate intensity staining of cell membranes; and 3+: high or strong intensity staining of cell membranes) and the estimated percentage of CD274 PD-L1 positive tumor cells (0-100%) for each discrete intensity value.

Tumor CD274 PD-L1 membrane reactivity was captured by a standard H-Score–the tumor H-Score minimum of 0 and the tumor H-Score maximum of 300: Tumor H-Score= ([% positive cells at 1+]*1)+([% positive cells at 2+]*2)+ ([% positive cells at 3+]*3)

Next-Generation Sequencing (NGS)

NGS for FGFR mutations and gene amplification was performed by Foundation Medicine, Cambridge, Mass. using the FoundationOne panel (http://www.foundation-medicine.com).

FGFR Fusions

FGFR fusions were determined using a proprietary qRT-PCR assay developed by Janssen Oncology Translational Research as described in U.S. Provisional Application No. 62/056,159.

Results

PD-L1 Expression in Tumors with FGFR Fusions and Mutations

To determine the overlap of PD-L1 expression with FGFR alterations, immunohistochemistry (IHC) for PD-L1 was performed on human tumor tissue samples which were subsequently assessed for FGFR alterations. FGFR amplifications and mutations were identified using next-generation sequencing (Foundation Medicine panel, FMI). FGFR fusions were screened for using a Janssen-developed qRT-PCR assay.

Correlation of FGFR Mutations and Amplification with PD-L1

PD-L1 expression was first assessed in a set of 120 commercially sourced lung FFPE tumor tissues comprised of forty of each of the following lung tumor histologies; non-small-cell lung carcinoma (NSCLC) adenocarcinoma; NSCLC squamous cell carcinoma; and small-cell lung cancer (SCLC). FGFR mutations and gene amplification were detected using the Foundation Medicine panel. PD-L1 staining versus FGFR status was plotted for each tumor type (FIG. 1). PD-L1 expression was largely reserved to tumors without FGFR mutations or amplifications. Out of nine samples with FGFR mutations, no PD-L1 staining was observed in seven samples (78%). Two of the nine samples showed very low PD-L1 staining with H-scores of 20 and 70, respectively. Of four samples with FGFR gene amplification, one sample showed moderate-high PD-L1 staining (H-score=140), with three having almost no staining (H-score=4, n=1). No staining was observed in the one tumor sample harboring both an FGFR mutation and FGFR gene amplification. FGFR mutation and amplification status was unknown for 24 tumor samples, of which nine exhibited PD-L1 staining with H-scores ranging from 55 to 220.

FGFR Fusions and PD-L1 Expression in Bladder and NSCLC

Figure 2:
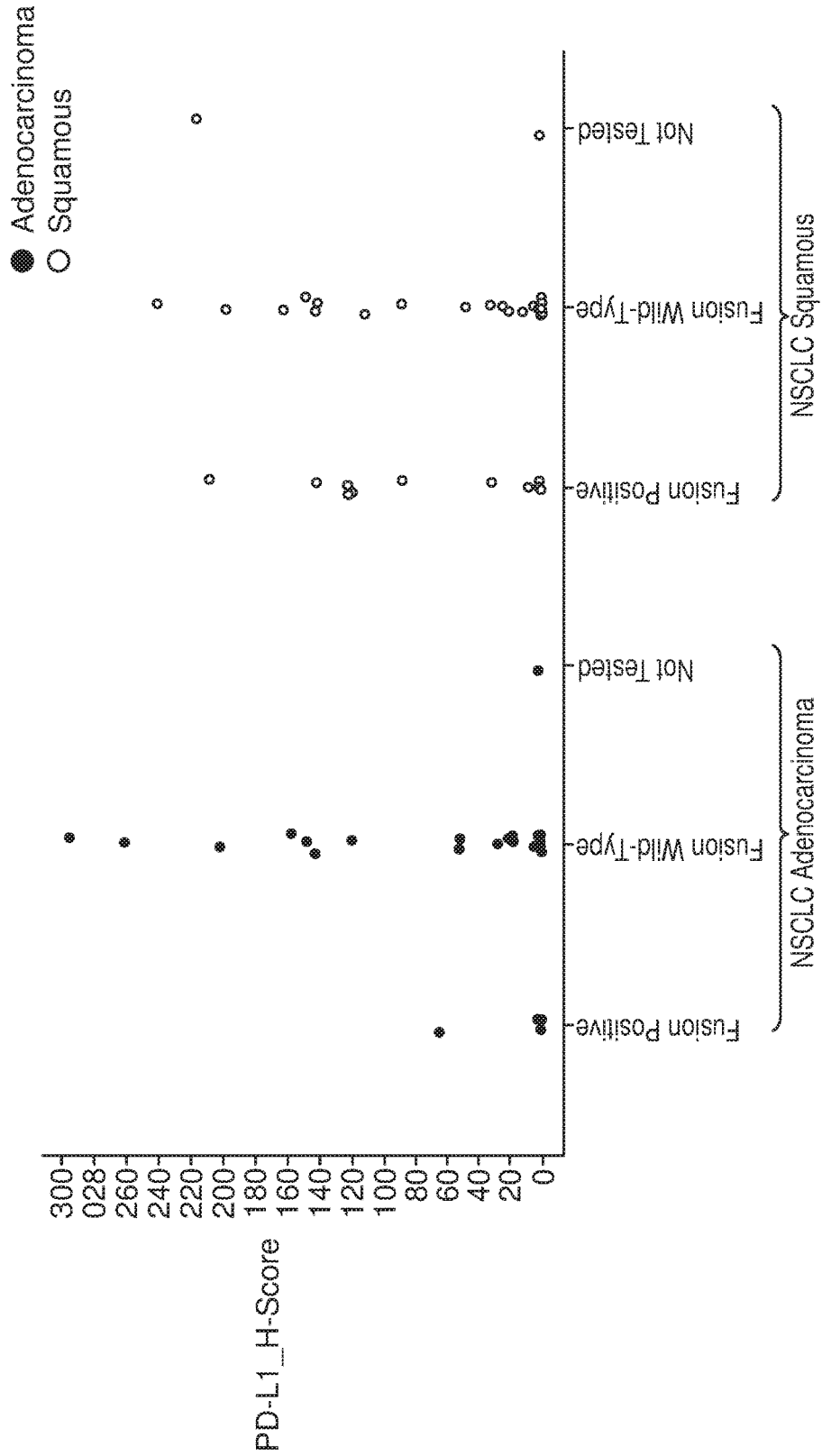
FIG. 2 illustrates PD-L1 expression in an 80 non-small-cell lung carcinoma (NSCLC) sample set by FGFR fusion status by NSCLC histology. PD-L1 H-scores (Y-axis) were plotted for NSCLC adenocarcinoma (left), and NSCLC squamous (right). The FGFR fusion status versus the PD-L1 staining for each of the 80 samples is shown. Fusion Positive—an FGFR fusion was detected; Fusion Wild-Type—no FGFR fusion was detected; Not Tested—insufficient sample for testing or QC failure.

The set of 120 lung FFPE tumor tissues was subsequently screened for FGFR fusions using a Janssen-developed qRT-PCR assay (as described in U.S. Provisional Application No. 62/056,159) detecting nine fusions (Table 1). Results for PD-L1 expression by FGFR fusion status for the NSCLC tumor samples (n=80) are shown in FIG. 2. Twenty-three percent (7/31) of NSCLC adenocarcinoma samples, and 52% (13/25) of NSCLC squamous cell carcinoma tumor samples were positive for FGFR fusions. All fusion-positive adenocarcinoma samples exhibited no or low PD-L1 expression, 6/7 (86%) or 1/7 (14%), respectively (Table 2). Fusion-negative adenocarcinoma samples showed a range of PD-L1 from no expression (12/31, 39%), low (12/31, 39%), moderate (4/31, 13%), to high PD-L1 (3/31, 10%) (Table 2). Fusion-positive squamous cell carcinoma sample PD-L1 H-scores were equally distributed across the no expression, low, moderate, or high expression categories (4/31, 31% each respectively) (Table 3). Fusion-negative squamous samples also showed a range of H-scores from no expression (6/25, 24%), low (11/25, 44%), moderate (5/25, 20%), and high expression (3/25, 12%) (Table 3).

TABLE 2

NSCLC Adenocarcinoma - PD-L1 H-Scores by FGFR fusion status

| NSCLC Adeno-carcinoma | H-Score Range | | | | | |
|---|---|---|---|---|---|---|
| | 0 | 1-25 | 26-50 | 51-99 | 100-199 | 200-300 |
| Category: | No | | Low | | Mod. | High |
| Fusion Positive | 6 (86%) | — | — | 1 (14%) | — | — |
| Fusion Negative | 12 (39%) | 9 (29%) | 2 (6%) | 1 (3%) | 4 (13%) | 3 (10%) |

TABLE 3

NSCLC Squamous Cell Carcinoma - PD-L1 H-Scores by FGFR fusion status

| NSCLC Squamous | H-Score Range | | | | | |
|---|---|---|---|---|---|---|
| | 0 | 1-25 | 26-50 | 51-99 | 100-199 | 200-300 |
| Category: | No | | Low | | Mod. | High |
| Fusion Positive | 4 (31%) | 2 (15%) | 1 (8%) | 1 (8%) | 4 (31%) | 1 (8%) |
| Fusion Negative | 6 (24%) | 8 (32%) | 2 (8%) | 1 (4%) | 5 (20%) | 3 (12%) |

Forty-five commercially sourced bladder tumors were sequenced for mutations by the Foundation Medicine panel (FMI), stained for PD-L1 expression, and screened for FGFR gene fusions using the Janssen qRT-PCR assay. Forty-two of 45 samples (93%) were positive for FGFR fusions. Five samples (11%) were positive for an FGFR mutation (FGFR3-R248C or FGFR3-S249C), all of which were also positive for FGFR fusions. PD-L1 staining H-scores for samples with FGFR alterations are summarized in Table 4, and listed in Table 5. For FGFR fusion positive samples, 22/37 (59%) were negative for PD-L1 staining. Ten FGFR fusion-positive samples (27%) expressed low levels of PD-L1, and five samples (14%) showed high PD-L1 expression. All samples with both FGFR mutations and FGFR fusions in the same tumor sample (n=5) were negative for PD-L1 staining. Overall, PD-L1 staining was absent in 64% (27/42) of bladder samples with FGFR alterations, keeping in mind that almost all of the tumors in this sample set were positive for FGFR fusions.

FGFR mutation and PD-L1 expression data were available for seven commercially sourced metastatic NSCLC samples with FGFR fusions (Janssen). No PD-L1 staining was observed in 4/7 (57%) of samples. Two samples exhibited very low PD-L1 staining, H-scores of 4 and 15. One sample showed moderate PD-L1 with an H-score of 160. Interestingly, the FGFR fusion-positive sample with moderate PD-L1 staining harbored an FGFR4 V550I mutation—an FGFR gatekeeper residue mutation with potential to confer resistance to tyrosine kinase inhibitors.

Overall these data show that the majority of commercially available tumor samples harboring FGFR alterations have very little expression or do not express PD-L1.

TABLE 4

PD-L1 staining in FGFR fusion positive bladder samples

| n = 42 | H-Score Range | | | | | |
|---|---|---|---|---|---|---|
| | 0 | 1-25 | 26-50 | 51-99 | 100-199 | 200-300 |
| Category: | No | | Low | | Mod. | High |
| Fusion Positive | 22 | 8 | — | 2 | — | 5 |
| Fusion + Mutation | 5 | — | — | — | — | — |
| % of Total FGFR + Samples Expressing per Category | 64% | 19% | 0% | 5% | 0% | 12% |

TABLE 5

PD-L1 expression, FGFR fusion and mutation status in commercial bladder and NSCLC tumor samples

| Janssen Sample ID | Tumor Type | FGFR Fusion Gene(s) | FGFR Mutation | H-Score (0-300) |
|---|---|---|---|---|
| 2329 | Bladder | None | None | 300 |
| 2425 | Bladder | FGFR3:BAIA/FGFR2:CASP7/FGFR2:OFD1 | None | 300 |
| F26993.C3a | Bladder | FGFR3:BAIA/FGFR2:AFF/FGFR2:CASP7/FGFR2:CCDC6 | None | 300 |
| F5244.E22b | Bladder | FGFR2:CASP7 | None | 300 |
| F28052.E14a | Bladder | FGFR2:BICC1/FGFR2:AFF3/FGFR2:CCDC6 | None | 280 |
| F27999.D25 | Bladder | FGFR3:BAIA/FGFR2:CCDC6 | None | 250 |
| F7799.H25b | Bladder | FGFR3:BAIAP2L/FGFR2:CASP7/FGFR2:OFD | None | 70 |
| F28057.D1a | Bladder | FGFR3:BAIA | None | 60 |
| F15377.A2 | Bladder | FGFR2:AFF3 | None | 21 |
| F28137.G3b | Bladder | FGFR3:TACC3v3/FGFR2:AFF3 | None | 20 |
| F7538.A1b | Bladder | FGFR3:BAIAP2L/FGFR2:BICC1/FGFR:AFF3/FGFR2:CASP7 | None | 20 |
| F26375.A2 | Bladder | FGFR3:BAIA/FGFR2:AFF/FGFR2:CASP7 | None | 18 |
| F7830.G3ba | Bladder | FGFR2:CASP7 | None | 10 |
| F7860.B2b | Bladder | FGFR2:AFF3FGFR2:CASP7 | None | 10 |
| F27338.C4a | Bladder | FGFR3:BAIA/FGFR2:CASP7 | None | 6 |
| F5242.G10ba | Bladder | FGFR2:CASP7 | None | 3 |
| 2319 | Bladder | FGFR2:CASP7 | None | 0 |
| 2321 | Bladder | None | None | 0 |
| 2346 | Bladder | FGFR3:BAIA/FGFR2:CASP7/FGFR2:OFD1 | None | 0 |
| 2347 | Bladder | FGFR3:BAIAP2L1/FGFR2:CCDC6 | FGFR3-S249C | 0 |
| 2362 | Bladder | FGFR3:TACC3v1/FGFR3:TACC3v3/FGFR3:BAIA/FGFR2:BICC1/FGFR2:AFF/FGFR2:CASP7/FGFR2:CCDC6 | FGFR3-S249C | 0 |
| 2376 | Bladder | FGFR3:TACC3,v1/FGFR2:BICC1/FGFR2:CASP7 | None | 0 |
| 2381 | Bladder | FGFR3:BAIA/FGFR2:AFF3/FGFR2:CASP7 | FGFR3-R248C FGFR3-S249C | 0 |
| 2430 | Bladder | FGFR3:BAIA/FGFR2:CASP7 | None | 0 |
| 2434 | Bladder | FGFR3:BAIA | None | 0 |
| 2458 | Bladder | FGFR3:BAIA/FGFR2:AFF3/FGFR2:CASP7 | FGFR3-R248C | 0 |
| 2455 | Bladder | None | None | 0 |
| 2473 | Bladder | FGFR2:AFF3/FGFR2:OFD1 | None | 0 |
| 2480 | Bladder | FGFR2:OFD1 | None | 0 |
| 2518 | Bladder | FGFR3:BAIA/FGFR2:AFF3/FGFR2:CASP7/FGFGFR2:OFD1 | None | 0 |
| 2533 | Bladder | FGFR2:OFD1 | None | 0 |
| 2541 | Bladder | FGFR2:CASP7/FGFR2:OFD1 | None | 0 |
| 2561 | Bladder | FGFR3:BAIA/FGFR2:BICC1/FGFR2:AFF3/FGFR2:CASP7 | None | 0 |
| 2563 | Bladder | FGFR2:OFD1 | None | 0 |
| 4916 | Bladder | FGFR2:OFD1 | None | 0 |
| F27064.CFS | Bladder | FGFR3:BAIA/FGFR2:AFF/FGFR2:CASP7 | None | 0 |
| F28132.Ba | Bladder | FGFR3:TACC3v1/FGFR3:BAIAP2L/FGFR2:BICC1/FGFR2:CCDC6 | None | 0 |
| F7269.C2 | Bladder | FGFR3:BAIAP2L/FGFR2:CASP7 | None | 0 |
| F7271.AFSb | Bladder | FGFR2:AFF3/FGFR2:CASP7 | None | 0 |
| F7467.D1bb | Bladder | FGFR2:AFF3/FGFR2:CASP7/FGFR2:CCDC6 | None | 0 |
| F7484.BFSc | Bladder | FGFR2:AFF3 | None | 0 |
| F7502.D1b | Bladder | FGFR2:AFF3/FGFR2:CASP7 | FGFR3-S249C | 0 |
| F7789.DFSb | Bladder | FGFR3:BAIAP2L/FGFR2:CASP7 | FGFR2-M537I | 0 |
| F7876.D1bb | Bladder | FGFR3:BAIAP2L/FGFR2:OFD1 | None | 0 |
| I-7290.E13a | Bladder | FGFR2:CASP7 | None | 0 |
| CNT06GK | NSCLC | FGFR3:TACC3intron | FGFR4-V550I | 160 |
| CNT0RHX | NSCLC | FGFR3:BAIAP2L | None | 15 |
| CNT0RFD | NSCLC | FGFR2:BICC1 | None | 4 |
| CNT06FI | NSCLC | FGFR2:AFF3 | None | 0 |
| CNT06FJ | NSCLC | FGFR2:CCDC6 | None | 0 |
| CNT06G5 | NSCLC | FGFR3:TACC3v1/FGFR3:TACC3intron/FGFR2:AFF3 | None | 0 |
| CNT0RFX | NSCLC | FGFR3:BAIAP2L/FGFR2:CASP7 | None | 0 |

FGFR in Vitro Experiments

Figure 3:
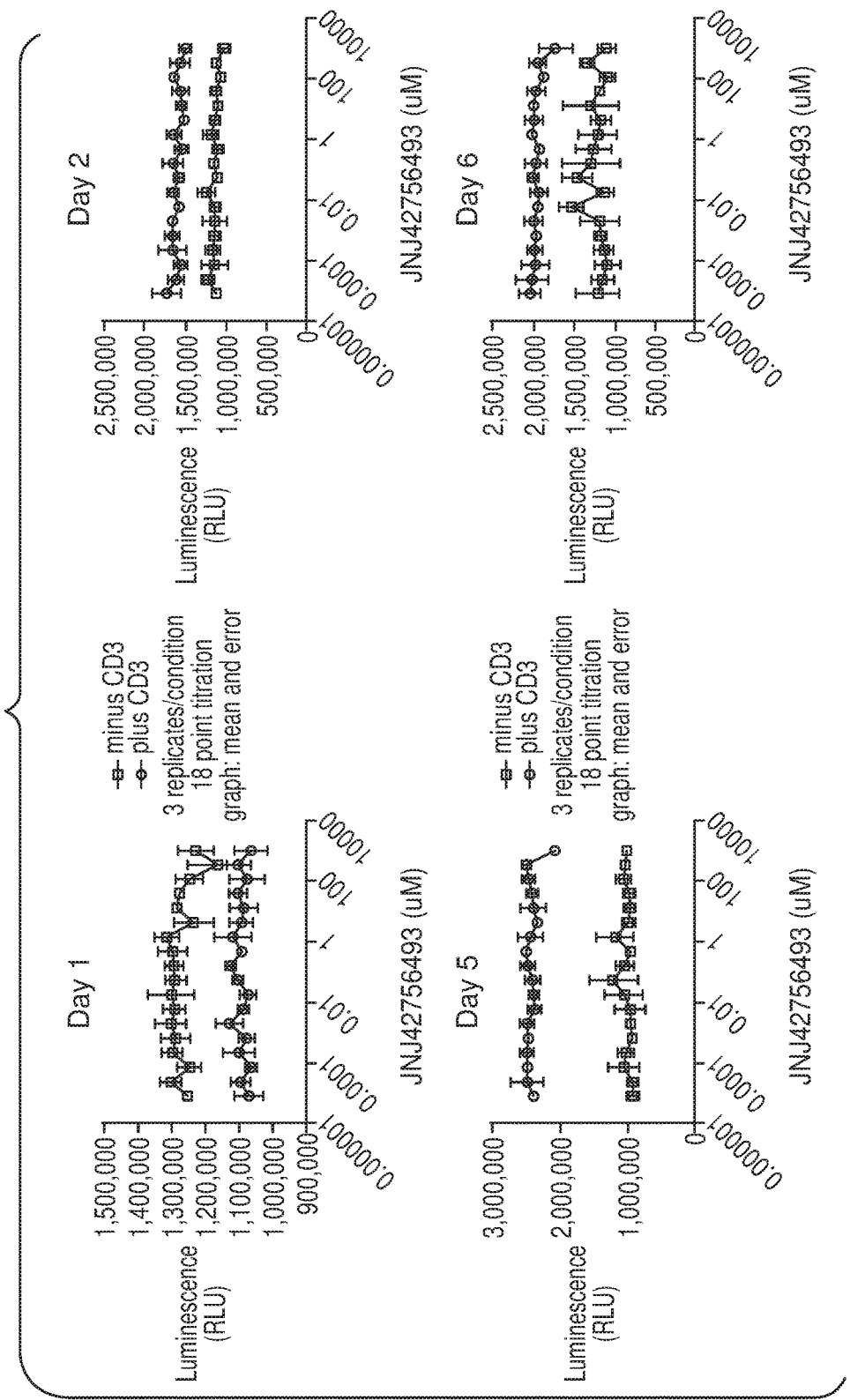
FIG. 3 illustrates the effect of JNJ42756493 on immune cell viability. Normal donor peripheral blood mononuclear cells (PBMCs), either unstimulated or stimulated with anti-CD3 antibodies, were treated with increasing concentrations of JNJ42756493 (0.0000077, 0.000023, 0.000070, 0.00021, 0.00063, 0.00188, 0.00565, 0.01694, 0.051, 0.152, 0.457, 1.372, 4.115, 12.346, 37.037, 111.111, 333.333, and 1000 nM). On days 1, 2, 5 and 6 after plating, cell viability was assessed by CellTiter-Glo (Promega).

To determine the effects of JNJ427564493 on immune cell viability in vitro, peripheral blood mononuclear cells (PBMCs) from normal donors were stimulated with anti-CD3 antibodies to activate T cells, in the presence of increasing concentrations of JNJ42756493. Unstimulated PBMCs were also included to determine if JNJ42756493 affected unactivated immune populations. Cell viability was assessed at four different time points, over 6 days. FIG. 3 shows the luminescence signal, as a measurement of cell viability, in the presence of increasing concentrations of JNJ42756493 (up to 1 μM) at days 1, 2, 5 and 6 post-treatment. For both the stimulated and unstimulated groups, at all time points tested, cell viability remained constant with increasing concentrations of compound. These data suggest that the addition of JNJ42756493 does not impair immune cell viability.

Figure 4:
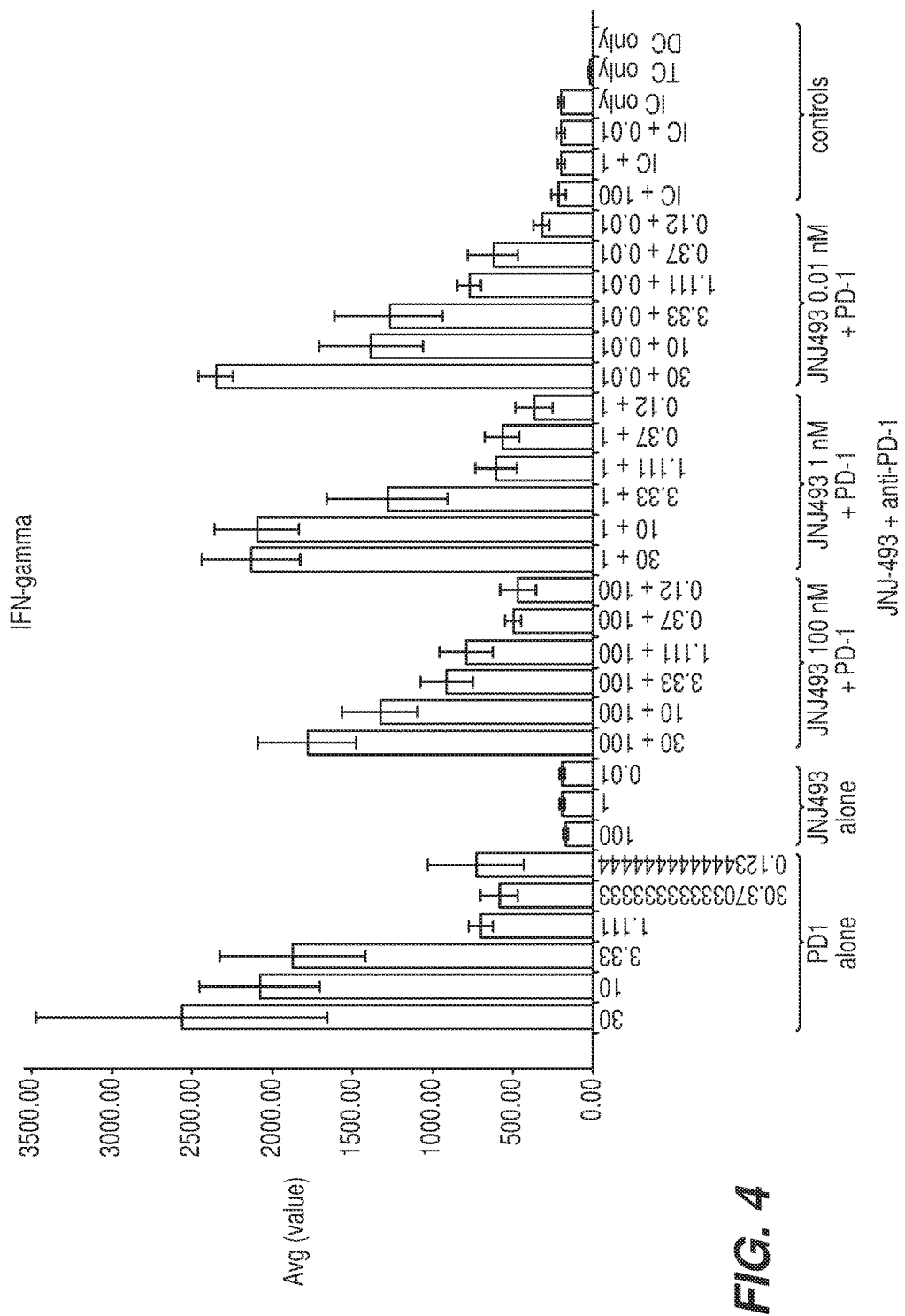
FIG. 4 illustrates the effect of JNJ42756493 on IFN-γ levels induced by anti-PD-1 antibodies in a Mixed Lymphocyte Reaction (MLR) Assay. Cultures of $CD4^+$ T and allogeneic dendritic cells were treated with anti-PD-1 antibodies (concentrations left to right—30, 10, 3.33, 1.11, 0.37, 0.12 nM). JNJ42756493 was added at 100, 1, or 0.01 nM alone (concentrations left to right), together with anti-PD-1 antibodies (100, 1, or 0.01 nM JNJ42756493 together with 30, 10, 3.33, 1.11, 0.37, or 0.12 nM of anti-PD-1 antibody), or in the presence of isotype control (IC). 5 days after treatment, IFN-γ levels in the supernatant were measured by Meso Scale Discovery (MSD).

JNJ42756493 was next tested to analyze the impact on the activity of anti-PD-1 antibodies in two in vitro functional assays: Mixed Lymphocyte Reaction (MLR); and Cytomegalovirus antigen assay (CMV). For the MLR assay, CD4$^+$ T cells are stimulated with allogeneic dendritic cells, leading to T cell activation and IFN-γ secretion. In this assay, anti-PD-1 antibodies caused dose-dependent increases in IFN-γ levels (FIG. 4, PD-1 alone). When T cells and DCs were treated with 0.01, 1 or 100 nM of JNJ42756493, IFN-γ levels were similar to those observed in the untreated samples (FIG. 4, JNJ-493 alone vs controls), suggesting that FGFR inhibition does not affect T cell activation. Furthermore, combinations of JNJ42756493 with anti-PD-1 antibodies caused similar IFN-γ secretion as observed with anti-PD-1 treatment alone (FIG. 4, JNJ-493+anti-PD-1 compared to PD-1 alone). These results suggest that JNJ42756493 does not impair the functional activity of anti-PD-1 antibodies in the MLR assay.

Figure 5:
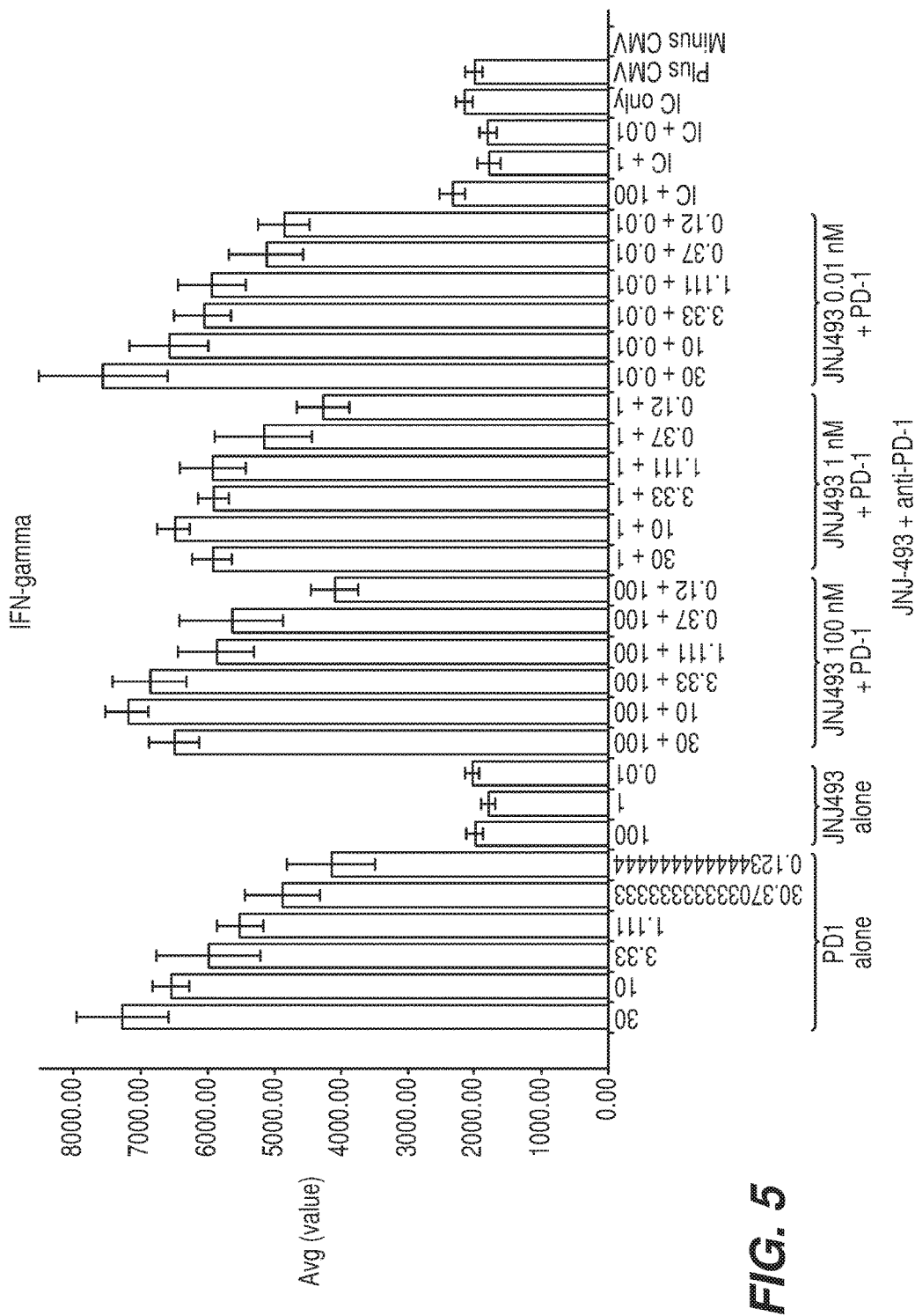
FIG. 5 illustrates the effect of JNJ42756493 on IFN-γ levels induced by anti-PD-1 antibodies in a Cytomegalovirus antigen assay (CMV) Assay. Peripheral blood mononuclear cells (PMBCs) were stimulated with CMV antigen and treated with anti-PD-1 antibodies (concentration left to right—30, 10, 3.33, 1.11, 0.37, 0.12 nM) as indicated. JNJ42756493 was added at 100, 1, or 0.01 nM alone (concentrations left to right), together with anti-PD-1 antibodies (100, 1, or 0.01 nM JNJ42756493 together with 30, 10, 3.33, 1.11, 0.37, or 0.12 nM of anti-PD-1 antibody), or in the presence of isotype control (IC). 6 days after treatment, IFN-γ levels in the supernatant were measured by MSD.

In the CMV assay, PBMCs from CMV-reactive donors were stimulated by the addition of CMV antigen. CMV-reactive T cells are active, expand and secrete pro-inflammatory cytokines such as IFN-γ. In the presence of anti-PD-1 antibodies, significantly higher levels of IFN-γ were secreted upon CMV stimulation (FIG. 5, PD-1 alone). In contrast, JNJ42756493 alone had no impact on cytokine levels (FIG. 5, JNJ-493 alone). Similarly, JNJ42756493 combinations with anti-PD-1 antibodies led to similar increases of IFN-γ as seen with anti-PD-1 alone (FIG. 5, JNJ42756493+anti-PD-1 compared to PD-1 alone). These data show that JNJ42756493 does not affect the activity of anti-PD-1 antibodies in the CMV assay.

Those skilled in the art will appreciate that numerous changes and modifications can be made to the preferred embodiments and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

Nucleotide Sequence of FGFR Fusion Genes

The nucleotide sequences for the FGFR fusion cDNA are provided in Table 6. The underlined sequences correspond to either FGFR3 or FGFR2, the sequences in black represent the fusion partners and the sequence in italic fonts represent the intron sequence of the FGFR3 gene.

TABLE 6

| | |
|---|---|
| FGFR3:TACC3 v1<br>(2850 base pairs)<br>(SEQ ID NO: 19) | >ATGGGCGCCCCTGCCTGCGCCCTCGCGCTCTGCGTGGCCGTGGCCATCGTGGCC<br>GGCGCCTCCTCGGAGTCCTTGGGGACGGAGCAGCGCGTCGTGGGGCGAGCGGCA<br>GAAGTCCCGGGCCCAGAGCCCGGCCAGCAGGAGCAGTTGGTCTTCGGCAGCGGG<br>GATGCTGTGGAGCTGAGCTGTCCCCCGCCCGGGGGTGGTCCCATGGGGCCCACTG<br>TCTGGGTCAAGGATGGCACAGGGCTGGTGCCCTCGGAGCGTGTCCTGGTGGGGC<br>CCCAGCGGCTGCAGGTGCTGAATGCCTCCCACGAGGACTCCGGGGCCTACAGCT<br>GCCGGCAGCGGCTCACGCAGCGCGTACTGTGCCACTTCAGTGTGCGGGTGACAG<br>ACGCTCCATCCTCGGGAGATGACGAAGACGGGGAGGACGAGGCTGAGGACACA<br>GGTGTGGACACAGGGGCCCCTTACTGGACACGGCCCGAGCGGATGGACAAGAAG<br>CTGCTGGCCGTGCCGGCCGCCAACACCGTCCGCTTCCGCTGCCCAGCCGCTGGCA<br>ACCCCACTCCCTCCATCTCCTGGCTGAAGAACGGCAGGGAGTTCCGCGGCGAGC<br>ACCGCATTGGAGGCATCAAGCTGCGGCATCAGCAGTGGAGCCTGGTCATGGAAA<br>GCGTGGTGCCCTCGGACCGCGGCAACTACACCTGCGTCGTGGAGAACAAGTTTG<br>GCAGCATCCGGCAGACGTACACGCTGGACGTGCTGGAGCGCTCCCCGCACCGGC<br>CCATCCTGCAGGCGGGGCTGCCGGCCAACCAGACGGCGGTGCTGGGCAGCGACG<br>TGGAGTTCCACTGCAAGGTGTACAGTGACGCACAGCCCCACATCCAGTGGCTCA<br>AGCACGTGGAGGTGAATGGCAGCAAGGTGGGCCCGGACGGCACACCCTACGTTA<br>CCGTGCTCAAGACGGCGGGCGCTAACACCACCGACAAGGAGCTAGAGGTTCTCT<br>CCTTGCACAACGTCACCTTTGAGGACGCCGGGGAGTACACCTGCCTGGCGGGCA<br>ATTCTATTGGGTTTTCTCATCACTCTGCGTGGCTGGTGGTGCTGCCAGCCGAGGA<br>GGAGCTGGTGGAGGCTGACGAGGCGGGCAGTGTGTATGCAGGCATCCTCAGCTA<br>CGGGGTGGGCTTCTTCCTGTTCATCCTGGTGGTGGCCGGCTGTGACGCTCTGCCGC<br>CTGCGCAGCCCCCCAAGAAAGGCCTGGGCTCCCCCACCGTGCACAAGATCTCCC<br>GCTTCCCGCTCAAGCGACAGGTGTCCCTGGAGTCCAACGCGTCCATGAGCTCCAA<br>CACACCACTGGTGCGCATCGCAAGGCTGTCCTCAGGGGAGGGCCCCACGCTGGC<br>CAATGTCTCCGAGCTCGAGCTGCCTGCCGACCCCAAATGGGAGCTGTCTCGGGCC<br>CGGCTGACCCTGGGCAAGCCCCTTGGGGAGGGCTGCTTCGGCCAGGTGGTCATG<br>GCGGAGGCCATCGGCATTGACAAGGACCGGGCCGCCAAGCCTGTCACCGTAGCC<br>GTGAAGATGCTGAAAGACGATGCCACTGACAAGGACCTGTCGGACCTGGTGTCT<br>GAGATGGAGATGATGAAGATGATCGGGAAACACAAAAACATCATCAACCTGCTG<br>GGCGCCTGCACGCAGGGCGGGCCCCTGTACGTGCTGGTGGAGTACGCGGCCAAG<br>GGTAACCTGCGGGAGTTTCTGCGGGCGCGGCGGCCCCCGGGCCTGGACTACTCCT<br>TCGACACCTGCAAGCCGCCCGAGGAGCAGCTCACCTTCAAGGACCTGGTGTCCTG<br>TGCCTACCAGGTGGCCCGGGGCATGGAGTACTTGGCCTCCCAGAAGTGCATCCAC<br>AGGGACCTGGCTGCCCGCAATGTGCTGGTGACCGAGGACAACGTGATGAAGATC<br>GCAGACTTCGGGCTGGCCCGGGACGTGCACAACCTCGACTACTACAAGAAGACG<br>ACCAACGGCCGGCTGCCCGTGAAGTGGATGGCGCCTGAGGCCTTGTTTGACCGA<br>GTCTACACTCACCAGAGTGACGTCTGGTCCTTTGGGGTCCTGCTCTGGGAGATCT<br>TCACGCTGGGGGGCTCCCCGTACCCCGGCATCCCTGTGGAGGAGCTCTTCAAGCT |

TABLE 6-continued

|  |  |
|---|---|
|  | GCTGAAGGAGGGCCACCGCATGGACAAGCCCGCCAACTGCACACACGACCTGTA<br>CATGATCATGCGGGAGTGCTGGCATGCCGCGCCCTCCCAGAGGCCCACCTTCAAG<br>CAGCTGGTGGAGGACCTGGACCGTGTCCTTACCGTGACGTCCACCGACGTAAAG<br>GCGACACAGGAGGAGAACCGGGAGCTGAGGAGCAGGTGTGAGGAGCTCCACGG<br>GAAGAACCTGGAACTGGGGAAGATCATGGACAGGTTCGAAGAGGTTGTGTACCA<br>GGCCATGGAGGAAGTTCAGAAGCAGAAGGAACTTTCCAAAGCTGAAATCCAGAA<br>AGTTCTAAAAGAAAAAGACCAACTTACCACAGATCTGAACTCCATGGAGAAGTC<br>CTTCTCCGACCTCTTCAAGCGTTTTGAGAAACAGAAAGAGGTGATCGAGGGCTAC<br>CGCAAGAACGAAGAGTCACTGAAGAAGTGCGTGGAGGATTACCTGGCAAGGATC<br>ACCCAGGAGGGCCAGAGGTACCAAGCCCTGAAGGCCCACGCGGAGGAGAAGCT<br>GCAGCTGGCAAACGAGGAGATCGCCCAGGTCCGGAGCAAGGCCCAGGCGGAAG<br>CGTTGGCCCTCCAGGCCAGCCTGAGGAAGGAGCAGATGCGCATCCAGTCGCTGG<br>AGAAGACAGTGGAGCAGAAGACTAAAGAGAACGAGGAGCTGACCAGGATCTGC<br>GACGACCTCATCTCCAAGATGGAGAAGATCTGA |
| FGFR3:TACC3 v3<br>(2955 base pairs)<br>(SEQ ID NO: 20) | <ATGGGCGCCCCTGCCTGCGCCCTCGCGCTCTGCGTGGCCGTGGCCATCGTGGCC<br>GGCGCCTCCTCGGAGTCCTTGGGGACGGAGCAGCGCGTCGTGGGGCGAGCGGCA<br>GAAGTCCCGGGCCCAGAGCCCGGCCAGCAGGAGCAGTTGGTCTTCGGCAGCGGG<br>GATGCTGTGGAGCTGAGCTGTCCCCCGCCCGGGGTGGTCCCATGGGGCCCACTG<br>TCTGGGTCAAGGATGGCACAGGGCTGGTGCCCTCGGAGCGTGTCCTGGTGGGGC<br>CCCAGCGGCTGCAGGTGCTGAATGCCTCCCACGAGGACTCCGGGGCCTACACGT<br>GCCGGCAGCGGCTCACGCAGCGCGTACTGTGCCACTTCAGTGTGCGGGTGACAG<br>ACGCTCCATCCTCGGGAGATGACGAAGACGGGGAGGACGAGGCTGAGGACACA<br>GGTGTGGACACAGGGGCCCCTTACTGGACACGGCCCGAGCGGATGGACAAGAAG<br>CTGCTGGCCGTGCCGGCCGCCAACACCGTCCGCTTCCGCTGCCCAGCCGCTGGCA<br>ACCCCACTCCCTCCATCTCCTGGCTGAAGAACGGCAGGGAGTTCCGCGGCGAGC<br>ACCGCATTGGAGGCATCAAGCTGCGGCATCAGCAGTGGAGCCTGGTCATGGAAA<br>GCGTGGTGCCCTCGGACCGCGGCAACTACACCTGCGTCGTGGAGAACAAGTTTG<br>GCAGCATCCGGCAGACGTACACGCTGGACGTGCTGGAGCGCTCCCCGCACCGGC<br>CCATCCTGCAGGCGGGGCTGCCGGCCAACCAGACGGCGGTGCTGGGCAGCGACG<br>TGGAGTTCCACTGCAAGGTGTACAGTGACGCACAGCCCCACATCCAGTGGCTCA<br>AGCACGTGGAGGTGAATGGCAGCAAGGTGGGCCCGGACGGCACACCCTACGTTA<br>CCGTGCTCAAGACGGCGGGCGCTAACACCACCGACAAGGAGCTAGAGGTTCTCT<br>CCTTGCACAACGTCACCTTTGAGGACGCCGGGGAGTACACCTGCCTGGCGGGCA<br>ATTCTATTGGGTTTTCTCATCACTCTGCGTGGCTGGTGGTGCTGCCAGCCGGAGGA<br>GGAGCTGGTGGAGGCTGACGAGGCGGGCAGTGTGTATGCAGGCATCCTCAGCTA<br>CGGGGTGGGCTTCTTCCTGTTCATCCTGGTGGTGGCCGGCTGTGACGCTCTGCCGC<br>CTGCGCAGCCCCCCAAGAAAGGCCTGGGCTCCCCCACCGTGCACAAGATCTCCC<br>GCTTCCCGCTCAAGCGACAGGTGTCCCTGGAGTCCAACGCGTCCATGAGCTCCAA<br>CACACCACTGGTGCGCATCGCAAGGCTGTCCTCAGGGGAGGGCCCCACGCTGGC<br>CAATGTCTCCGAGCTCGAGCTGCCTGCCGACCCCAAATGGGAGCTGTCTCGGGCC<br>CGGCTGACCCTGGGCAAGCCCCTTGGGGAGGGCTGCTTCGGCCAGGTGGTCATG<br>GCGGAGGCCATCGGCATTGACAAGGACCGGGCCGCCAAGCCTGTCACCGTAGCC<br>GTGAAGATGCTGAAAGACGATGCCACTGACAAGGACCTGTCGGACCTGGTGTCT<br>GAGATGGAGATGATGAAGATGATCGGGAAACACAAAAACATCATCAACCTGCTG<br>GGCGCCTGCACGCAGGGCGGGCCCCTGTACGTGCTGGTGGAGTACGCGGCCAAG<br>GGTAACCTGCGGGAGTTTCTGCGGGCGCGGCGGCCCCCGGGCCTGGACTACTCCT<br>TCGACACCTGCAAGCCGCCCGAGGAGCAGCTCACCTTCAAGGACCTGGTGTCCTG<br>TGCCTACCAGGTGGCCCGGGGCATGGAGTACTTGGCCTCCCAGAAGTGCATCCAC<br>AGGGACCTGGCTGCCCGCAATGTGCTGGTGACCGAGGACAACGTGATGAAGATC<br>GCAGACTTCGGGCTGGCCCGGGACGTGCACAACCTCGACTACTACAAGAAGACG<br>ACCAACGGCCGGCTGCCCGTGAAGTGGATGGCGCCTGAGGCCTTGTTTGACCGA<br>GTCTACACTCACCAGAGTGACGTCTGGTCCTTTGGGGTCCTGCTCTGGGAGATCT<br>TCACGCTGGGGGGCTCCCCGTACCCCGGCATCCCTGTGGAGGAGCTCTTCAAGCT<br>GCTGAAGGAGGGCCACCGCATGGACAAGCCCGCCAACTGCACACACGACCTGTA<br>CATGATCATGCGGGAGTGCTGGCATGCCGCGCCCTCCCAGAGGCCCACCTTCAAG<br>CAGCTGGTGGAGGACCTGGACCGTGTCCTTACCGTGACGTCCACCGACGTGCCAG<br>GCCCACCCCCAGGTGTTCCCGCGCCTGGGGGCCCACCCCTGTCCACCGGACCTAT<br>AGTGGACCTGCTCCAGTACAGCCAGAAGGACCTGGATGCAGTGGTAAAGGCGAC<br>ACAGGAGGAGAACCGGGAGCTGAGGAGCAGGTGTGAGGAGCTCCACGGGAAGA<br>ACCTGGAACTGGGGAAGATCATGGACAGGTTCGAAGAGGTTGTGTACCAGGCCA<br>TGGAGGAAGTTCAGAAGCAGAAGGAACTTTCCAAAGCTGAAATCCAGAAAGTTC<br>TAAAAGAAAAAGACCAACTTACCACAGATCTGAACTCCATGGAGAAGTCCTTCT<br>CCGACCTCTTCAAGCGTTTTGAGAAACAGAAAGAGGTGATCGAGGGCTACCGCA<br>AGAACGAAGAGTCACTGAAGAAGTGCGTGGAGGATTACCTGGCAAGGATCACCC<br>AGGAGGGCCAGAGGTACCAAGCCCTGAAGGCCCACGCGGAGGAGAAGCTGCAG<br>CTGGCAAACGAGGAGATCGCCCAGGTCCGGAGCAAGGCCCAGGCGGAAGCGTTG<br>GCCCTCCAGGCCAGCCTGAGGAAGGAGCAGATGCGCATCCAGTCGCTGGAGAAG<br>ACAGTGGAGCAGAAGACTAAAGAGAACGAGGAGCTGACCAGGATCTGCGACGA<br>CCTCATCTCCAAGATGGAGAAGATCTGA |
| FGFR3<br>Intron:TACC3<br>(4462 base pairs)<br>(SEQ ID NO: 21) | <ATGGGCGCCCCTGCCTGCGCCCTCGCGCTCTGCGTGGCCGTGGCCATCGTGGCC<br>GGCGCCTCCTCGGAGTCCTTGGGGACGGAGCAGCGCGTCGTGGGGCGAGCGGCA<br>GAAGTCCCGGGCCCAGAGCCCGGCCAGCAGGAGCAGTTGGTCTTCGGCAGCGGG<br>GATGCTGTGGAGCTGAGCTGTCCCCCGCCCGGGGTGGTCCCATGGGGCCCACTG<br>TCTGGGTCAAGGATGGCACAGGGCTGGTGCCCTCGGAGCGTGTCCTGGTGGGGC<br>CCCAGCGGCTGCAGGTGCTGAATGCCTCCCACGAGGACTCCGGGGCCTACACGT<br>GCCGGCAGCGGCTCACGCAGCGCGTACTGTGCCACTTCAGTGTGCGGGTGACAG<br>ACGCTCCATCCTCGGGAGATGACGAAGACGGGGAGGACGAGGCTGAGGACACA<br>GGTGTGGACACAGGGGCCCCTTACTGGACACGGCCCGAGCGGATGGACAAGAAG |

TABLE 6-continued

CTGCTGGCCGTGCCGGCCGCCAACACCGTCCGCTTCCGCTGCCCAGCCGCTGGCA
ACCCCACTCCCTCCATCTCCTGGCTGAAGAACGGCAGGGAGTTCCGCGGCGAGC
ACCGCATTGGAGGCATCAAGCTGCGGCATCAGCAGTGGAGCCTGGTCATGGAAA
GCGTGGTGCCCTCGGACCGCGGCAACTACACCTGCGTCGTGGAGAACAAGTTTG
GCAGCATCCGGCAGACGTACACGCTGGACGTGCTGGAGCGCTCCCCGCACCGGC
CCATCCTGCAGGCGGGGCTGCCGGCCAACCAGACGGCGGTGCTGGGCAGCGACG
TGGAGTTCCACTGCAAGGTGTACAGTGACGCACAGCCCCACATCCAGTGGCTCA
AGCACGTGGAGGTGAATGGCAGCAAGGTGGGCCCGGACGGCACACCCTACGTTA
CCGTGCTCAAGACGGCGGGCGCTAACACCACCGACAAGGAGCTAGAGGTTCTCT
CCTTGCACAACGTCACCTTTGAGGACGCCGGGGAGTACACCTGCCTGGCGGGCA
ATTCTATTGGGTTTTCTCATCACTCTGCGTGGCTGGTGGTGCTGCCAGCCGAGGA
GGAGCTGGTGGAGGCTGACGAGGCGGGCAGTGTGTATGCAGGCATCCTCAGCTA
CGGGGTGGGCTTCTTCCTGTTCATCCTGGTGGTGGCGGCTGTGACGCTCTGCCGC
CTGCGCAGCCCCCCCAAGAAAGGCCTGGGCTCCCCCACCGTGCACAAGATCTCCC
GCTTCCCGCTCAAGCGACAGGTGTCCCTGGAGTCCAACGCGTCCATGAGCTCCAA
CACACCACTGGTGCGCATCGCAAGGCTGTCCTCAGGGGAGGGCCCCACGCTGGC
CAATGTCTCCGAGCTCGAGCTGCCTGCCGACCCCAAATGGAGCTGTCTCGGGCC
CGGCTGACCCTGGGCAAGCCCCTTGGGGAGGGCTGCTTCGGCCAGGTGGTCATG
GCGGAGGCCATCGGCATTGACAAGGACCGGGCCGCCAAGCCTGTCACCGTAGCC
GTGAAGATGCTGAAAGACGATGCCACTGACAAGGACCTGTCGGACCTGGTGTCT
GAGATGGAGATGATGAAGATGATCGGGAAACACAAAAACATCATCAACCTGCTG
GGCGCCTGCACGCAGGGCGGGCCCCTGTACGTGCTGGTGGAGTACGCGGCCAAG
GGTAACCTGCGGGAGTTTCTGCGGGCGCGGCGGCCCCCGGGCCTGGACTACTCCT
TCGACACCTGCAAGCCGCCCGAGGAGCAGCTCACCTTCAAGGACCTGGTGTCCTG
TGCCTACCAGGTGGCCCGGGGCATGGAGTACTTGGCCTCCCAGAAGTGCATCCAC
AGGGACCTGGCTGCCCGCAATGTGCTGGTGACCGAGGACAACGTGATGAAGATC
GCAGACTTCGGGCTGGCCCGGGACGTGCACAACCTCGACTACTACAAGAAGACG
ACCAACGGCCGGCTGCCCGTGAAGTGGATGGCGCCTGAGGCCTTGTTTGACCGA
GTCTACACTCACCAGAGTGACGTCTGGTCCTTTGGGGTCCTGCTCTGGGAGATCT
TCACGCTGGGGGGCTCCCCGTACCCCGGCATCCCTGTGGAGGAGCTCTTCAAGCT
GCTGAAGGAGGGCCACCGCATGGACAAGCCCGCCAACTGCACACACGACCTGTA
CATGATCATGCGGGAGTGCTGGCATGCCGCGCCTCCCAGAGGCCCACCTTCAAG
CAGCTGGTGGAGGACCTGGACCGTGTCCTTACCGTGACGTCCACCGACgtgagtgctgg
ctctggcctggtgccaccgcctatgccctgcccctgccgtccccggccatcctgcccc
ccagagtgctgaggtgtggggcgggcctt TCTGGCCCAGGTGCCCTGGCTGACCTGGACT
GCTCAAGCTCTTCCCAGAGCCCAGGAAGTTCTGAGAACCAAATGGTGTCTCCAGGAAAAG
TGTCTGGCAGCCCTGAGCAAGCCGTGGAGGAAAACCTTAGTTCCTATTCCTTAGACAGAA
GAGTGACACCCGCCTCTGAGACCCTAGAAGACCCTTGCAGGACAGAGTCCCAGCACAAG
CGGAGACTCCGCACGGAGCCGAGGAAGAATGCAAAGCGGAGACTCCGCACGGAGCCGA
GGAGGAATGCCGGCACGGTGGGGTCTGTGCTCCCGCAGCAGTGGCCACTTCGCC
TCCTGGTGCAATCCCTAAGGAAGCCTGCGGAGGAGCACCCCTGCAGGGTCTGCCT
GGCGAAGCCCTGGGCTGCCCTGCGGGTGTGGGCACCCCCGTGCCAGCAGATGGC
ACTCAGACCCTTACCTGTGCACACACCTCTGCTCCTGAGAGCACAGCCCCAACCA
ACCACCTGGTGGCTGGCAGGGCCATGACCCTGAGTCCTCAGGAAGAAGTGGCTG
CAGGCCAAATGGCCAGCTCCTCGAGGAGCGGACCTGTAAAACTAGAATTTGATG
TATCTGATGGCGCCACCAGCAAAAGGGCACCCCCACCAAGGAGACTGGGAGAGA
GGTCCGGCCTCAAGCCTCCCTTGAGGAAAGCAGCAGTGAGGCAGCAAAAGGCCC
CGCAGGAGGTGGAGGAGGACGACGGTAGGAGCGGAGCAGGAGAGGACCCCCCC
ATGCCAGCTTCTCGGGGCTCTTACCACCTCGACTGGGACAAAATGGATGACCCAA
ACTTCATCCCGTTCGGAGGTGACACCAAGTCTGGTTGCAGTGGAGGCCCAGCCCC
AGAAAGCCCTGAGACCAGGCTGGGCCAGCCAGCGGCTGAACAGTTGCATGCTGG
GCCTGCCACGGAGGAGCCAGGTCCCTGTCTGAGCCAGCAGCTGCATTCAGCCTCA
GCGGAGGACACGCCTGTGGTGCAGTTGGCAGCCGAGACCCCAACAGCAGAGAGC
AAGGAGAGAGCCTTGAACTCTGCCAGCACCTCGCTTCCCACAAGCTGTCCAGAG
AGTGAGCCAGTGCCCACCCATCAGCAGGGGCAGCCTGCCTTGGAGCTGAAAGAG
GAGAGCTTCAGAGACCCCGCTGAGGTTCTAGGCACGGGCGCGGAGGTGGATTAC
CTGGAGCAGTTTGGAACTTCCTCGTTTAAGGAGTCGGCCTTGAGGAAGCAGTCCT
TATACCTCAAGTTCGACCCCCTCCTGAGGGACAGTCCTGGTAGACCAGTGCCCGT
GGCCACCGAGACCAGCAGCATGCACGGTGCAAATGAGACTCCCTCAGGACGTCC
GCGGGAAGCCAAGCTTGTGGAGTTCGATTTCTTGGGAGCACTGGACATTCCTGTG
CCAGGCCCACCCCCAGGTGTTCCCGCGCCTGGGGCCCACCCCTGTCCACCGGAC
CTATAGTGGACCTGCTCCAGTACAGCCAGAAGGACCTGGATGCAGTGGTAAAGG
CGACACAGGAGGAGAACCGGGAGCTGAGGAGCAGGTGTGAGGAGCTCCACGGG
AAGAACCTGGAACTGGGGAAGATCATGGACAGGTTCGAAGAGGTTGTGTACCAG
GCCATGGAGGAAGTTCAGAAGCAGAAGGAACTTTCCAAAGCTGAAATCCAGAAA
GTTCTAAAAGAAAAAGACCAACTTACCACAGATCTGAACTCCATGGAGAAGTCC
TTCTCCGACCTCTTCAAGCGTTTTGAGAACAGAAAGAGGTGATCAGGGCTACC
GCAAGAACGAAGAGTCACTGAAGAAGTGCGTGGAGGATTACCTGGCAAGGATCA
CCCAGGAGGGCCAGAGGTACCAAGCCCTGAAGGCCCACGCGGAGGAGAAGCTG
CAGCTGGCAAACGAGGAGATCGCCCAGGTCCGGAGCAAGGCCCAGGCGGAAGC
GTTGGCCCTCCAGGCCAGCCTGAGGAAGGAGCAGATGCGCATCCAGTCGCTGGA
GAAGACAGTGGAGCAGAAGACTAAAGAGAACGAGGAGCTGACCAGGATCTGCG
ACGACCTCATCTCCAAGATGGAGAAGATCTGA

| FGFR3:BAIAP2L1<br>(3765 base pairs)<br>(SEQ ID NO: 22) | >ATGGGCGCCCCTGCCTGCGCCCTCGCGCTCTGCGTGGCCGTGGCCATCGTGGCC<br>GGCGCCTCCTCGGAGTCCTTGGGGACGGAGCAGCGCGTCGTGGGGCGAGCGGCA<br>GAAGTCCCGGGCCCAGAGCCCGGCCAGCAGGAGCAGTTGGTCTTCGGCAGCGGG<br>GATGCTGTGGAGCTGAGCTGTCCCCCGCCCGGGGGTGGTCCCATGGGGCCCACTG<br>TCTGGGTCAAGGATGGCACAGGGCTGGTGCCCTCGGAGCGTGTCCTGGTGGGGC<br>CCCAGCGGCTGCAGGTGCTGAATGCCTCCCACGAGGACTCCGGGGCCTACAGCT |

TABLE 6-continued

|  |  |
|---|---|
|  | GCCGGCAGCGGCTCACGCAGCGCGTACTGTGCCACTTCAGTGTGCGGGTGACAG<br>ACGCTCCATCCTCGGGAGATGACGAAGACGGGGAGGACGAGGCTGAGGACACA<br>GGTGTGGACACAGGGGCCCCTTACTGGACACGGCCCGAGCGGATGGACAAGAAG<br>CTGCTGGCCGTGCCGGCCGCCAACACCGTCCGCTTCCGCTGCCCAGCCGCTGGCA<br>ACCCCACTCCCTCCATCTCCTGGCTGAAGAACGGCAGGGAGTTCCGCGGCGAGC<br>ACCGCATTGGAGGCATCAAGCTGCGGCATCAGCAGTGGAGCCTGGTCATGGAAA<br>GCGTGGTGCCCTCGGACCGCGGCAACTACACCTGCGTCGTGGAGAACAAGTTTG<br>GCAGCATCCGGCAGACGTACACGCTGGACGTGCTGGAGCGCTCCCCGCACCGGC<br>CCATCCTGCAGGCGGGGCTGCCGGCCAACCAGACGGCGGTGCTGGGCAGCGACG<br>TGGAGTTCCACTGCAAGGTGTACAGTGACGCACAGCCCCACATCCAGTGGCTCA<br>AGCACGTGGAGGTGAATGGCAGCAAGGTGGGCCCGGACGGCACACCCTACGTTA<br>CCGTGCTCAAGTCCTGGATCAGTGAGAGTGTGGAGGCCGACGTGCGCCTCCGCCT<br>GGCCAATGTGTCGGAGCGGGACGGGGGCGAGTACCTCTGTCGAGCCACCAATTT<br>CATAGGCGTGGCCGAGAAGGCCTTTTGGCTGAGCGTTCACGGGCCCGAGCAGC<br>CGAGGAGGAGCTGGTGGAGGCTGACGAGGCGGGCAGTGTGTATGCAGGCATCCT<br>CAGCTACGGGGTGGCTTCTTCCTGTTCATCCTGGTGGTGGCGGCTGTGACGCTC<br>TGCCGCTGCCGCAGCCCCCCCAAGAAAGGCCTGGGCTCCCCCACCGTGCACAAG<br>ATCTCCCGCTTCCCGCTCAAGCGACAGGTGTCCCTGGAGTCCAACGCGTCCATGA<br>GCTCCAACACACCACTGGTGCGCATCGCAAGGCTGTCCTCAGGGGAGGGCCCCA<br>CGCTGGCCAATGTCTCCGAGCTCGAGCTGCCTGCCGACCCCAAATGGGAGCTGTC<br>TCGGGCCCGGCTGACCCTGGGCAAGCCCCTTGGGGAGGGCTGCTTCGGCCAGGT<br>GGTCATGGCGGAGGCCATCGGCATTGACAAGGACCGGGCCGCCAAGCCTGTCAC<br>CGTAGCCGTGAAGATGCTGAAAGACGATGCCACTGACAAGGACCTGTCGGACCT<br>GGTGTCTGAGATGGAGATGATGAAGATGATCGGGAAACACAAAAACATCATCAA<br>CCTGCTGGGCGCCTGCACGCAGGGCGGGCCCCTGTACGTGCTGGTGGAGTACGC<br>GGCCAAGGGTAACCTGCGGGAGTTTCTGCGGGCGCGGCGGCCCCGGGCCTGGA<br>CTACTCCTTCGACACCTGCAAGCCGCCCGAGGAGCAGCTCACCTTCAAGGACCTG<br>GTGTCCTGTGCCTACCAGGTGGCCCGGGGCATGGAGTACTTGGCCTCCCAGAAGT<br>GCATCCACAGGGACCTGGCTGCCCGCAATGTGCTGGTGACCGAGGACAACGTGA<br>TGAAGATCGCAGACTTCGGGCTGGCCCGGGACGTGCACAACCTCGACTACTACA<br>AGAAGACGACCAACGGCCGGCTGCCCGTGAAGTGGATGGCGCCTGAGGCCTTGT<br>TTGACCGAGTCTACACTCACCAGAGTGACGTCTGGTCCTTTGGGGTCCTGCTCTG<br>GGAGATCTTCACGCTGGGGGGCTCCCCGTACCCCGGCATCCCTGTGGAGGAGCTC<br>TTCAAGCTGCTGAAGGAGGGCCACCGCATGGACAAGCCCGCCAACTGCACACAC<br>GACCTGTACATGATCATGCGGGAGTGCTGGCATGCCGCGCCCTCCCAGAGGCCC<br>ACCTTCAAGCAGCTGGTGGAGGACCTGGACCGTGTCCTTACCGTGACGTCCACCG<br>ACAATGTTATGAACAGTTCAATCCTGGGCTGCGAAATTTAATAAACCTGGGGA<br>AAAATTATGAGAAAGCTGTAAACGCTATGATCCTGGCAGGAAAAGCCTACTACG<br>ATGGAGTGGCCAAGATCGGTGAGATTGCCACTGGGTCCCCCGTGTCAACTGAACT<br>GGGACATGTCCTCATAGAGATTTCAAGTACCCACAAGAAACTCAACGAGAGTCT<br>TGATGAAAATTTTAAAAAATTCCACAAAGAGATTATCCATGAGCTGGAGAAGAA<br>GATAGAACTTGACGTGAAATATATGAACGCAACTCTAAAAAGATACCAAACAGA<br>ACACAAGAATAAATTAGAGTCTTTGGAGAAATCCCAAGCTGAGTTGAAGAAGAT<br>CAGAAGGAAAAGCCAAGGAAGCCGAAACGCACTCAAATATGAACACAAAGAAA<br>TTGAGTATGTGGAGACCGTTACTTCTCGTCAGAGTGAAATCCAGAAATTCATTGC<br>AGATGGTTGCAAAGAGGCTCTGCTTGAAGAGAAGAGGCGCTTCTGCTTTCTGGTT<br>GATAAGCACTGTGGCTTTGCAAACCACATACATTATTATCACTTACAGTCTGCAG<br>AACTACTGAATTCCAAGCTGCCTCGGTGGCAGGAGACCTGTGTTGATGCCATCAA<br>AGTGCCAGAGAAATCATGAATATGATCGAAGAAATAAAGACCCCAGCCTCTAC<br>CCCCGTGTCTGGAACTCCTCAGGCTTCACCCATGATCGAGAGAAGCAATGTGGTT<br>AGGAAAGATTACGACACCCTTTCTAAATGCTCACCAAAGATGCCCCCCGCTCCTT<br>CAGGCAGAGCATATACCAGTCCCTTGATCGATATGTTTAATAACCCAGCCACGGC<br>TGCCCCGAATTCACAAAGGGTAAATAATTCAACAGGTACTTCCGAAGATCCCAGT<br>TTACAGCGATCAGTTTCGGTTGCAACGGGACTGAACATGATGAAGAAGCAGAAA<br>GTGAAGACCATCTTCCCGCACACTGCGGGCTCCAACAAGACCTTACTCAGCTTTG<br>CACAGGGAGATGTCATCACGCTGCTCATCCCCGAGGAGAAGGATGGCTGGCTCT<br>ATGGAGAACACGACGTGTCCAAGGCGAGGGGTTGGTTCCCGTCGTCGTACACGA<br>AGTTGCTGGAAGAAAATGAGACAGAAGCAGTGACCGTGCCCACGCCAAGCCCCA<br>CACCAGTGAGAAGCATCAGCACCGTGAACTTGTCTGAGAATAGCAGTGTTGTCAT<br>CCCCCCACCCGACTACTTGGAATGCTTGTCCATGGGGGCAGCTGCCGACAGGAG<br>AGCAGATTCGGCCAGGACGACATCCACCTTTAAGGCCCCAGCGTCCAAGCCCGA<br>GACCGCGGCTCCTAACGATGCCAACGGGACTGCAAAGCCGCTTTTTCTCAGCGG<br>AGAAAACCCCTTTGCCACTGTGAAACTCCGCCCGACTGTGACGAATGATCGCTCG<br>GCACCCATCATTCGATGA |
| FGFR2:BICC1<br>(4989 base pairs)<br>(SEQ ID NO: 23) | >ATGGTCAGCTGGGGTCGTTTCATCTGCCTGGTCGTGGTCACCATGGCAACCTTGT<br>CCCTGGCCCGGCCCTCCTTCAGTTTAGTTGAGGATACCATTAGAGCCAGAAGA<br>GCCACCAACCAAATACCAAATCTCTCAACCAGAAGTGTACGTGGCTGCGCCAGG<br>GGAGTCGCTAGAGGTGCGCTGCCTGTTGAAAGATGCCGCCGTGATCAGTTGGACT<br>AAGGATGGGGTGCACTTGGGGCCCAACAATAGGACAGTGCTTATTGGGGAGTAC<br>TTGCAGATAAAGGGCGCCACGCCTAGAGACTCCGGCCTCTATGCTTGTACTGCCA<br>GTAGGACTGTAGACAGTGAAACTTGGTACTTCATGGTGAATGTCACAGATGCCAT<br>CTCATCCGGAGATGATGAGGATGACACCGATGGTGCGGAAGATTTTGTCAGTGA<br>GAACAGTAACAACAAGAGAGCACCATACTGGACCAACACAGAAAAGATGGAAA<br>AGCGGCTCCATGCTGTGCCTGCGGCCAACACTGTCAAGTTTCGCTGCCCAGCCGG<br>GGGGAACCCAATGCCAACCATGCGGTGGCTGAAAAACGGGAAGGAGTTTAAGCA<br>GGAGCATCGCATTGGAGGCTACAAGGTACGAAACCAGCACTGGAGCCTCATTAT<br>GGAAAGTGTGGTCCCATCTGACAAGGGAAATTATACCTGTGTAGTGGAGAATGA<br>ATACGGGTCCATCAATCACACGTACCACCTGGATGTTGTGGAGCGATCGCCTCAC<br>CGGCCCATCCTCCAAGCCGGACTGCCGGCAAATGCCTCCACAGTGGTCGGAGGA |

TABLE 6-continued

```
GACGTAGAGTTTGTCTGCAAGGTTTACAGTGATGCCCAGCCCCACATCCAGTGGA
TCAAGCACGTGGAAAAGAACGGCAGTAAATACGGGCCCGACGGGCTGCCCTACC
TCAAGGTTCTCAAGGCCGCCGGTGTTAACACCACGGACAAAGAGATTGAGGTTC
TCTATATTCGGAATGTAACTTTTGAGGACGCTGGGGAATATACGTGCTTGGCGGG
TAATTCTATTGGGATATCCTTTCACTCTGCATGGTTGACAGTTCTGCCAGCGCCTG
GAAGAGAAAAGGAGATTACAGCTTCCCCAGACTACCTGGAGATAGCCATTTACT
GCATAGGGGTCTTCTTAATCGCCTGTATGGTGGTAACAGTCATCCTGTGCCGAAT
GAAGAACACGACCAAGAAGCCAGACTTCAGCAGCCAGCCGGCTGTGCACAAGCT
GACCAAACGTATCCCCCTGCGGAGACAGGTAACAGTTTCGGCTGAGTCCAGCTCC
TCCATGAACTCCAACACCCCGCTGGTGAGGATAACAACACGCCTCTCTTCAACGG
CAGACACCCCCATGCTGGCAGGGGTCTCCGAGTATGAACTTCCAGAGGACCCAA
AATGGGAGTTTCCAAGAGATAAGCTGACACTGGGCAAGCCCCTGGGAGAAGGTT
GCTTTGGGCAAGTGGTCATGGCGGAAGCAGTGGGAATTGACAAAGACAAGCCCA
AGGAGGCGGTCACCGTGGCCGTGAAGATGTTGAAAGATGATGCCACAGAGAAAG
ACCTTTCTGATCTGGTGTCAGAGATGGAGATGATGAAGATGATTGGGAAACACA
AGAATATCATAAATCTTCTTGGAGCCTGCACACAGGATGGGCCTCTCTATGTCAT
AGTTGAGTATGCCTCTAAAGGCAACCTCCGAGAATACCTCCGAGCCCGGAGGCC
ACCCGGGATGGAGTACTCCTATGACATTAACCGTGTTCCTGAGGAGCAGATGACC
TTCAAGGACTTGGTGTCATGCACCTACCAGCTGGCCAGAGGCATGGAGTACTTGG
CTTCCCAAAAATGTATTCATCGAGATTTAGCAGCCAGAAATGTTTTGGTAACAGA
AAACAATGTGATGAAAATAGCAGACTTTGGACTCGCCAGAGATATCAACAATAT
AGACTATTACAAAAAGACCACCAATGGGCGGCTTCCAGTCAAGTGGATGGCTCC
AGAAGCCCTGTTTGATAGAGTATACACTCATCAGAGTGATGTCTGGTCCTTCGGG
GTGTTAATGTGGAGATCTTCACTTTAGGGGCTCGCCCTACCCAGGGATTCCCG
TGGAGGAACTTTTTAAGCTGCTGAAGGAAGGACACAGAATGGATAAGCCAGCCA
ACTGCACCAACGAACTGTACATGATGATGAGGGACTGTTGGCATGCAGTGCCCTC
CCAGAGACCAACGTTCAAGCAGTTGGTAGAAGACTTGGATCGAATTCTCACTCTC
ACAACCAATGAGATCATGGAGGAAACAAATACGCAGATTGCTTGGCCATCAAAA
CTGAAGATCGGAGCCAAATCCAAGAAAGATCCCCATATTAAGGTTTCTGGAAAG
AAAGAAGATGTTAAAGAAGCCAAGGAAATGATCATGTCTGTCTTAGACACAAAA
AGCAATCGAGTCACACTGAAGATGGATGTTTCACATACAGAACATTCACATGTA
ATCGGCAAAGGTGGCAACAATATTAAAAAAGTGATGGAAGAAACCGGATGCCAT
ATCCACTTTCCAGATTCCAACAGGAATAACCAAGCAGAAAAAAGCAACCAGGTA
TCTATAGCGGGACAACCAGCAGGAGTAGAATCTGCCCGAGTTAGAATTCGGGAG
CTGCTTCCTTTGGTGCTGATGTTTGAGCTACCAATTGCTGGAATTCTTCAACCGGT
TCCTGATCCTAATTCCCCCTCTATTCAGCATATATCACAAACGTACAATATTTCAG
TATCATTTAAACAGCGTTCCCGAATGTATGGTGCTACTGTCATAGTACGAGGGTC
TCAGAATAACACTAGTGCTGTGAAGGAAGGAACTGCCATGCTGTTAGAACATCTT
GCTGGGAGCTTAGCATCAGCTATTCCTGTGAGCACACAACTAGATATTGCAGCTC
AACATCATCTCTTTATGATGGGTCGAAATGGGAGCAACATCAAACATATCATGCA
GAGAACAGGTGCTCAGATCCACTTTCCTGATCCCAGTAATCCACAAAAGAAATCT
ACCGTCTACCTCCAGGGCACCATTGAGTCTGTCTGTCTTGCAAGGCAATATCTCA
TGGGTTGTCTTCCTCTTGTGTTGATGTTTGATATGAAGGAAGAAATTGAAGTAGA
TCCACAATTCATTGCGCAGTTGATGGAACAGCTTGATGTCTTCATCAGTATTAAA
CCAAAGCCCAAACAGCCAAGCAAGTCTGTGATTGTGAAAAGTGTTGAGCGAAAT
GCCTTAAATATGTATGAAGCAAGGAAATGTCTCCTCGGACTTGAAAGCAGTGGG
GTTACCATAGCAACCAGTCCATCCCCAGCATCCTGCCCTGCCGGCCTGGCATGTC
CCAGCCTGGATATCTTAGCTTCAGCAGGCCTTGGACTCACTGGACTAGGTCTTTT
GGGACCCACCACCTTATCTCTGAACACTTCAACAACCCCAAACTCACTCTTGAAT
GCTCTTAATAGCTCAGTCAGTCCTTTGCAAAGTCCAAGTTCTGGTACACCCAGCC
CCACATTATGGGCACCCCCACTTGCTAATACTTCAAGTGCCACAGGTTTTTCTGCT
ATACCACACCTTATGATTCCATCTACTGCCCAAGCCACATTAACTAATATTTTGTT
GTCTGGAGTGCCCACCTATGGGCACACAGCTCCATCTCCCCCTCCTGGCTTGACT
CCTGTTGATGTCCATATCAACAGTATGCAGACCGAAGGCAAAAAAATCTCTGCTG
CTTTAAATGGACATGCACAGTCTCCAGATATAAAATATGGTGCAATATCCACTTC
ATCACTTGGAGAAAAAGTGCTGAGTGCAAATCACGGGGATCCGTCCATCCAGAC
AAGTGGGTCTGAGCAGACATCTCCCAAATCAAGCCCCACTGAAGGTTGTAATGA
TGCTTTTGTTGAAGTAGGCATGCCTCGAAGTCCTTCCCATTCTGGGAATGCTGGT
GACTTGAAACAGATGATGTGTCCCTCCAAGGTTTCCTGTGCCAAAAGGCAGACA
GTGGAACTATTGCAAGGCACGAAAAACTCACACTTACACAGCACTGACAGGTTG
CTCTCAGACCCTGAACTGAGTGCTACCGAAAGCCCTTTGGCTGACAAGAAGGCTC
CAGGGAGTGAGCGCGCTGCAGAGAGGGCAGCAGCTGCCCAGCAAAACTCCGAA
AGGGCCCACCTTGCTCCACGGTCATCATATGTCAACATGCAGGCATTTGACTATG
AACAGAAGAAGCTATTAGCCACCAAAGCTATGTTAAAGAAACCAGTGGTGACGG
AGGTCAGAACGCCCACAAATACCTGGAGTGGCCTGGGTTTTTCTAAATCCATGCC
AGCTGAAACTATCAAGGAGTTGAGAAGGGCCAATCATGTGTCCTATAAGCCCAC
AATGACAACCACTTATGAGGGCTCATCCATGTCCCTTTCACGGTCCAACAGTCGT
GAGCACTTGGGAGGTGGAAGCGAATCTGATAACTGGAGAGACCGAAATGGAATT
GGACCTGGAAGTCATAGTGAATTTGCAGCTTCTATTGGCAGCCCTAAGCGTAAAC
AAAACAAATCAACGGAACACTATCTCAGCAGTAGCAATTACATGGACTGCATTT
CCTCGCTGACAGGAAGCAATGGCTGTAACTTAAATAGCTCTTTCAAAGGTTCTGA
CCTCCCTGAGCTCTTCAGCAAACTGGGCCTGGGCAAATACACAGATGTTTTCCAG
CAACAAGAGATCGATCTTCAGACATTCCTCACTCTCACAGATCAGGATCTGAAGG
AGCTGGGAATAACTACTTTTGGTGCCAGGAGGAAATGCTGCTTGCAATTTCAGA
ACTAAATAAAAACCGAAGAAGCTTTTTGAATCGCCAAATGCACGCACCTCTTTC
CTGGAAGGTGGAGCGAGTGGAAGGCTACCCCGTCAGTATCACTCAGACATTGCT
AGTGTCAGTGGCCGCTGGTAG
```

TABLE 6-continued

| FGFR2:AFF3 (5109 base pairs) (SEQ ID NO: 24) | >ATGGTCAGCTGGGGTCGTTTCATCTGCCTGGTCGTGGTCACCATGGCAACCTTGT<br>CCCTGGCCCGGCCCTCCTTCAGTTTAGTTGAGGATACCACATTAGAGCCAGAAGA<br>GCCACCAACCAAATACCAAATCTCTCAACCAGAAGTGTACGTGGCTGCGCCAGG<br>GGAGTCGCTAGAGGTGCGCTGCCTGTTGAAAGATGCCGCCGTGATCAGTTGGACT<br>AAGGATGGGGTGCACTTGGGGCCCAACAATAGGACAGTGCTTATTGGGGAGTAC<br>TTGCAGATAAAGGGCGCCACGCCTAGAGACTCCGGCCTCTATGCTTGTACTGCCA<br>GTAGGACTGTAGACAGTGAAACTTGGTACTTCATGGTGAATGTCACAGATGCCAT<br>CTCATCCGGAGATGATGAGGATGACACCGATGGTGCGGAAGATTTTGTCAGTGA<br>GAACAGTAACAACAAGAGAGCACCATACTGGACCAACACAGAAAAGATGGAAA<br>AGCGGCTCCATGCTGTGCCTGCGGCCAACACTGTCAAGTTTCGCTGCCCAGCCGG<br>GGGGAACCCAATGCCAACCATGCGGTGGCTGAAAAACGGGAAGGAGTTTAAGCA<br>GGAGCATCGCATTGGAGGCTACAAGGTACGAAACCAGCACTGGAGCCTCATTAT<br>GGAAAGTGTGGTCCCATCTGACAAGGGAAATTATACCTGTGTAGTGGAGAATGA<br>ATACGGGTCCATCAATCACACGTACCACCTGGATGTTGTGGAGCGATCGCCTCAC<br>CGGCCCATCCTCCAAGCCGGACTGCCGGCAAATGCCTCCACAGTGGTCGGAGGA<br>GACGTAGAGTTTGTCTGCAAGGTTTACAGTGATGCCCAGCCCCACATCCAGTGGA<br>TCAAGCACGTGGAAAAGAACGGCAGTAAATACGGGCCCGACGGGCTGCCCTACC<br>TCAAGGTTCTCAAGGCCGCCGGTGTTAACACCACGGACAAAGAGATTGAGGTTC<br>TCTATATTCGGAATGTAACTTTTGAGGACGCTGGGGAATATACGTGCTTGGCGGG<br>TAATTCTATTGGGATATCCTTTCACTCTGCATGGTTGACAGTTCTGCCAGCGCCTG<br>GAAGAGAAAAGGAGATTACAGCTTCCCCAGACTACCTGGAGATAGCCATTTACT<br>GCATAGGGGTCTTCTTAATCGCCTGTATGGTGGTAACAGTCATCCTGTGCCGAAT<br>GAAGAACACGACCAAGAAGCCAGACTTCAGCAGCCAGCCGGCTGTGCACAAGCT<br>GACCAAACGTATCCCCCTGCGGAGACAGGTAACAGTTTCGGCTGAGTCCAGCTCC<br>TCCATGAACTCCAACACCCCGCTGGTGAGGATAACAACACGCCTCTCTTCAACGG<br>CAGACACCCCCATGCTGGCAGGGGTCTCCGAGTATGAACTTCCAGAGGACCCAA<br>AATGGGAGTTTCCAAGAGATAAGCTGACACTGGGCAAGCCCCTGGGAGAAGGTT<br>GCTTTGGGCAAGTGGTCATGGCGGAAGCAGTGGGAATTGACAAAGACAAGCCCA<br>AGGAGGCGGTCACCGTGGCCGTGAAGATGTTGAAAGATGATGCCACAGAGAAAG<br>ACCTTTCTGATCTGGTGTCAGAGATGGAGATGATGAAGATGATTGGGAAACACA<br>GAATATCATAAATCTTCTTGGAGCCTGCACACAGGATGGGCCTCTCTATGTCAT<br>AGTTGAGTATGCCTCTAAAGGCAACCTCCGAGAATACCTCCGAGCCCGGAGGCC<br>ACCCGGGATGGAGTACTCCTATGACATTAACCGTGTTCCTGAGGAGCAGATGACC<br>TTCAAGGACTTGGTGTCATGCACCTACCAGCTGGCCAGAGGCATGGAGTACTTGG<br>CTTCCCAAAAATGTATTCATCGAGATTTAGCAGCCAGAAATGTTTTGGTAACAGA<br>AAACAATGTGATGAAAATAGCAGACTTTGGACTCGCCAGAGATATCAACAATAT<br>AGACTATTACAAAAAGACCACCAATGGGCGGCTTCCAGTCAAGTGGATGGCTCC<br>AGAAGCCCTGTTTGATAGAGTATACACTCATCAGAGTGATGTCTGGTCCTTCGGG<br>GTGTTAATGTGGGAGATCTTCACTTTAGGGGGCTCGCCCTACCCAGGGATTCCCG<br>TGGAGGAACTTTTTAAGCTGCTGAAGGAAGGACACAGAATGGATAAGCCAGCCA<br>ACTGCACCAACGAACTGTACATGATGATGAGGGACTGTTGGCATGCAGTGCCCTC<br>CCAGAGACCAACGTTCAAGCAGTTGGTAGAAGACTTGGATCGAATTCTCACTCTC<br>ACAACCAATGAGGAGAGTAGATCTGGAGAAACCAACAGCTGTGTTGAAGAAATA<br>ATCCGGGAGATGACCTGGCTTCCACCACTTTCTGCTATTCAAGCACCTGGCAAAG<br>TGGAACCAACCAAATTTCCATTTCCAAATAAGGACTCTCAGCTTGTATCCTCTGG<br>ACACAATAATCCAAAGAAAGGTGATGCAGAGCCAGAGAGTCCAGACAGTGGCA<br>CATCGAATACATCAATGCTGGAAGATGACCTTAAGCTAAGCAGTGATGAAGAGG<br>AGAATGAACAGCAGGCAGCTCAGAGAACGGCTCTCCGCGCTCTCTCTGACAGCG<br>CCGTGGTCCAGCAGCCCAACTGCAGAACCTCGGTGCCTTCCAGCAAGGGCAGCA<br>GCAGCAGCAGCAGCAGCGGCAGCAGCAGCTCCTCCAGCGACTCAGAGAGCAGCT<br>CCGGATCTGACTCGGAGACCGAGAGCAGCTCCAGCGAGAGTGAGGGCAGCAAGC<br>CCCCCCACTTCTCCAGCCCCGAGGCTGAACCGGCATCCTCTAACAAGTGGCAGCT<br>GGATAAATGGCTAAACAAAGTTAATCCCCACAAGCCTCCTATTCTGATCCAAAAT<br>GAAAGCCACGGGTCAGAGAGCAATCAGTACTACAACCCGGTGAAAGAGGACGTC<br>CAGGACTGTGGGAAAGTCCCCGACGTTTGCCAGCCCAGCCTGAGAGAGAAGGAG<br>ATCAAGAGCACTTGCAAGGAGGAGCAAAGGCCAAGGACAGCCAACAAGGCCCC<br>TGGGAGTAAAGGCGTGAAGCAGAAGTCCCCGCCCGCGGCCGTGGCCGTGGCGGT<br>GAGCGCAGCCGCCCCGCCACCCGCAGTGCCCTGTGCGCCCGCGGAGAACGCGCC<br>CGCGCCTGCCCGGAGGTCCGCGGGCAAGAAGCCCACCAGGCGCACCGAGAGGAC<br>CTCAGCCGGGACGGCGCCAACTGCCACCGGCCCGAGGAGCCCGCGGCCGCGGA<br>CGCGCTGGGGACGAGCGTGGTGGTCCCCCCGGAGCCCACCAAAACCAGGCCCTG<br>TGGCAACAACAGAGCGAGCCACCGCAAGGAGCTGCGCTCCTCCGTGACCTGCGA<br>GAAGCGCCGCACGCGGGGCTAAGCAGGATCGTCCCCAAATCCAAGGAGTTCAT<br>TGAGACAGAGTCGTCATCTTCATCCTCCTCCTCGGACTCCGACCTGGAGTCCGAG<br>CAGGAGGAGTACCCTCTGTCCAAAGCACAGACCGTGGCTGCCTCTGCCTCCTCCG<br>GGAATGATCAGAGGCTGAAGGAGGCCGCTGCCAACGGGGGCAGTGGTCCTAGGG<br>CCCCTGTAGGCTCCATCAACGCCAGGACCACCAGTGACATCGCCAAGGAGCTGG<br>AGGAGCAGTTCTACACACTGGTCCCCTTTGGCCGGAACGAACTTCTCTCCCCTCT<br>AAAGGACAGTGATGAGATCAGGTCTCTCTGGGTCAAAATCGACCTGACCCTCCTG<br>TCCAGGATCCCAGAACACCTGCCCCAGGAGCCAGGGGTATTGAGCGCCCCTGCC<br>ACCAAGGACTCTGAGAGCGCACCGCCCAGCCACACCTCGGACACACCTGCAGAA<br>AAGGCTTTGCCAAAATCCAAGAGGAAACGCAAGTGTGACAACGAAGACGACTAC<br>AGGGAGATCAAGAAGTCCCAGGGAGAGAAAGACAGCTCTTCAAGACTGGCCACC<br>TCCACCAGTAATACTTTGTCTGCAAACACTGCAACATGAACATCAACAGTGTGG<br>CAATACCAATAAATAAAAATGAAAAAATGCTTCGGTCGCCCATCTCACCCCTCTC<br>TGATGCATCTAAACACAAATACACCAGCGAGGACTTAACTTCTTCCAGCCGACCT<br>AATGGCAACAGTTTGTTTACTTCAGCCTCTTCCAGCAAAAAGCCTAAGGCCGACA<br>GCCAGCTGCAGCCTCACGGCGGAGACCTCACGAAAGCAGCTCACAACAATTCTG<br>AAAACATTCCCCTCCACAAGTCACGGCCGCAGACGAAGCCGTGGTCTCCAGGCT<br>CCAACGGCCACAGGGACTGCAAGAGGCAGAAACTTGTCTTCGATGATATGCCTC |

TABLE 6-continued

| | |
|---|---|
| | GCAGTGCCGATTATTTTATGCAAGAAGCTAAACGAATGAAGCATAAAGCAGATG<br>CAATGGTGGAAAAGTTTGGAAAGGCTTTGAACTATGCTGAAGCAGCATTGTCGTT<br>TATCGAGTGTGGAAATGCAATGGAACAAGGCCCCATGGAATCCAAATCTCCTTAT<br>ACGATGTATTCAGAAACAGTAGAGCTCATCAGGTATGCTATGAGACTAAAAACC<br>CACTCAGGCCCCAATGCCACACCAGAAGACAAACAACTGGCTGCATTATGTTAC<br>CGATGCCTGGCCCTCCTGTACTGGCGGATGTTTCGACTCAAAAGGGACCACGCTG<br>TAAAGTATTCAAAAGCACTAATCGACTATTTCAAGAACTCATCTAAAGCCGCCCA<br>AGCCCCATCTCCGTGGGGGGCCAGTGGAAAGAGCACTGGAACCCCATCCCCCAT<br>GTCTCCCAACCCCTCTCCCGCCAGCTCCGTGGGGTCTCAGGGCAGCCTCTCCAAC<br>GCCAGCGCCCTGTCCCCGTCGACCATCGTCAGCATCCCACAGCGCATCCACCAGA<br>TGGCGGCCAACCACGTCAGCATCACCAACAGCATCCTGCACAGCTACGACTACT<br>GGGAGATGGCCGACAACTGGCCAAGGAAAACCGAGAATTCTTCAACGACCTGG<br>ATCTGCTCATGGGGCCGGTCACCCTGCACAGCAGCATGGAGCACCTGGTCCAGTA<br>CTCCCAACAGGGCCTGCACTGGCTGCGGAACAGCGCCCACCTGTCATAG |
| FGFR2:CASP7<br>(3213 base pairs)<br>(SEQ ID NO: 25) | <u>>ATGGTCAGCTGGGGTCGTTTCATCTGCCTGGTCGTGGTCACCATGGCAACCTTGT<br>CCCTGGCCCGGCCCTCCTTCAGTTTAGTTGAGGATACCACATTAGAGCCAGAAGA<br>GCCACCAACCAAATACCAAATCTCTCAACCAGAAGTGTACGTGGCTGCGCCAGG<br>GGAGTCGCTAGAGGTGCGCTGCCTGTTGAAAGATGCCGCCGTGATCAGTTGGACT<br>AAGGATGGGGTGCACTTGGGGCCCAACAATAGGACAGTGCTTATTGGGGAGTAC<br>TTGCAGATAAAGGGCGCCACGCCTAGAGACTCCGGCCTCTATGCTTGTACTGCCA<br>GTAGGACTGTAGACAGTGAAACTTGGTACTTCATGGTGAATGTCACAGATGCCAT<br>CTCATCCGGAGATGATGAGGATGACACCGATGGTGCGGAAGATTTTGTCAGTGA<br>GAACAGTAACAACAAGAGAGCACCATACTGGACCAACACAGAAAAGATGGAAA<br>AGCGGCTCCATGCTGTGCCTGCGGCCAACACTGTCAAGTTTCGCTGCCCAGCCGG<br>GGGGAACCCAATGCCAACCATGCGGTGGCTGAAAAACGGGAAGGAGTTTAAGCA<br>GGAGCATCGCATTGGAGGCTACAAGGTACGAAACCAGCACTGGAGCCTCATTAT<br>GGAAAGTGTGGTCCCATCTGACAAGGGAAATTATACCTGTGTAGTGGAGAATGA<br>ATACGGGTCATCAATCACACGTACCACCTGGATGTTGTGGAGCGATCGCCTCAC<br>CGGCCCATCCTCCAAGCCGGACTGCCGGCAAATGCCTCCACAGTGGTCGGAGGA<br>GACGTAGAGTTTGTCTGCAAGGTTTACAGTGATGCCCAGCCCCACATCCAGTGGA<br>TCAAGCACGTGGAAAAGAACGGCAGTAAATACGGGCCCGACGGGCTGCCCTACC<br>TCAAGGTTCTCAAGGCCGCCGGTGTTAACACCACGGACAAAGAGATTGAGGTTC<br>TCTATATTCGGAATGTAACTTTTGAGGACGCTGGGGAATATACGTGCTTGGCGGG<br>TAATTCTATTGGGATATCCTTTCACTCTGCATGGTTGACAGTTCTGCCAGCGCCTG<br>GAAGAGAAAGGAGATTACAGCTTCCCCAGACTACCTGGAGATAGCCATTTACT<br>GCATAGGGGTCTTCTTAATCGCCTGTATGGTGGTAACAGTCATCCTGTGCCGAAT<br>GAAGAACACGACCAAGAAGCCAGACTTCAGCAGCCAGCCGGCTGTGCACAAGCT<br>GACCAAACGTATCCCCCTGCGGAGACAGGTAACAGTTTCGGCTGAGTCCAGCTCC<br>TCCATGAACTCCAACACCCCGCTGGTGAGGATAACAACACGCCTCTCTTAACGG<br>CAGACACCCCCATGCTGGCAGGGGTCTCCGAGTATGAACTTCCAGAGGACCCAA<br>AATGGGAGTTTCCAAGAGATAAGCTGACACTGGGCAAGCCCCTGGGAGAAGGTT<br>GCTTTGGGCAAGTGGTCATGGCGGAAGCAGTGGGAATTGACAAAGACAAGCCCA<br>AGGAGGCGGTCACCGTGGCCGTGAAGATGTTGAAAGATGATGCCACAGAGAAAG<br>ACCTTTCTGATCTGGTGTCAGAGATGGAGATGATGAAGATGATTGGGAAACACA<br>AGAATATCATAAATCTTCTTGGAGCCTGCACACAGGATGGGCCTCTCTATGTCAT<br>AGTTGAGTATGCCTCTAAAGGCAACCTCCGAGAATACCTCCGAGCCCGGAGGCC<br>ACCCGGGATGGAGTACTCCTATGACATTAACCGTGTTCCTGAGGAGCAGATGACC<br>TTCAAGGACTTGGTGTCATGCACCTACCAGCTGGCCAGAGGCATGGAGTACTTGG<br>CTTCCCAAAAATGTATTCATCGAGATTTAGCAGCCAGAAATGTTTTGGTAACAGA<br>AAACAATGTGATGAAAATAGCAGACTTTGGACTCGCCAGAGATATCAACAATAT<br>AGACTATTACAAAAAGACCACCAATGGGCGGCTTCCAGTCAAGTGGATGGCTCC<br>AGAAGCCCTGTTTGATAGAGTATACACTCATCAGAGTGATGTCTGGTCCTTCGGG<br>GTGTTAATGTGGGAGATCTTCACTTTAGGGGGCTCGCCCTACCCAGGGATTCCCG<br>TGGAGGAACTTTTTAAGCTGCTGAAGGAAGGACACAGAATGGATAAGCCAGCCA<br>ACTGCACCAACGAACTGTACATGATGATGAGGGACTGTTGGCATGCAGTGCCCTC<br>CCAGAGACCAACGTTCAAGCAGTTGGTAGAAGACTTGGATCGAATTCTCACTCTC<br>ACAACCAATGAGATGGCAGATGATCAGGGCTGTATTGAAGAGCAGGGGGTTGAG<br>GATTCAGCAAATGAAGATTCAGTGGATGCTAAGCCAGACCGGTCCTCGTTTGTAC<br>CGTCCCTCTTCAGTAAGAAGAAGAAAAATGTCACCATGCGATCCATCAAGACCA<br>CCCGGGACCGAGTGCCTACATATCAGTACAACATGAATTTTGAAAAGCTGGGCA<br>AATGCATCATAATAAACAACAAGAACTTTGATAAAGTGACAGGTATGGGCGTTC<br>GAAACGGAACAGACAAAGATGCCGAGGCGCTCTTCAAGTGCTTCCGAAGCCTGG<br>GTTTTGACGTGATTGTCTATAATGACTGCTCTTGTGCCAAGATGCAAGATCTGCTT<br>AAAAAAGCTTCTGAAGAGGACCATACAAATGCCGCCTGCTTCGCCTGCATCCTCT<br>TAAGCCATGGAGAAGAAAATGTAATTTATGGGAAAGATGGTGTCACACCAATAA<br>AGGATTTGACAGCCCACTTTAGGGGGGAACTAGATGCAAAACCCTTTTAGAGAAAC<br>CCAAACTCTTCTTCATTCAGGCTTGCCGAGGGACCGAGCTTGATGATGGCATCCA<br>GGCCGACTCGGGGCCCATCAATGACACAGATGCTAATCCTCGATACAAGATCCC<br>AGTGGAAGCTGACTTCCTCTTCGCCTATTCCACGGTTCCAGGCTATTACTCGTGG<br>AGGAGCCCAGGAAGAGGCTCCTGGTTTGTGCAAGCCCTCTGCTCCATCCTGGAGG<br>AGCACGGAAAAGACCTGGAAATCATGCAGATCCTCACCAGGGTGAATGACAGAG<br>TTGCCAGGCACTTTGAGTCTCAGTCTGATGACCCACACTTCCATGAGAAGAAGCA<br>GATCCCCTGTGTGGTCTCCATGCTCACCAAGGAACTCTACTTCAGTCAATAG</u> |
| FGFR2:CCDC6<br>(3423 base pairs)<br>(SEQ ID NO: 26) | <u>>ATGGTCAGCTGGGGTCGTTTCATCTGCCTGGTCGTGGTCACCATGGCAACCTTGT<br>CCCTGGCCCGGCCCTCCTTCAGTTTAGTTGAGGATACCACATTAGAGCCAGAAGA<br>GCCACCAACCAAATACCAAATCTCTCAACCAGAAGTGTACGTGGCTGCGCCAGG<br>GGAGTCGCTAGAGGTGCGCTGCCTGTTGAAAGATGCCGCCGTGATCAGTTGGACT<br>AAGGATGGGGTGCACTTGGGGCCCAACAATAGGACAGTGCTTATTGGGGAGTAC</u> |

TABLE 6-continued

| | |
|---|---|
| | TTGCAGATAAAGGGCGCCACGCCTAGAGACTCCGGCCTCTATGCTTGTACTGCCA |
| | GTAGGACTGTAGACAGTGAAACTTGGTACTTCATGGTGAATGTCACAGATGCCAT |
| | CTCATCCGGAGATGATGAGGATGACACCGATGGTGCGGAAGATTTTGTCAGTGA |
| | GAACAGTAACAACAAGAGAGCACCATACTGGACCAACACAGAAAAGATGGAAA |
| | AGCGGCTCCATGCTGTGCCTGCGGCCAACACTGTCAAGTTTCGCTGCCCAGCCGG |
| | GGGGAACCCAATGCCAACCATGCGGTGGCTGAAAAACGGGAAGGAGTTTAAGCA |
| | GGAGCATCGCATTGGAGGCTACAAGGTACGAAACCAGCACTGGAGCCTCATTAT |
| | GGAAAGTGTGGTCCCATCTGACAAGGGAAATTATACCTGTGTAGTGGAGAATGA |
| | ATACGGGTCCATCAATCACACGTACCACCTGGATGTTGTGGAGCGATCGCCTCAC |
| | CGGCCCATCCTCCAAGCCGGACTGCCGGCAAATGCCTCCACAGTGGTCGGAGGA |
| | GACGTAGAGTTTGTCTGCAAGGTTTACAGTGATGCCCAGCCCCACATCCAGTGGA |
| | TCAAGCACGTGGAAAAGAACGGCAGTAAATACGGGCCGACGGGCTGCCCTACC |
| | TCAAGGTTCTCAAGGCCGCCGGTGTTAACACCACGGACAAAGAGATTGAGGTTC |
| | TCTATATTCGGAATGTAACTTTTGAGGACGCTGGGGAATATACGTGCTTGGCGGG |
| | TAATTCTATTGGGATATCCTTTCACTCTGCATGGTTGACAGTTCTGCCAGCGCCTG |
| | GAAGAGAAAAGGAGATTACAGCTTCCCCAGACTACCTGGAGATAGCCATTTACT |
| | GCATAGGGGTCTTCTTAATCGCCTGTATGGTGGTAACAGTCATCCTGTGCCGAAT |
| | GAAGAACACGACCAAGAAGCCAGACTTCAGCAGCCAGCCGGCTGTGCACAAGCT |
| | GACCAAACGTATCCCCCTGCGGAGACAGGTAACAGTTTCGGCTGAGTCCAGCTCC |
| | TCCATGAACTCCAACACCCCGCTGGTGAGGATAACAACACGCCTCTCTTCAACGG |
| | CAGACACCCCCATGCTGGCAGGGGTCTCCGAGTATGAACTTCCAGAGGACCCAA |
| | AATGGGAGTTTCCAAGAGATAAGCTGACACTGGGCAAGCCCCTGGGAGAAGGTT |
| | GCTTTGGGCAAGTGGTCATGGCGGAAGCAGTGGGAATTGACAAAGACAAGCCCA |
| | AGGAGGCGGTCACCGTGGCCGTGAAGATGTTGAAAGATGATGCCACAGAGAAAG |
| | ACCTTTCTGATCTGGTGTCAGAGATGGAGATGATGAAGATGATTGGGAAACACA |
| | AGAATATCATAAATCTTCTTGGAGCCTGCACACAGGATGGGCCTCTCTATGTCAT |
| | AGTTGAGTATGCCTCTAAAGGCAACCTCCGAGAATACCTCCGAGCCCGGAGGCC |
| | ACCCGGGATGGAGTACTCCTATGACATTAACCGTGTTCCTGAGGAGCAGATGACC |
| | TTCAAGGACTTGGTGTCATGCACCTACCAGCTGGCCAGAGGCATGGAGTACTTGG |
| | CTTCCCAAAAATGTATTCATCGAGATTTAGCAGCCAGAAATGTTTTGGTAACAGA |
| | AAACAATGTGATGAAAATAGCAGACTTTGGACTCGCCAGAGATATCAACAATAT |
| | AGACTATTACAAAAAGACCACCAATGGGCGGCTTCCAGTCAAGTGGATGGCTCC |
| | AGAAGCCCTGTTTGATAGAGTATACACTCATCAGAGTTGATGTCTGGTCCTTCGGG |
| | GTGTTAATGTGGGAGATCTTCACTTTAGGGGGCTCGCCCTACCCAGGGATTCCCG |
| | TGGAGGAACTTTTTAAGCTGCTGAAGGAAGGACACAGAATGGATAAGCCAGCCA |
| | ACTGCACCAACGAACTGTACATGATGATGAGGGACTGTTGGCATGCAGTGCCCTC |
| | CCAGAGACCAACGTTCAAGCAGTTGGTAGAAGACTTGGATCGAATTCTCACTCTC |
| | ACAACCAATGAGCAAGCCAGGGCTGAGCAGGAAGAAGAATTCATTAGTAACACT |
| | TTATTCAAGAAAATTCAGGCTTTTGCAGAAGGAGAAAGAAACCCTTGCTGTAAATT |
| | ATGAGAAAGAAGAAGAATTCCTCACTAATGAGCTCTCCAGAAAATTGATGCAGT |
| | TGCAGCATGAGAAAGCCGAACTAGAACAGCATCTTGAACAAGAGCAGGAATTTC |
| | AGGTCAACAAACTGATGAAGAAAATTAAAAAACTGGAGAATGACACCATTTCTA |
| | AGCAACTTACATTAGAACAGTTGAGACGGGAGAAGATTGACCTTGAAAATACAT |
| | TGGAACAAGAACAAGAGCACTAGTTAATCGCCTCTGGAAAAGGATGGATAAGC |
| | TTGAAGCTGAAAAGCGAATCCTGCAGGAAAAATTAGACCAGCCCGTCTCTGCTC |
| | CACCATCGCCTAGAGATATCTCCATGGAGATTGATTCTCAGAAAATATGATGCG |
| | TCACATCAGGTTTTTAAAGAATGAAGTGGAACGGCTGAAGAAGCAACTGAGAGC |
| | TGCTCAGTTACAGCATTCAGAGAAAATGGCACAGTATCTGGAGGAGGAACGTCA |
| | CATGAGAGAAGAGAACTTGAGGCTCCAGAGGAAGCTGCAGAGGGAGATGGAGA |
| | GAAGAGAAGCCCTCTGTCGACAGCTCTCCGAGAGTGAGTCCAGCTTAGAAATGG |
| | ACGACGAAAGGTATTTAATGAGATGTCTGCACAAGGATTAAGACCTCGCACTGT |
| | GTCCAGCCCGATCCCTTACACACCTTCTCCGAGTTCAAGCAGGCCTATATCACCT |
| | GGTCTATCATATGCAAGTCACACGGTTGGTTTCACGCCACCAACTTCACTGACTA |
| | GAGCTGGAATGTCTTATTACAATTCCCCGGGTCTTCACGTGCAGCACATGGGAAC |
| | ATCCCATGGTATCACAAGGCCTTCACCACGGAGAAGCAACAGTCCTGACAAATT |
| | CAAACGGCCCACGCCGCCTCCATCTCCCAACACACAGACCCCAGTCCAGCCACCT |
| | CCGCCTCCACCTCCGCCACCCATGCAGCCCACGGTCCCCTCAGCAGCCACCTCGC |
| | AGCCTACTCCTTCGCAACATTCGGCGCACCCCTCCTCCCAGCCTTAA |
| FGFR2:OFD1<br>(5229 base pairs)<br>(SEQ ID NO: 27) | >ATGGTCAGCTGGGGTCGTTTCATCTGCCTGGTCGTGGTCACCATGGCAACCTTGT<br>CCCTGGCCCGGCCCTCCTTCAGTTTAGTTGAGGATACCACATTAGAGCCAGAAGA<br>GCCACCAACCAAATACCAAATCTCTCAACCAGAAGTGTACGTGGCTGCGCCAGG<br>GGAGTCGCTAGAGGTGCGCTGCCTGTTGAAAGATGCCGCCGTGATCAGTTGGACT<br>AAGGATGGGGTGCACTTGGGGCCCAACAATAGGACAGTGCTTATTGGGGAGTAC<br>TTGCAGATAAAGGGCGCCACGCCTAGAGACTCCGGCCTCTATGCTTGTACTGCCA<br>GTAGGACTGTAGACAGTGAAACTTGGTACTTCATGGTGAATGTCACAGATGCCAT<br>CTCATCCGGAGATGATGAGGATGACACCGATGGTGCGGAAGATTTTGTCAGTGA<br>GAACAGTAACAACAAGAGAGCACCATACTGGACCAACACAGAAAAGATGGAAA<br>AGCGGCTCCATGCTGTGCCTGCGGCCAACACTGTCAAGTTTCGCTGCCCAGCCGG<br>GGGGAACCCAATGCCAACCATGCGGTGGCTGAAAAACGGGAAGGAGTTTAAGCA<br>GGAGCATCGCATTGGAGGCTACAAGGTACGAAACCAGCACTGGAGCCTCATTAT<br>GGAAAGTGTGGTCCCATCTGACAAGGGAAATTATACCTGTGTAGTGGAGAATGA<br>ATACGGGTCCATCAATCACACGTACCACCTGGATGTTGTGGAGCGATCGCCTCAC<br>CGGCCCATCCTCCAAGCCGGACTGCCGGCAAATGCCTCCACAGTGGTCGGAGGA<br>GACGTAGAGTTTGTCTGCAAGGTTTACAGTGATGCCCAGCCCCACATCCAGTGGA<br>TCAAGCACGTGGAAAAGAACGGCAGTAAATACGGGCCGACGGGCTGCCCTACC<br>TCAAGGTTCTCAAGGCCGCCGGTGTTAACACCACGGACAAAGAGATTGAGGTTC<br>TCTATATTCGGAATGTAACTTTTGAGGACGCTGGGGAATATACGTGCTTGGCGGG<br>TAATTCTATTGGGATATCCTTTCACTCTGCATGGTTGACAGTTCTGCCAGCGCCTG<br>GAAGAGAAAAGGAGATTACAGCTTCCCCAGACTACCTGGAGATAGCCATTTACT |

TABLE 6-continued

```
GCATAGGGGTCTTCTTAATCGCCTGTATGGTGGTAACAGTCATCCTGTGCCGAAT
GAAGAACACGACCAAGAAGCCAGACTTCAGCAGCCAGCCGGCTGTGCACAAGCT
GACCAAACGTATCCCCCTGCGGAGACAGGTAACAGTTTCGGCTGAGTCCAGCTCC
TCCATGAACTCCAACACCCCGCTGGTGAGGATAACAACACGCCTCTCTTCAACGG
CAGACACCCCCATGCTGGCAGGGGTCTCCGAGTATGAACTTCCAGAGGACCCAA
AATGGGAGTTTCCAAGAGATAAGCTGACACTGGGCAAGCCCCTGGGAGAAGGTT
GCTTTGGGCAAGTGGTCATGGCGGAAGCAGTGGGAATTGACAAAGACAAGCCCA
AGGAGGCGGTCACCGTGGCCGTGAAGATGTTGAAAGATGATGCCACAGAGAAAG
ACCTTTCTGATCTGGTGTCAGAGATGGAGATGATGAAGATGATTGGGAAACACA
AGAATATCATAAATCTTCTTGGAGCCTGCACACAGGATGGGCCTCTCTATGTCAT
AGTTGAGTATGCCTCTAAAGGCAACCTCCGAGAATACCTCCGAGCCCGGAGGCC
ACCCGGGATGGAGTACTCCTATGACATTAACCGTGTTCCTGAGGAGCAGATGACC
TTCAAGGACTTGGTGTCATGCACCTACCAGCTGGCCAGAGGCATGGAGTACTTGG
CTTCCCAAAAATGTATTCATCGAGATTTAGCAGCCAGAAATGTTTTGGTAACAGA
AAACAATGTGATGAAAATAGCAGACTTTGGACTCGCCAGAGATATCAACAATAT
AGACTATTACAAAAAGACCACCAATGGGCGGCTTCCAGTCAAGTGGATGGCTCC
AGAAGCCCTGTTTGATAGAGTATACACTCATCAGAGTGATGTCTGGTCCTTCGGG
GTGTTAATGTGGGAGATCTTCACTTTAGGGGGCTCGCCCTACCCAGGGATTCCCG
TGGAGGAACTTTTTAAGCTGCTGAAGGAAGGACACAGAATGGATAAGCCAGCCA
ACTGCACCAACGAACTGTACATGATGATGAGGGACTGTTGGCATGCAGTGCCCTC
CCAGAGACCAACGTTCAAGCAGTTGGTAGAAGACTTGGATCGAATTCTCACTCTC
ACAACCAATGAGACACAACTTCGAAACCAGCTAATTCATGAGTTGATGCACCCT
GTATTGAGTGGAGAACTGCAGCCTCGGTCCATTTCAGTAGAAGGGAGCTCCCTCT
TAATAGGCGCCTCTAACTCTTTAGTGGCAGATCACTTACAAAGATGTGGCTATGA
ATATTCACTTTCTGTTTTCTTTCCAGAAAGTGGTTTGGCAAAAGAAAAGGTATTTA
CTATGCAGGATCTATTACAACTCATTAAAATCAACCCTACTTCCAGTCTCTACAA
ATCACTGGTTTCAGGATCTGATAAAGAAAATCAAAAAGGTTTTCTTATGCATTTT
TTAAAAGAATTGGCAGAATATCATCAAGCTAAAGAGAGTTGTAATATGGAAACT
CAGACAAGTTCGACATTTAACAGAGATTCTCTGGCTGAGAAGCTTCAGCTTATTG
ATGATCAGTTTGCAGATGCTTACCCTCAGCGTATCAAGTTCGAATCTTTAGAAAT
AAAGCTAAATGAGTATAAGAGAGAAATAGAAGAGCAACTTCGGGCAGAAATGT
GTCAAAAGTTGAAGTTTTTTAAAGATACCGAGATAGCAAAAATTAAAATGGAAG
CAAAAAAAAAGTATGAAAAGGAGTTAACCATGTTCCAGAATGATTTTGAAAAAG
CTTGTCAAGCAAAATCTGAAGCTCTCGTTCTTCGGGAAAAGAGTACCCTTGAAAG
AATTCACAAGCACCAAGAGATTGAAACAAAAGAAATTTATGCTCAAAGGCAACT
TTTACTAAAAGATATGGATTTGCTAAGAGGAAGAGAAGCAGAGCTGAAGCAAAG
AGTTGAAGCTTTTGAATTGAACCAGAAGCTCCAGGAAGAAAAACATAAAAGCAT
AACTGAGGCACTTAGGAGACAGGAGCAGAATATAAAGAGTTTTGAGGAGACCTA
TGACCGAAAGCTCAAGAATGAACTTCTAAAGTATCAACTTGAACTGAAGGATGA
CTACATCATTAGAACTAATCGACTGATTGAAGATGAAAGGAAGAATAAAAGAAA
AGCTGTTCATTTGCAAGAGGAGCTCATAGCTATTAATTCAAAAAAGGAGGAACT
CAATCAATCTGTAAATCGTGTGAAAGAACTTGAGCTTGAATTAGAGTCTGTCAAA
GCCCAGTCTTTGGCAATAACAAAACAAAACCATATGCTGAATGAAAAGGTTAAA
GAGATGAGTGATTATTCACTACTAAAAGAAGAGAAACTGGAGCTTCTGGCACAA
AATAAATTACTTAAACAACAACTGGAAGAGAGTAGAAATGAAAACCTGCGTCTC
CTAAACCGCCTAGCTCAGCCGGCTCCTGAACTTGCAGTCTTTCAGAAAGAACTAC
GGAAAGCCGAAAAGGCTATAGTGGTTGAGCATGAGGAGTTCGAAAGCTGCAGGC
AAGCTCTGCACAAACAACTGCAAGACGAAATTGAGCATTCTGCACAGCTGAAGG
CCCAGATTCTAGGTTACAAAGCTTCTGTAAAGAGTTTAACTACTCAGGTTGCCGA
TTTTAAAATTGCAACTGAAGCAAACTCAGACAGCCCTAGAGAATGAAGTGTACTG
CAATCCAAAGCAGTCTGTGATCGATCGTTCTGTCAATGGATTAATAAATGGCAAT
GTGGTGCCTTGCAATGGTGAGATAAGTGGGGATTTCTTGAACAATCCTTTTAAAC
AGGAAAACGTTCTAGCACGTATGGTTGCATCAAGGATCACAAATTATCCAACTGC
ATGGGTGGAGGGTAGTTCCCCTGATTCTGACCTTGAGTTTGTAGCCAATACTAAG
GCAAGGGTCAAAGAGCTTCAGCAAGAGGCCGAACGCTTGGAAAAGGCTTTCAGA
AGTTACCATCGGAGAGTCATTAAAAACTCTGCCAAAAGCCCACTAGCAGCAAAG
AGCCCACCATCTCTGCACTTGCTGGAAGCCTTCAAAAACATTACTTCCAGTTCCC
CGGAAAGACATATTTTTGGAGAGGACAGAGTTGTCTCTGAGCAGCCTCAAGTGG
GCACACTTGAAGAAAGGAATGACGTCGTGGAAGCACTGACAGGCAGTGCAGCCT
CGAGGCTCCGCGGGGGCACTTCCTCCAGACGCCTCTCTTCCACACCCCTTCCAAA
AGCAAAAAGAAGCCTCGAAAGTGAAATGTATCTGGAAGGTCTGGGCAGATCACA
CATTGCTTCCCCCAGTCCTTGTCCTGACAGAATGCCCCTACCATCACCCACTGAGT
CTAGGCACAGCCTCTCCATCCCTCCTGTCTCCAGCCCTCCGGAGCAGAAAGTGGG
TCTTTATCGAAGACAAACTGAACTTCAAGACAAAAGTGAATTTTCAGATGTGGAC
AAGCTAGCTTTTAAGGATAATGAGGAGTTTGAATCATCTTTTGAATCTGCAGGGA
ACATGCCAAGGCAGTTGGAAATGGGCGGGCTTTCTCCTGCCGGGGATATGTCTCA
TGTGGACGCTGCTGCAGCTGCTGTGCCCCTCTCATATCAGCACCCAAGTGTAGAT
CAGAAACAAATTGAAGAACAAAAGGAAGAAGAAAAATACGGGAACAGCAAGT
GAAAGAACGAAGGCAGAGAAGAAAGAAGGCAGAGTAACCTACAAGAAGTTT
TAGAAAGGGAACGAAGAGAACTAGAAAAACTGTATCAGGAAAGGAAGATGATT
GAAGAATCACTGAAGATTAAAATAAAAAAGGAATTAGAAATGGAAAATGAATT
AGAAATGAGTAATCAAGAAATAAAAGACAAATCTGCTCACAGTGAAAATCCTTT
AGAGAAATACATGAAAATCATCCAGCAGGAGCAAGACCAGGAGTCGGCAGATA
AGAGCTCAAAAAGATGGTCCAAGAAGGCTCCCTAGTGGACACGCTGCAATCTA
GTGACAAAGTCGAAAGTTTAACAGGCTTTTCTCATGAAGAACTAGACGACTCTTG
GTAA
```

What is claimed:

1. A method of treating cancer in a patient comprising:

administering to the patient a pharmaceutically effective amount of an antibody that blocks the interaction between PD-1 and PD-L1;

monitoring the efficacy of the antibody; and if the antibody is not efficacious, evaluating a biological sample from the patient for a presence of one or more FGFR variants, wherein the one or more FGFR variants comprise an FGFR fusion gene, and wherein the FGFR fusion gene is FGFR2:AFF3; FGFR2:BICC1; FGFR2:CASP7; FGFR2:CCDC6; FGFR2:OFD1; FGFR3:BAIAP2L1; FGFR3:TACC3-Intron; FGFR3:TACC3V1; FGFR3:TACC3V3; or a combination thereof; and administering to the patient a pharmaceutically effective amount of an FGFR inhibitor if the one or more FGFR variants are present in the sample, wherein the FGFR inhibitor is the compound of formula (I):

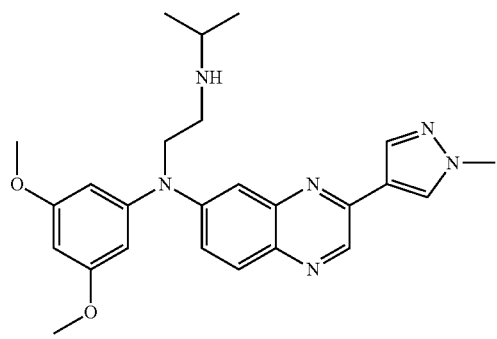

or a pharmaceutically acceptable salt thereof.

2. The method of claim 1, wherein the evaluating step further comprises measuring an expression level of PD-L1 in a biological sample and wherein the second administering step comprises administering the FGFR inhibitor if:

the biological sample has a PD-L1 expression corresponding to an H-score of about 0 to about 99; or the biological sample has a PD-L1 expression level that is lower than a reference PD-L1 expression level.

3. The method of claim 1 or 2, wherein the biological sample is blood, lymph fluid, bone marrow, a solid tumor sample, or any combination thereof.

4. The method of claim 1, wherein the cancer is lung cancer, bladder cancer, gastric cancer, breast cancer, ovarian cancer, head and neck cancer, esophageal cancer, glioblastoma, or any combination thereof.

5. The method of claim 4, wherein the lung cancer is non-small cell lung cancer (NSCLC) adenocarcinoma, NSCLC squamous cell carcinoma, small cell lung cancer, or any combination thereof.

6. The method of claim 1, wherein the one or more FGFR variants further comprise an FGFR mutation, an FGFR amplification, or a combination thereof.

7. The method of claim 1, wherein the antibody that blocks an interaction between PD-1 and PD-L1 is an anti-PD-1 antibody, an anti-PD-L1 antibody, or a combination thereof.

8. The method of claim 2, wherein the cancer is lung cancer, bladder cancer, gastric cancer, breast cancer, ovarian cancer, head and neck cancer, esophageal cancer, glioblastoma, or any combination thereof.

9. The method of claim 8, wherein the lung cancer is non-small cell lung cancer (NSCLC) adenocarcinoma, NSCLC squamous cell carcinoma, small cell lung cancer, or any combination thereof.

10. The method of claim 2, wherein the one or more FGFR variants further comprise an FGFR mutation, an FGFR amplification, or a combination thereof.

11. The method of claim 2, wherein the antibody that blocks an interaction between PD-1 and PD-L1 is an anti-PD-1 antibody, an anti-PD-L1 antibody, or a combination thereof.

12. The method of claim 3, wherein the cancer is lung cancer, bladder cancer, gastric cancer, breast cancer, ovarian cancer, head and neck cancer, esophageal cancer, glioblastoma, or any combination thereof.

13. The method of claim 12, wherein the lung cancer is non-small cell lung cancer (NSCLC) adenocarcinoma, NSCLC squamous cell carcinoma, small cell lung cancer, or any combination thereof.

14. The method of claim 3, wherein the one or more FGFR variants further comprise an FGFR mutation, an FGFR amplification, or a combination thereof.

15. The method of claim 3, wherein the antibody that blocks an interaction between PD-1 and PD-L1 is an anti-PD-1 antibody, an anti-PD-L1 antibody, or a combination thereof.

16. The method of claim 1, wherein the biological sample:
    has a PD-L1 expression corresponding to an H-score of less than 20; or
    has a PD-L1 expression level that is lower than a reference PD-L1 expression level.

17. The method of claim 16, where the biological sample has a PD-L1 expression corresponding to an H-score of less than 20.

* * * * *